United States Patent
Cho et al.

(10) Patent No.: US 10,494,611 B2
(45) Date of Patent: Dec. 3, 2019

(54) COMPOSITIONS COMPRISING A MITOFUSIN INHIBITOR FOR PROMOTING CELL REPROGRAMMING AND A USE THEREOF

(71) Applicant: KOREA RESEARCH INSTITUTE OF BIOSCIENCE AND BIOTECHNOLOGY, Daejeon (KR)

(72) Inventors: Yee Sook Cho, Daejeon (KR); Myung Jin Son, Daejeon (KR); You Jeong Kwon, Daejeon (KR)

(73) Assignee: KOREA RESEARCH INSTITUTE OF BIOSCIENCE AND BIOTECHNOLGY, Daejeon (KR)

( * ) Notice: Subject to any disclaimer, the term of this patent is extended or adjusted under 35 U.S.C. 154(b) by 45 days.

(21) Appl. No.: 14/442,883

(22) PCT Filed: Apr. 23, 2015

(86) PCT No.: PCT/KR2015/004067
§ 371 (c)(1),
(2) Date: Jun. 15, 2015

(87) PCT Pub. No.: WO2016/080608
PCT Pub. Date: May 26, 2016

(65) Prior Publication Data
US 2017/0051254 A1    Feb. 23, 2017

(30) Foreign Application Priority Data
Nov. 20, 2014 (KR) ........................ 10-2014-0162801

(51) Int. Cl.
*C12N 5/074* (2010.01)
*C12N 15/113* (2010.01)

(52) U.S. Cl.
CPC ........ *C12N 5/0696* (2013.01); *C12N 15/1137* (2013.01); *C12Y 306/05* (2013.01); *C12N 2310/14* (2013.01); *C12N 2310/531* (2013.01); *C12N 2500/02* (2013.01); *C12N 2501/65* (2013.01); *C12N 2501/73* (2013.01); *C12N 2501/998* (2013.01); *C12N 2506/02* (2013.01); *C12N 2510/00* (2013.01)

(58) Field of Classification Search
None
See application file for complete search history.

(56) References Cited

U.S. PATENT DOCUMENTS

2007/0275924 A1* 11/2007 Khan ..................... C12N 15/88
514/44 A
2009/0253203 A1 10/2009 Eilertsen et al.
2012/0021519 A1 1/2012 Ichida et al.

FOREIGN PATENT DOCUMENTS

KR    10-2011-0006672 A    1/2011

OTHER PUBLICATIONS

Knowlton, et al. (2012). "Regulating a uniter: control of mitofusin 2 expression". Caridiovascular Research, v.94:6-7.*
Son, M., et al. (2015) "Mitofusins deficiency elicits mitochondrial metabolic reprogramming to pluripotency." Cell Death and Differentiation, v.22:1957-69.*
Fulop et al. (2011) "The Effect of OPA 1 on Mitochondrial Ca2+ Signaling," PLoS ONE. 6(9):e25199. pp. 1-11.
Prigione et al. (Jan. 13, 2014) "HI F1 [alpha]Modulates Cell Fate Reprogramming Through Early Glycolytic Shift and Upregulation of PDK1-3 and PKM2," Stem Cells. 32(2):364-376.
Son et al. (Aug. 9, 2013) "Interference with the mitochondrial bioenergetics fuels reprogramming to pluripotencyviafacilitation of the glycolytic transition," Int. J. Biochem. Cell Biol. 45(11):2512-2518.
Son et al. (Nov. 1, 2013) "Unveiling the critical role of REX1 in the regulation of human stem cell pluripotency," Stem Cells, 31(11):2374-2387.
Westermann (2010) "Mitochondrial fusion and fission in cell life and death," Nature Rev. Mol. Cell Biol. 11 (12):872-884.
Xu et al. (Sep. 1, 2013) "Mitochondrial Regulation in Pluripotent Stem Cells," Cell Metabol. 18(3):325-332.
Hong et al. (2009) "Suppression of induced pluripotent stem cell generation by the p53-p21 pathway," Nature. 460 (7259):1132-1135.
Buganim et al. (Sep. 14, 2012) "Single-Cell Expression Analyses During Cellular Reprogramming Reveal and Early Stochastic and a Late Hierarchic Phase," Cell. 150(6):1209-1222.
Takahashi et al. (2006) "Induction of Pluripotent Stem Cells from Mouse Embryonic and Adult Fibroblast Cultures by Defined Factors," Cell. 126(4):663-676.
Bukowiechi et al. (Nov. 19, 2013) "Mitochondrial function in pluripotent stem cells and cellular reprogramming," Gerontology. 60(2):174-182.

(Continued)

*Primary Examiner* — Jennifer Pitrak McDonald
(74) *Attorney, Agent, or Firm* — Lathrop Gage LLP; Andrew T. Wilkins

(57) ABSTRACT

The present invention relates to a composition comprising a repressor of mitofusin gene expression, an inhibitor of mitofusin protein activity, or a mixture thereof as an active ingredient for promoting reprogramming a differentiated cell into a pluripotent stem cell, and a use thereof. The composition according to the present invention increases the efficiency of reprogramming as well as reduces the time required for reprogramming to produce pluripotent stem cells. Therefore, the present composition can be beneficially used to develop the production technology of high efficiency pluripotent stem cell and secure a large-scale culture system. Further, the present composition can be beneficially used to maintain pluripotent stem cells and screen the compounds capable of promoting the reprogramming into pluripotent stem cells.

8 Claims, 38 Drawing Sheets
Specification includes a Sequence Listing.

(56) References Cited

OTHER PUBLICATIONS

Cherry et al. (Jul. 2013) "Induced pluripotent stem cells with a mitochondrial DNA deletion," Stem Cells. 31(7):1287-1297.
Son et al. (Apr. 17, 2015) "Mitofusins deficiency elicits mitochondrial metabolic reprogramming to pluripotency," Cell Death & Differentiation. 22(12):1957-1969.
Takahashi et al. (2007) "Induction of pluripotent stem cells from adult human fibroblasts by defined factors," Cell. 131(5):861-872.
Vazquez-Martin et al. (Jun. 2012) "Mitochondrial fusion by pharmacological manipulation impedes somatic cell reprogramming to pluripotency: new insight into the rote of mitophagy in cell stemness," Aging. 4(6):393-401.
International Search Report with Written Opinion corresponding to International Patent Application No. PCT/KR2015/004067, dated Jul. 15, 2015.

* cited by examiner

[Figure 1a]
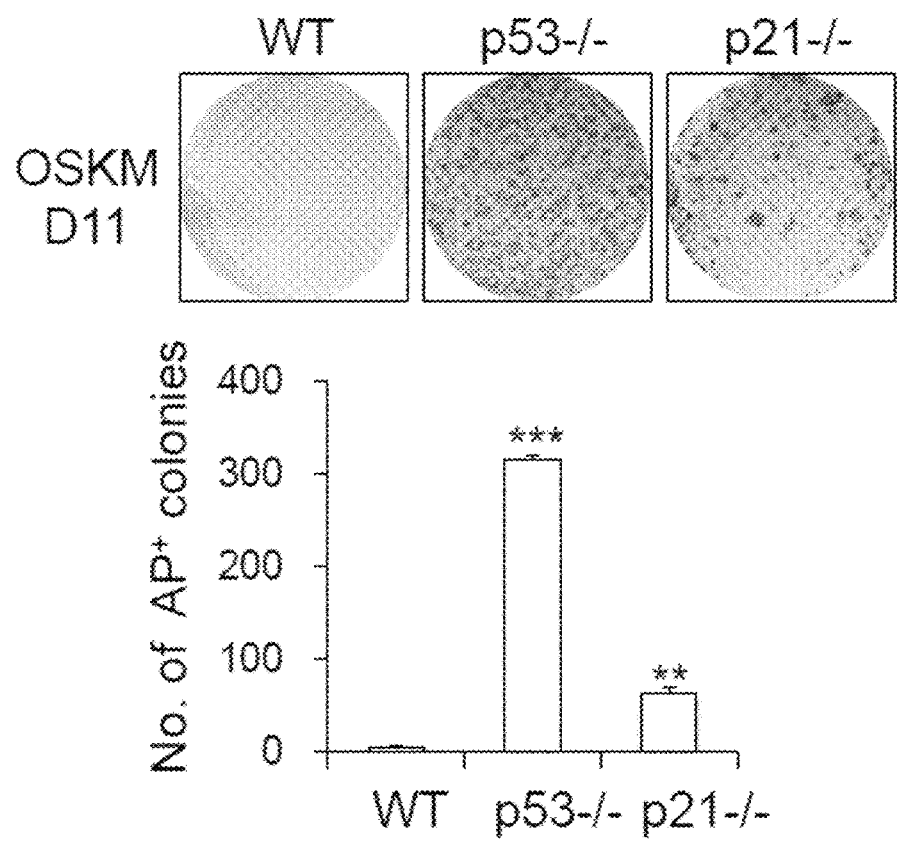

[Figure 1b]
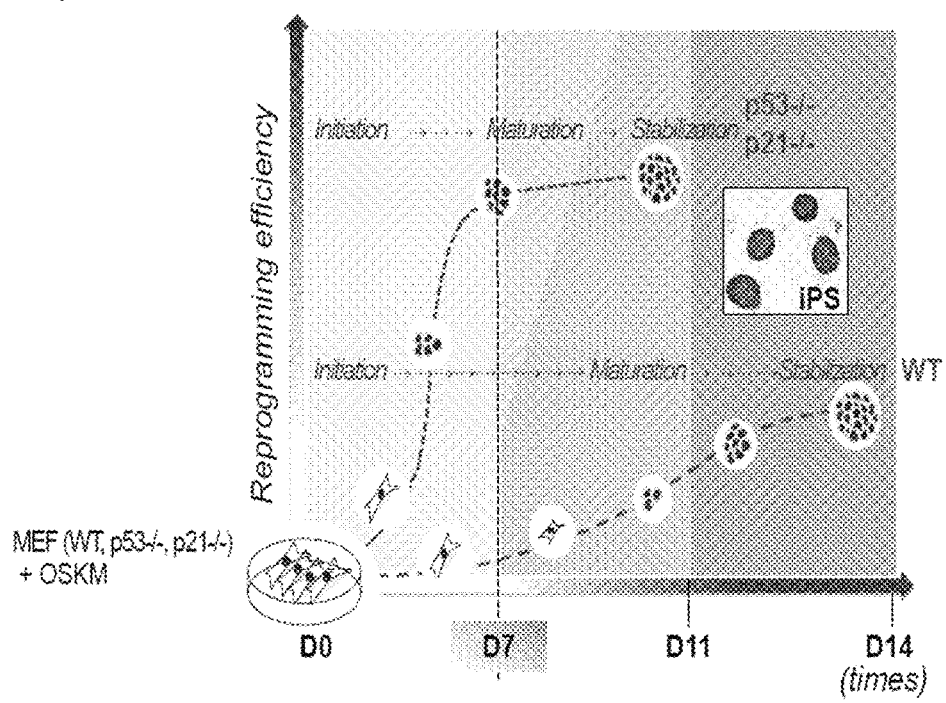
[Figure 1c]
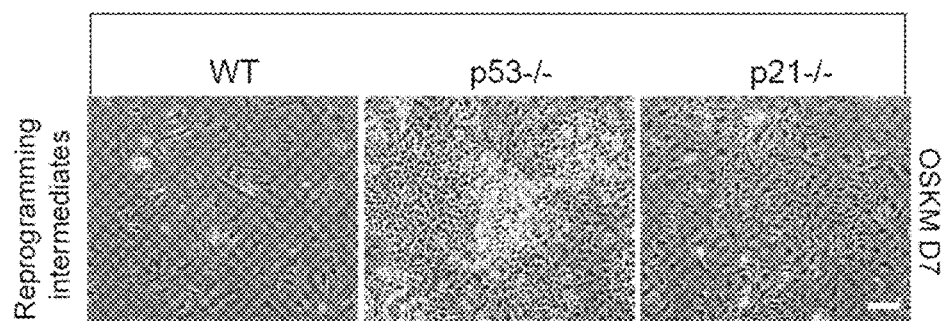

[Figure 1d]
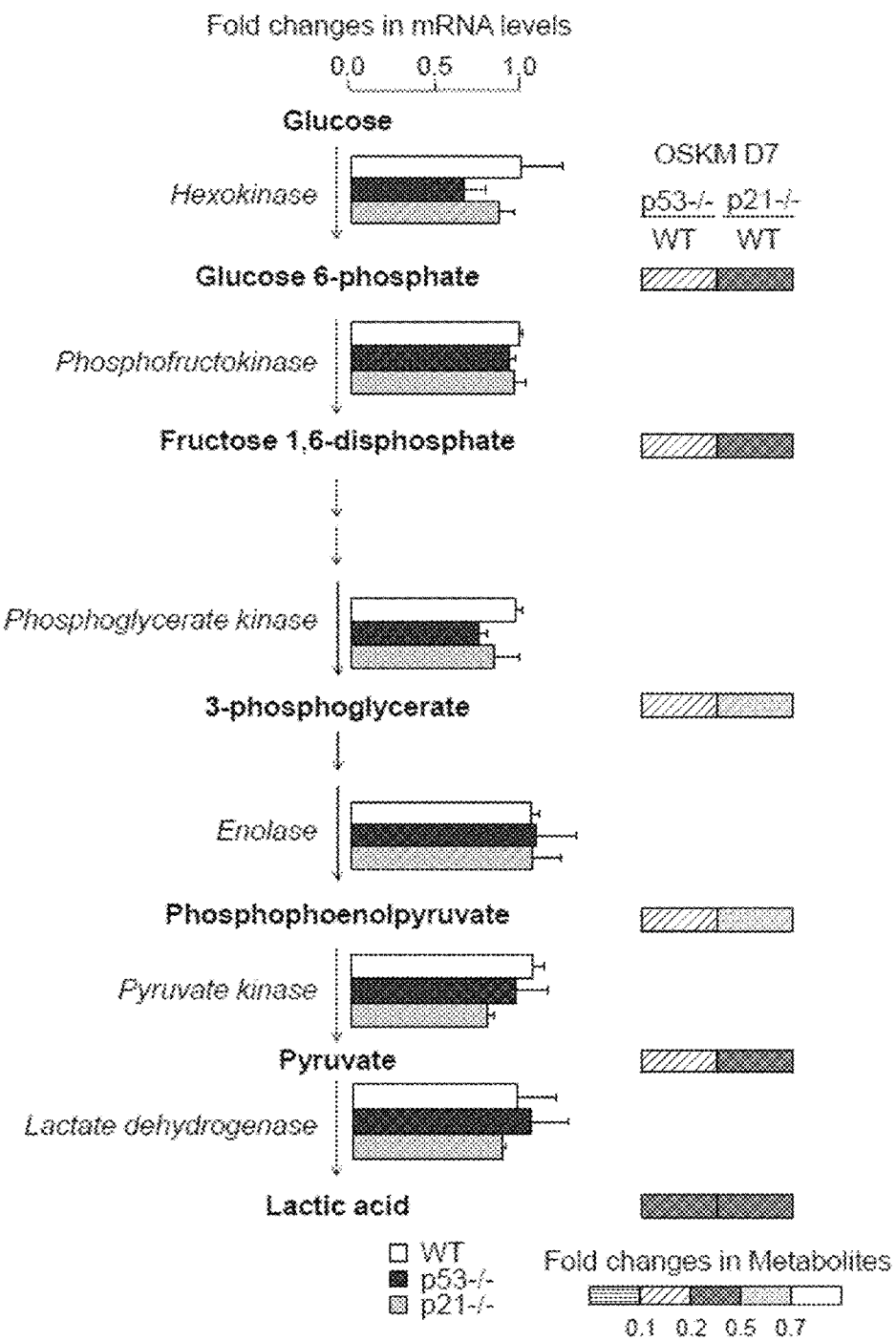

【Figure 1e】
OSKM D7
| Biological process | GeneSymbol | WT | p53-/- | p21-/- |
|---|---|---|---|---|
| TCA | Pdha1 | | | |
| | Aco1 | | | |
| | Idh1 | | | |
| | Sucla2 | | | |
| | Mdh1 | | | |
| Oxidative phosphorylation | ND1 | | | |
| | Ndufa2 | | | |
| | Ndufa5 | | | |
| | Ndufa6 | | | |
| | Atp4a | | | |
| | Atp6v0a2 | | | |
| | Atp6v0e | | | |
| | Atp6v1c1 | | | |
| | Atp6v1e1 | | | |
| | Atp6v1f | | | |
| | Atp6v1h | | | |
| | Atp6ap1 | | | |
| | Sqrdl | | | |
| | Acad10 | | | |
| Mitochondrial fusion | Mfn1 | | | |
| | Mfn2 | | | |
| | Opa1 | | | |
| | Chchd3 | | | |
| Mitochondrial fission | Dnm1 | | | |
| | Dnm1l | | | |
| | Fis1 | | | |
| | Mff | | | |
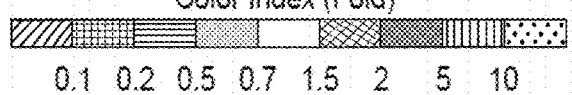
Color Index (Fold)
0.1  0.2  0.5  0.7  1.5  2  5  10

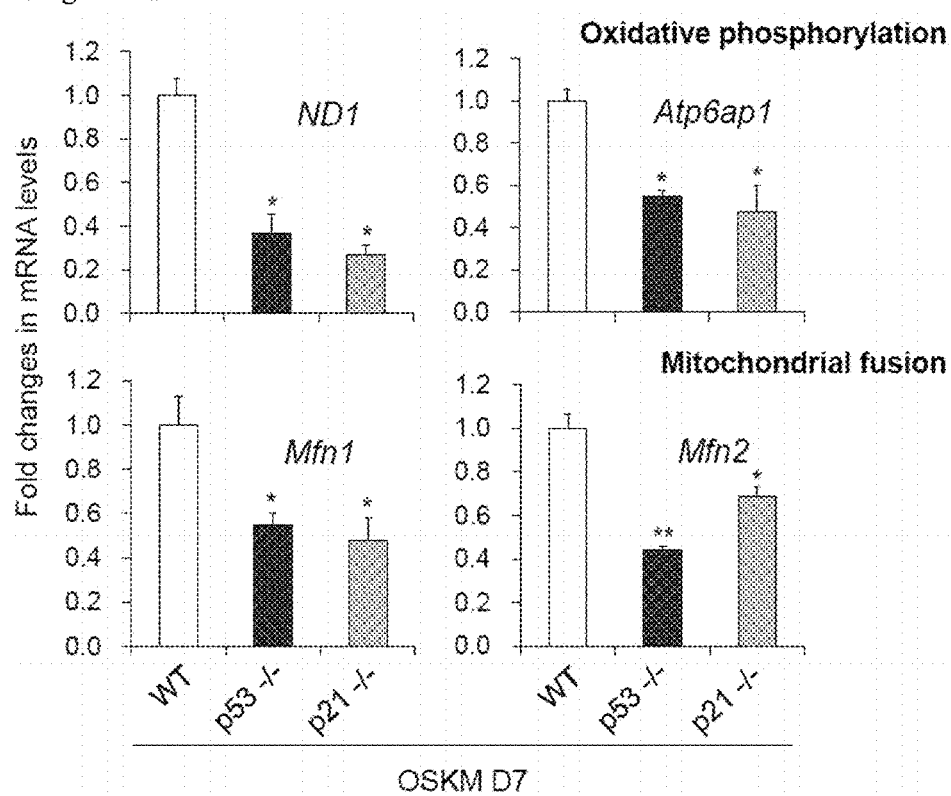

[Figure 2a]
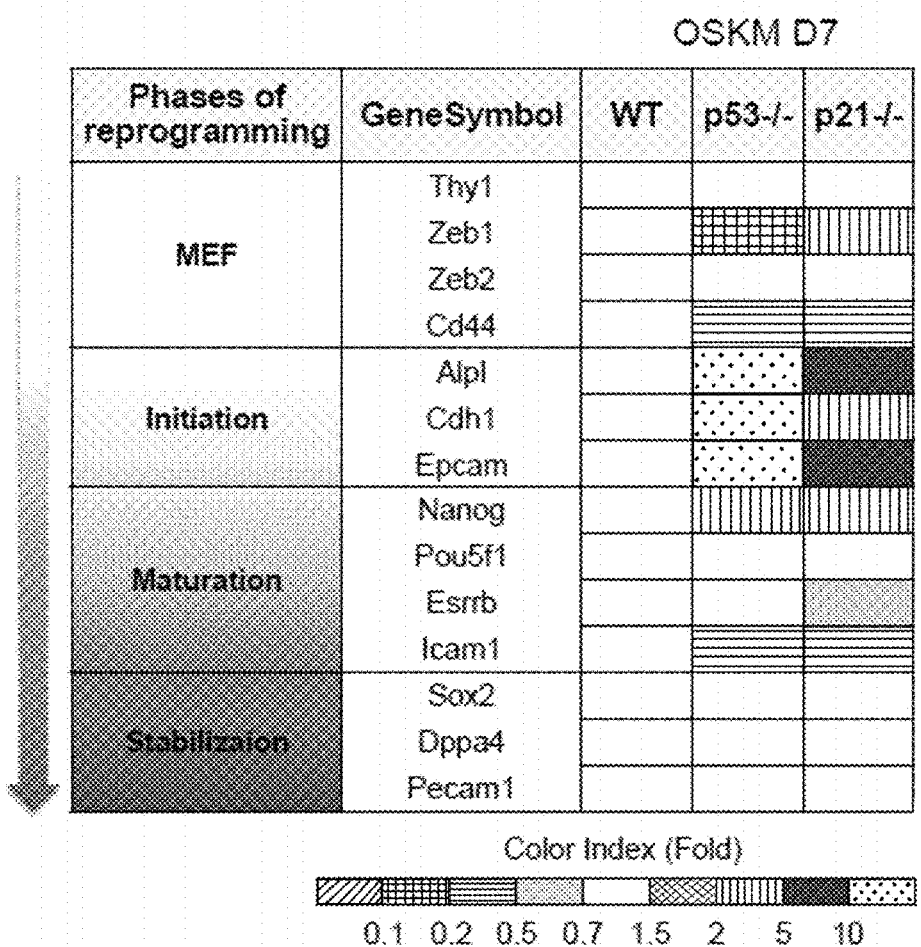

【Figure 2b】
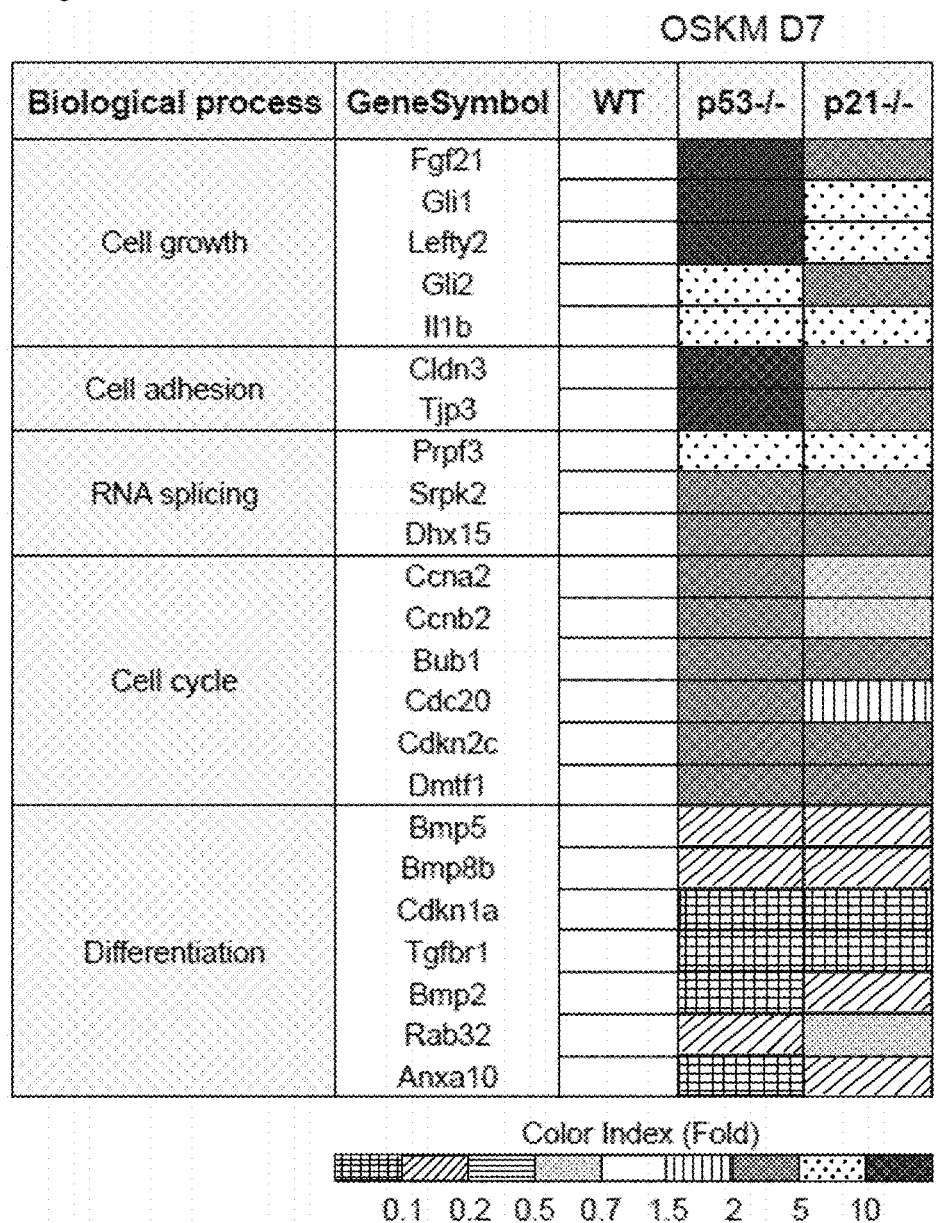

[Figure 2c]
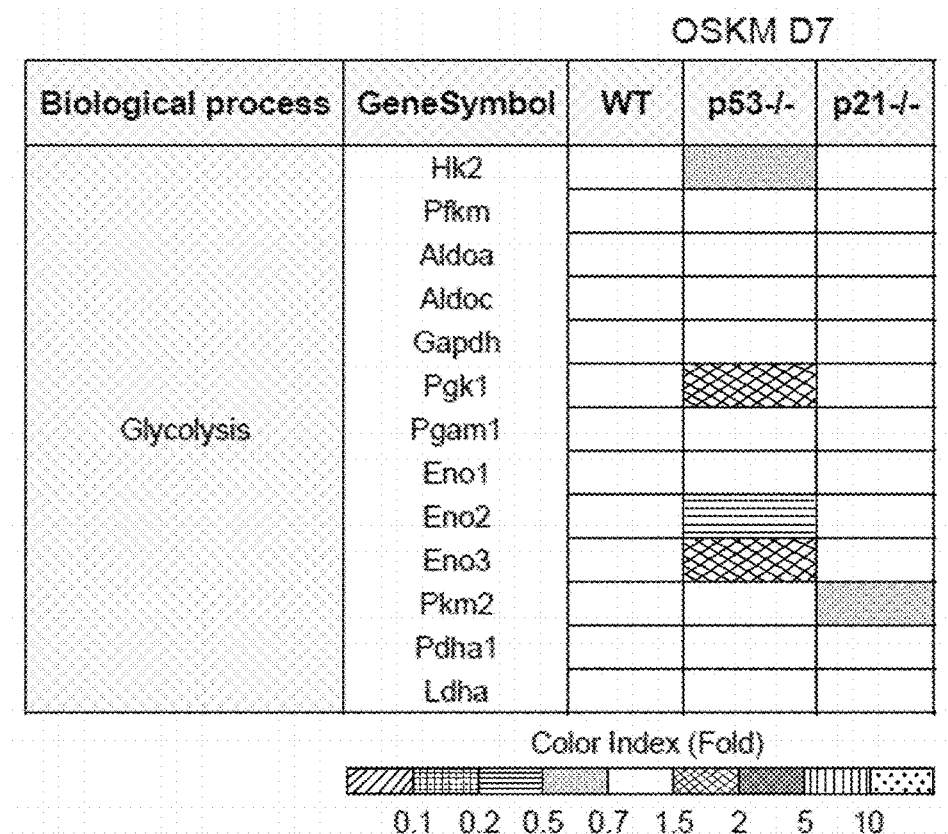
[Figure 3a]
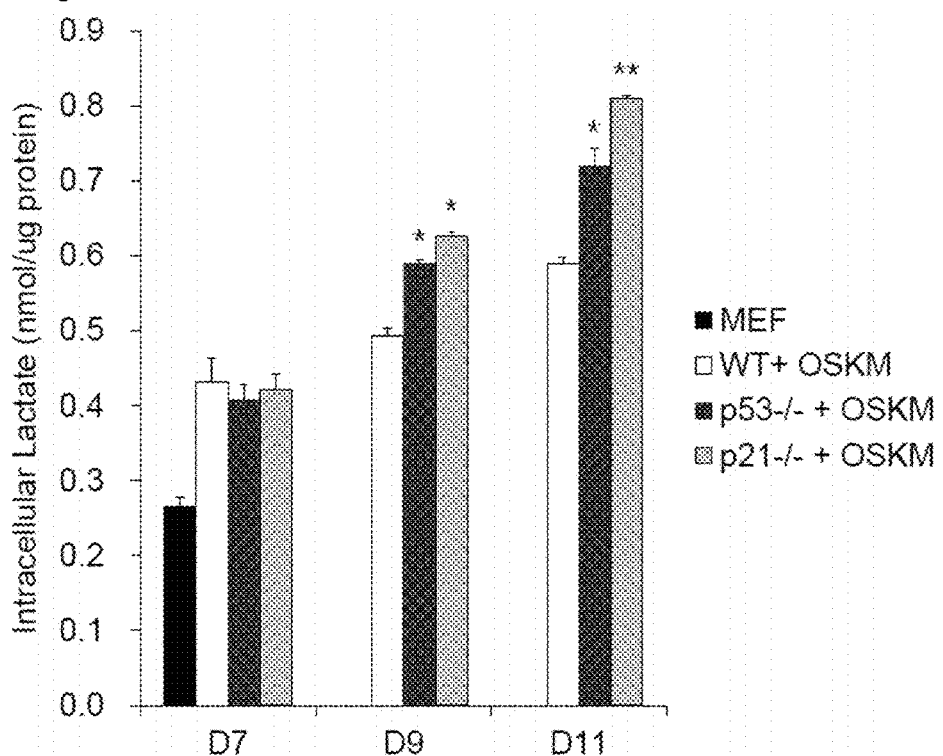

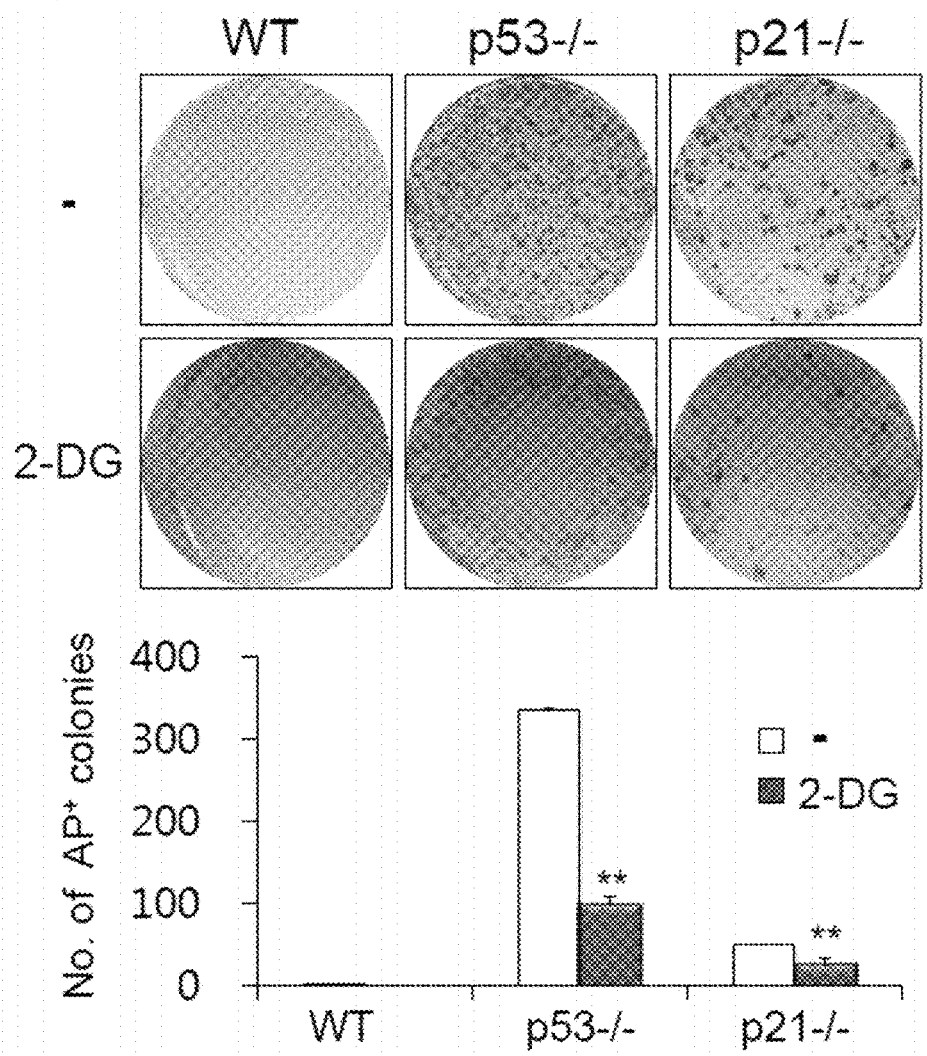
[Figure 3b]

[Figure 4a]
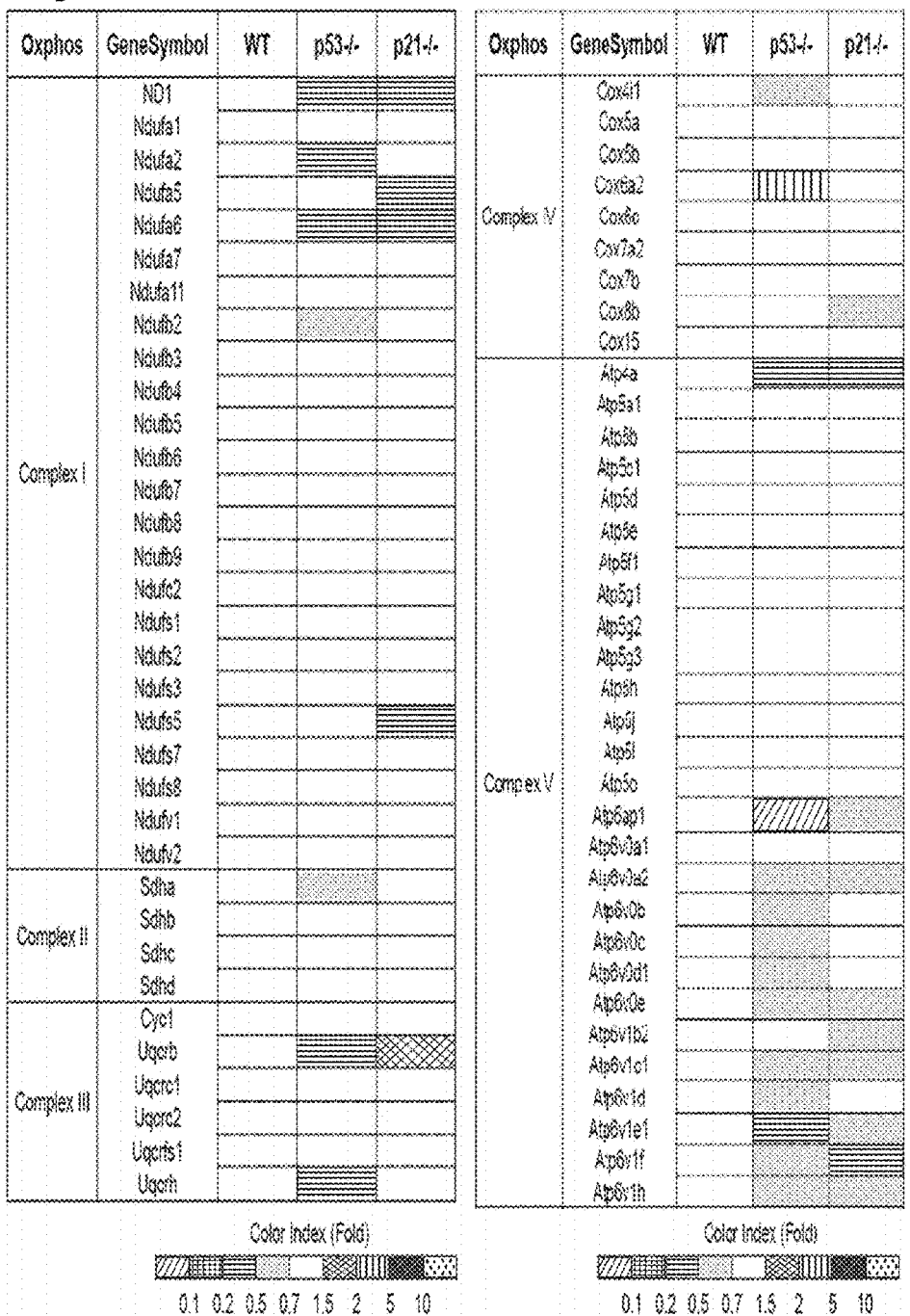

【Figure 4b】
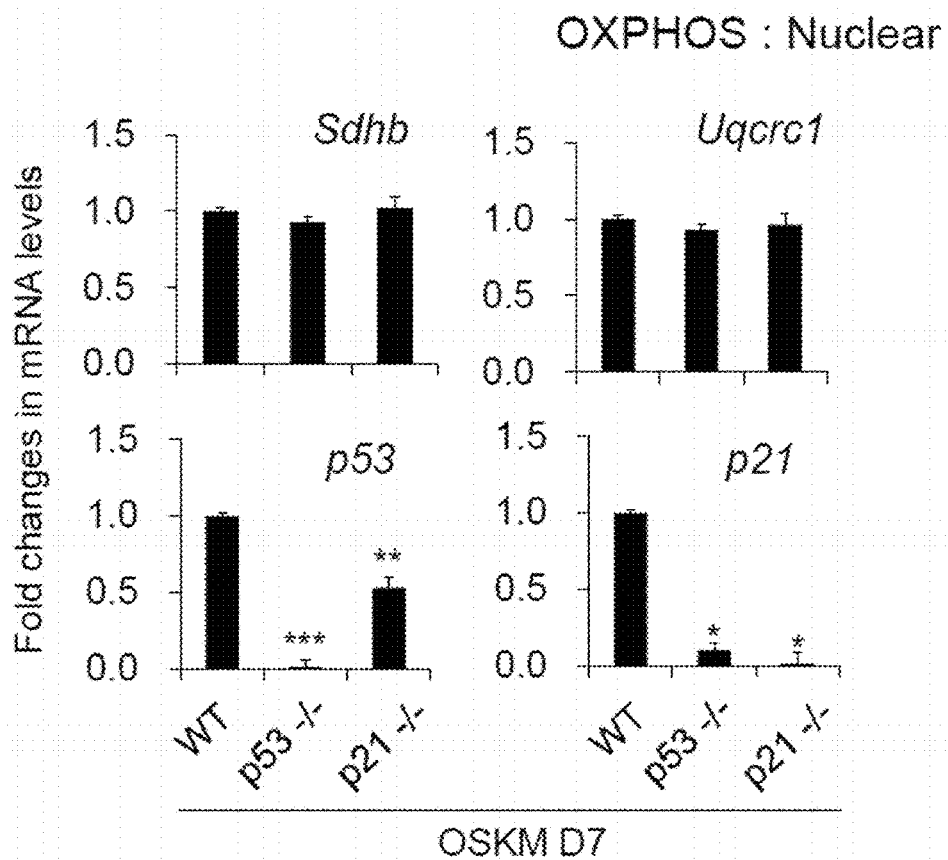
【Figure 4c】
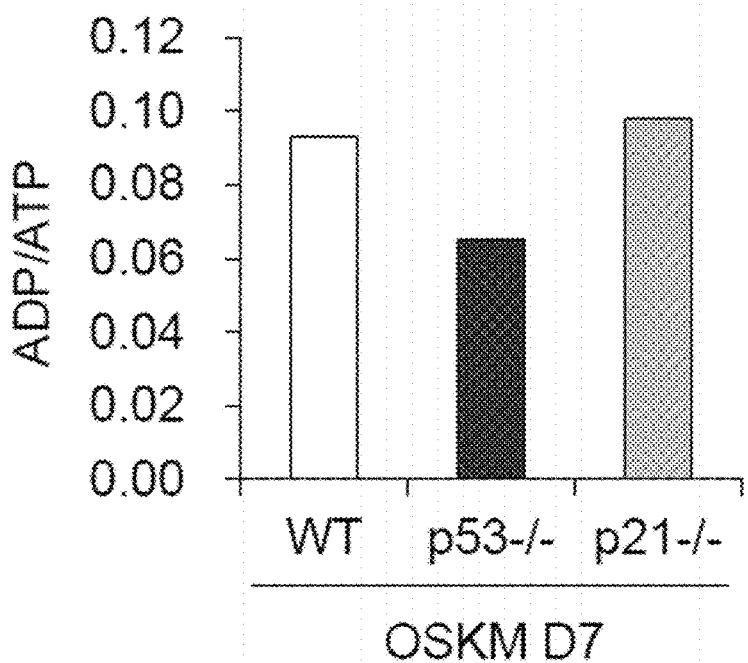

[Figure 5a]
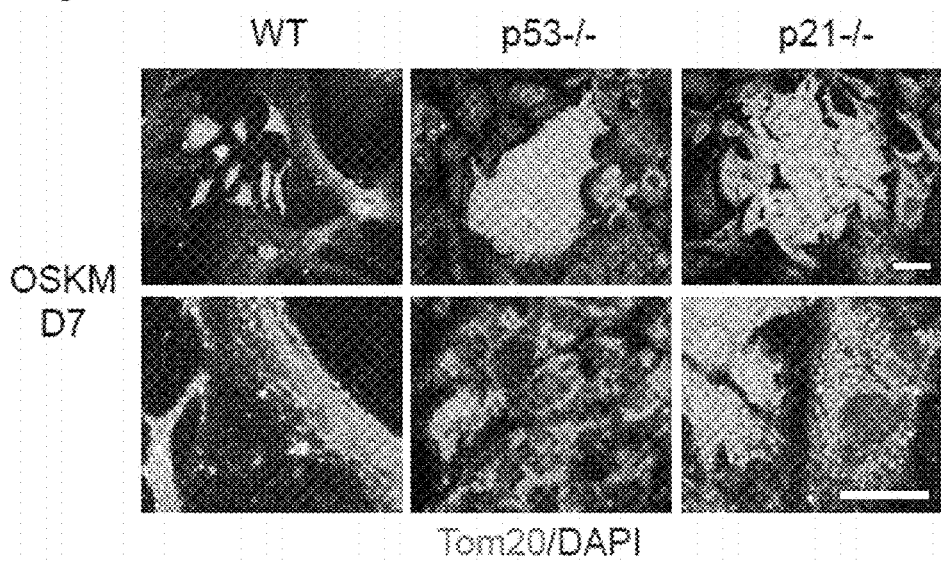
[Figure 5b]
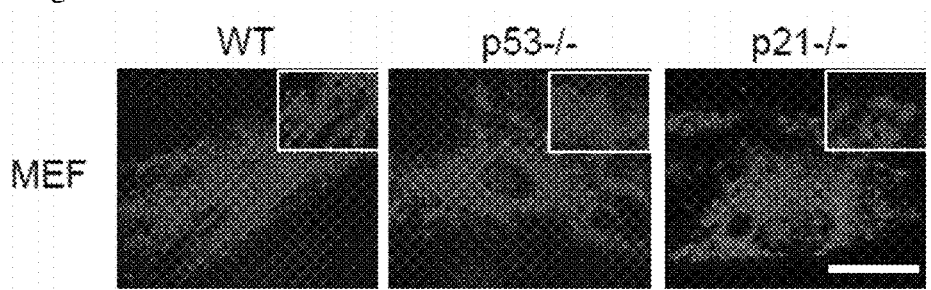

【Figure 5c】
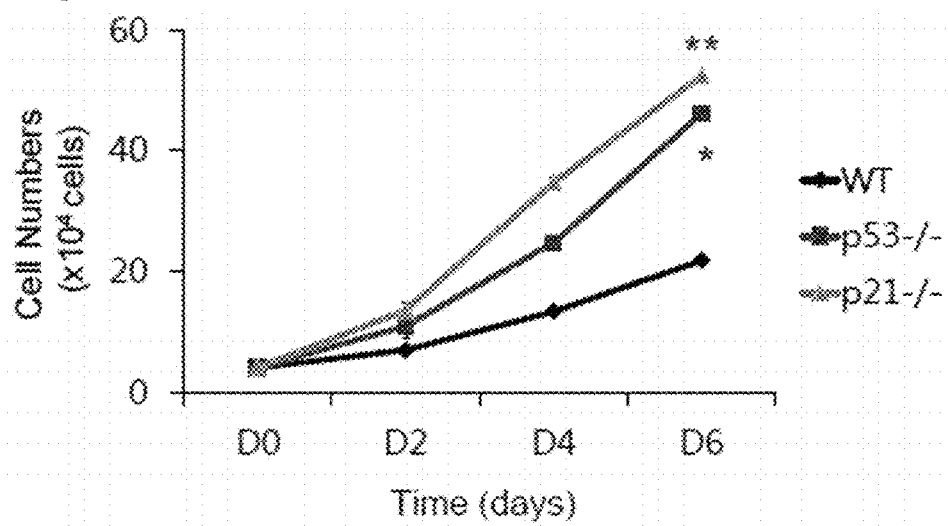
【Figure 5d】
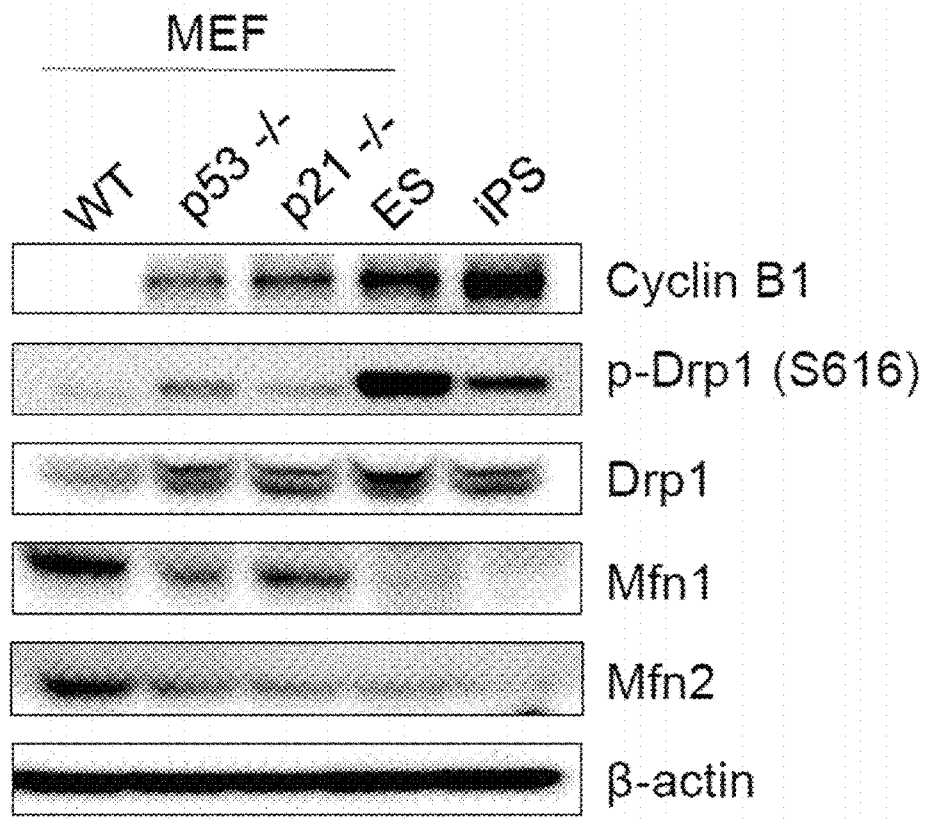

[Figure 5e]
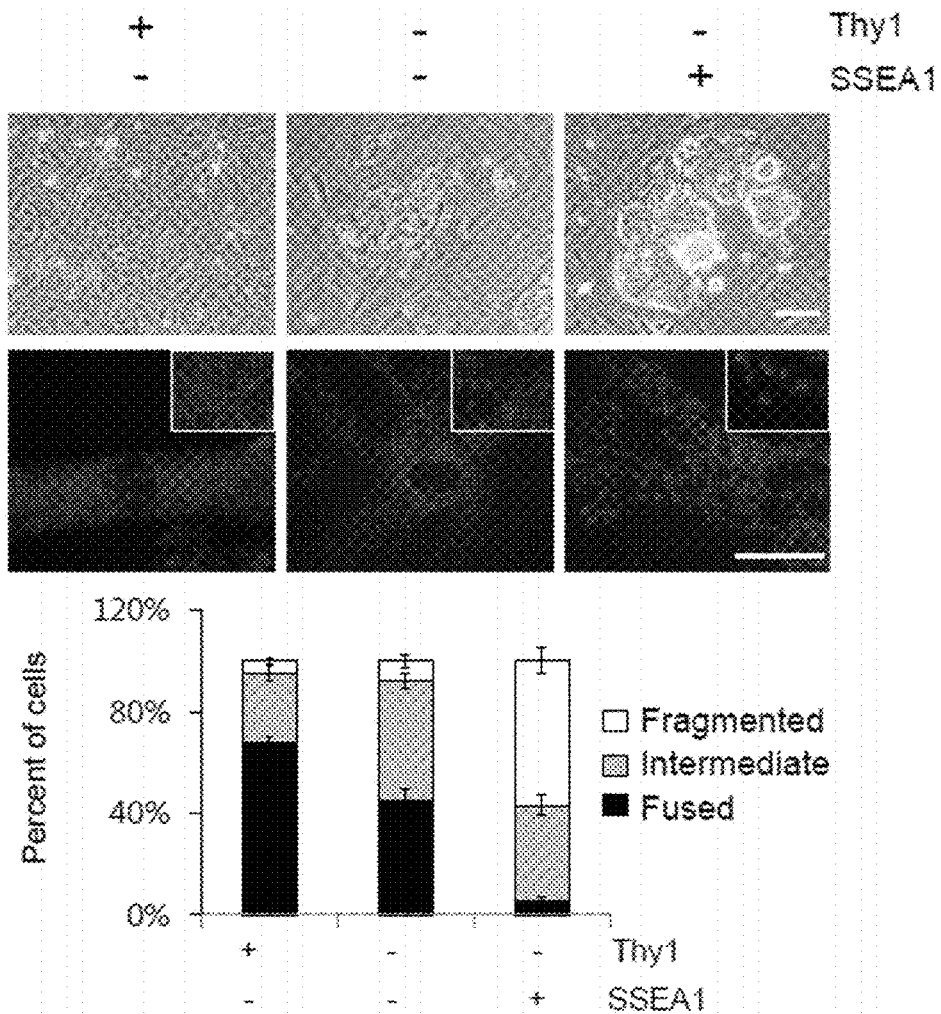
[Figure 5f]
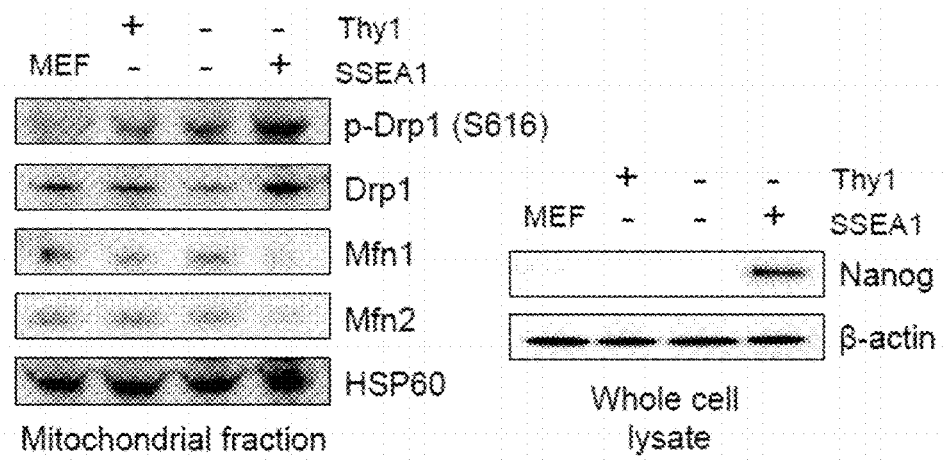

[Figure 5g]
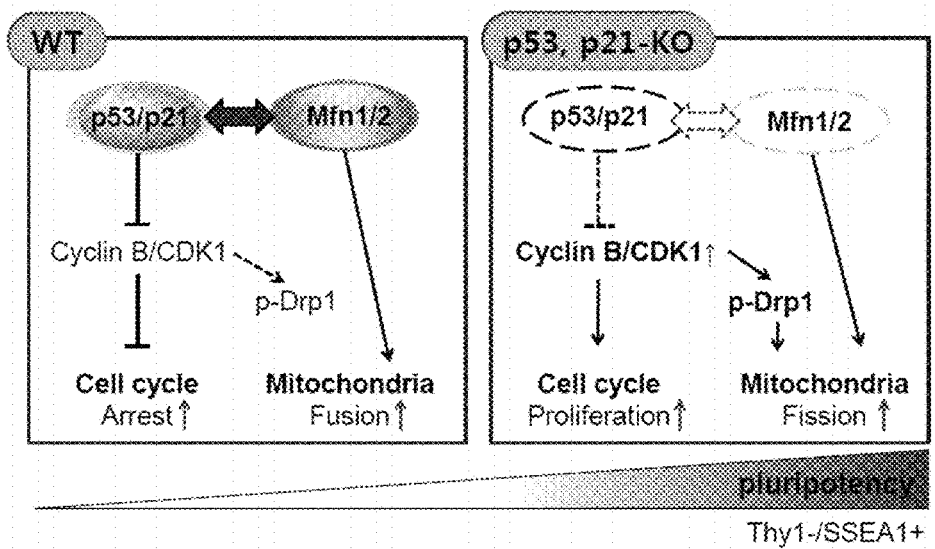
[Figure 6a]
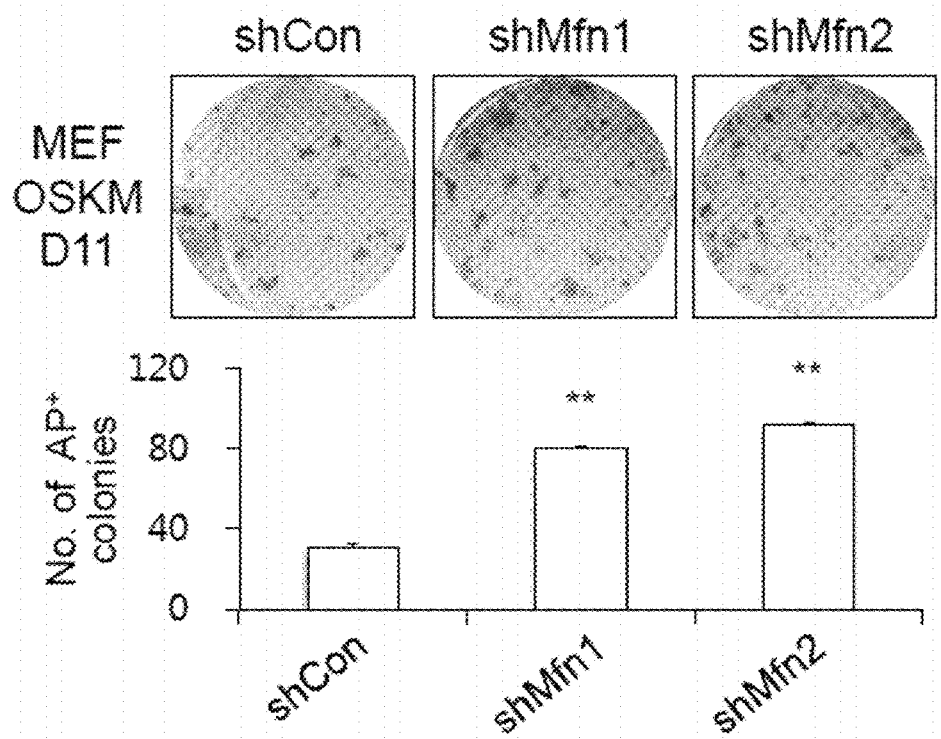

【Figure 6b】
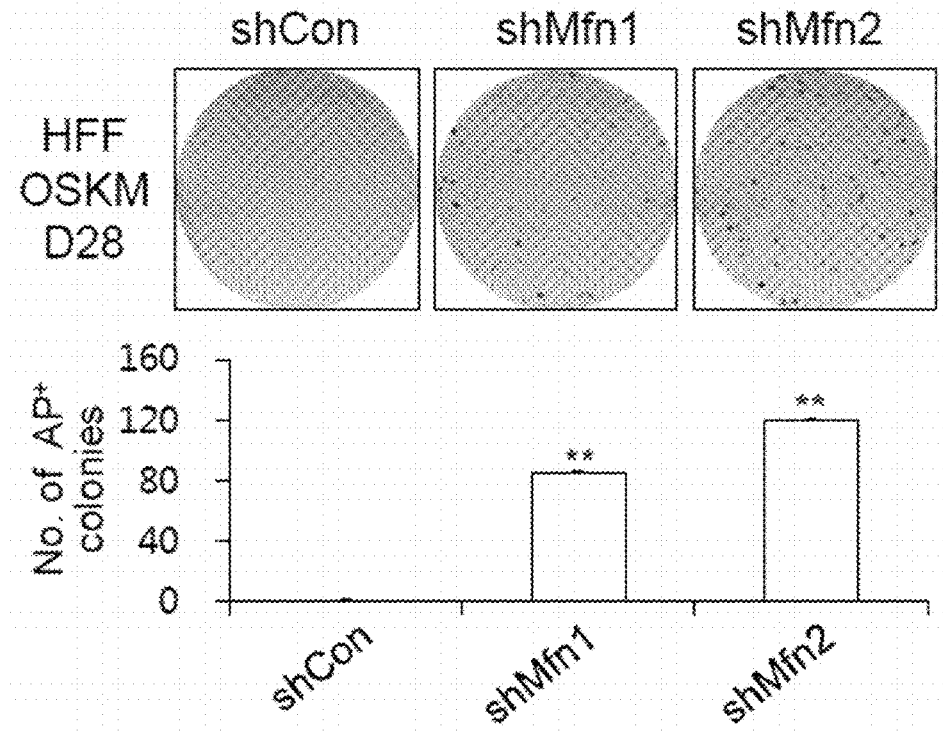
【Figure 6c】
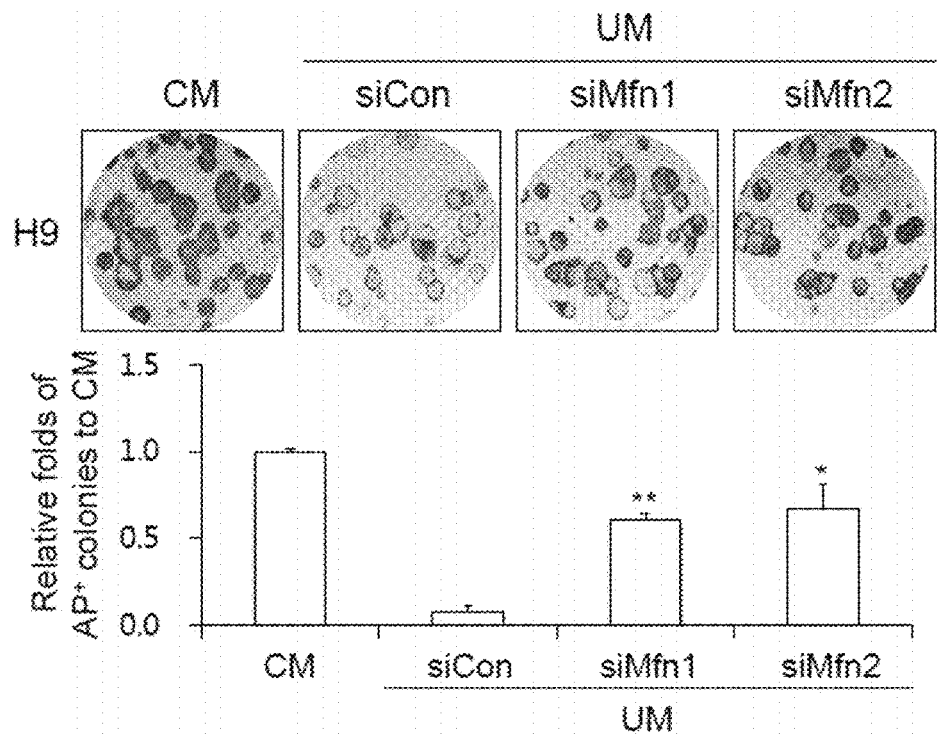

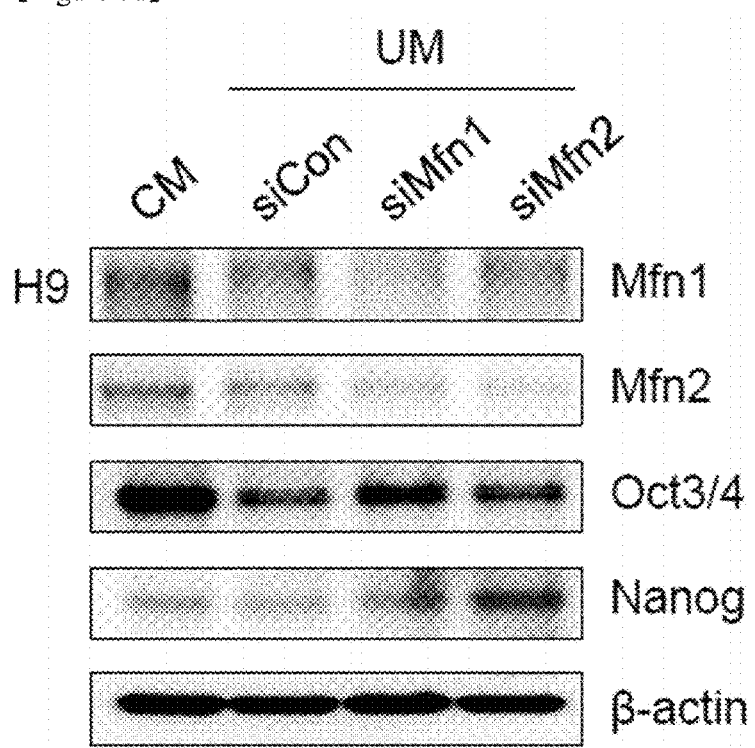
[Figure 6d]

[Figure 6e]
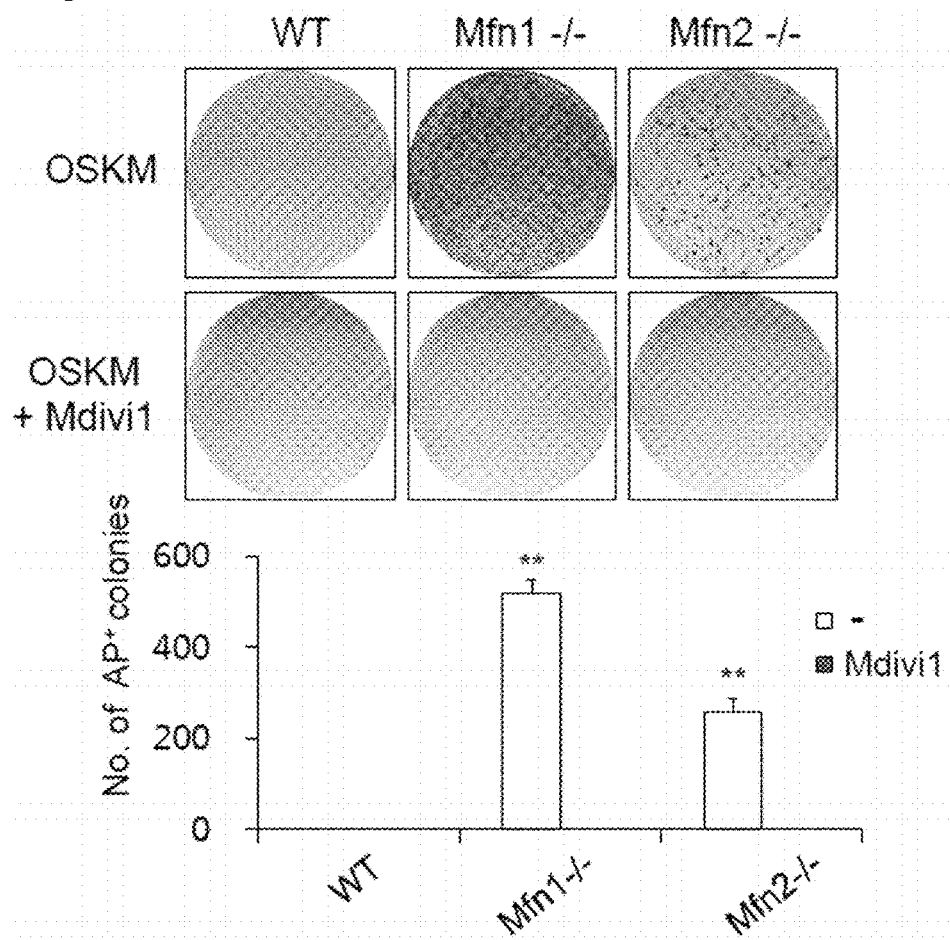
[Figure 6f]
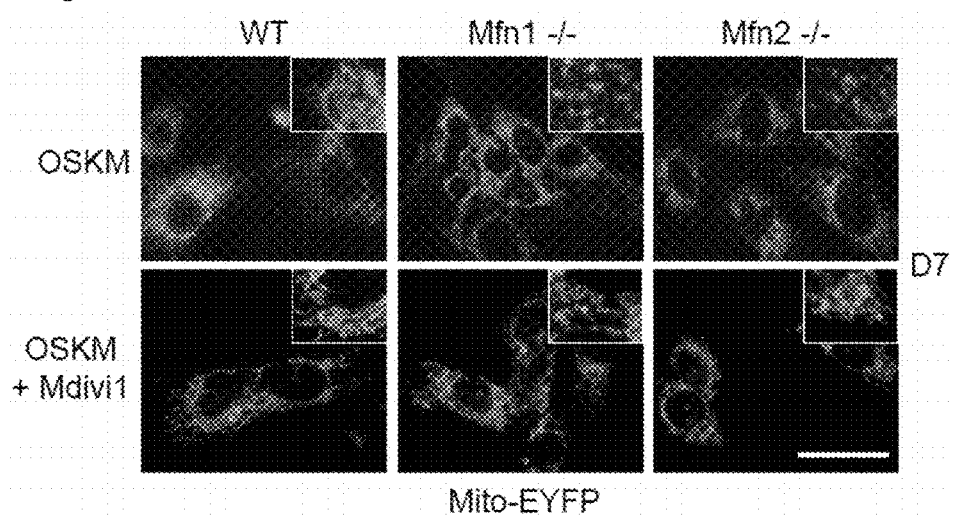
Mito-EYFP

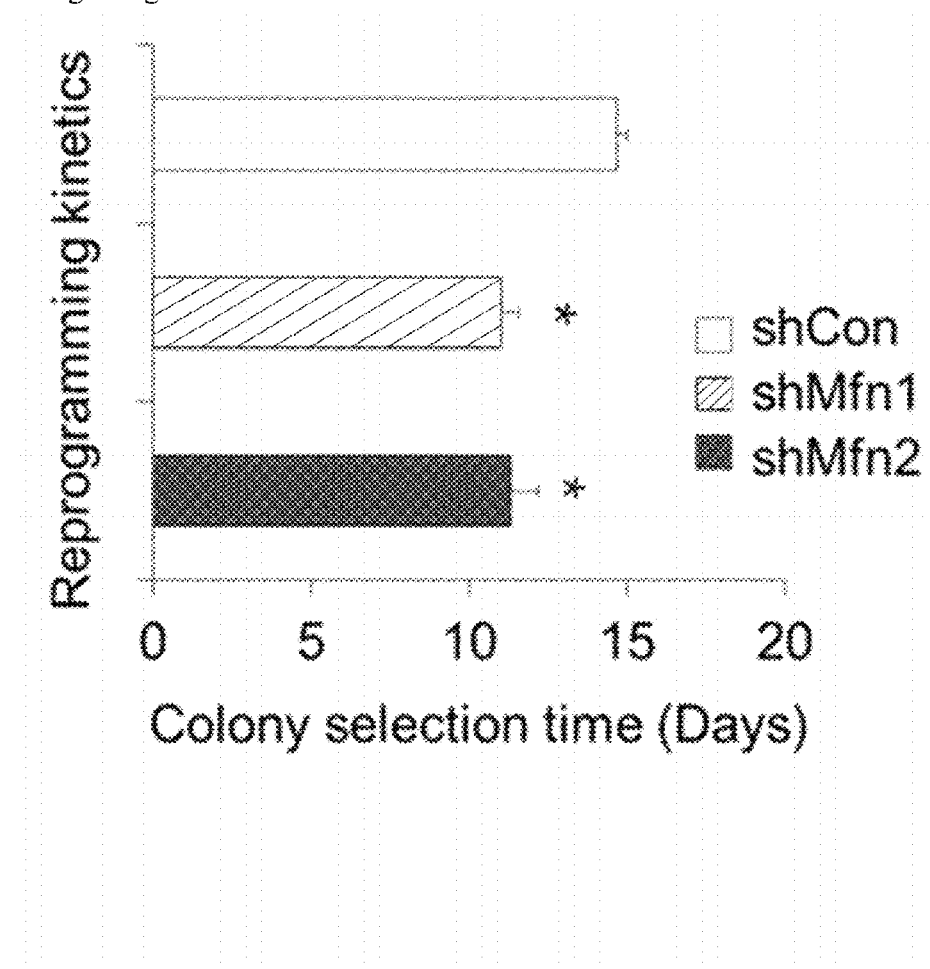
[Figure 6g]

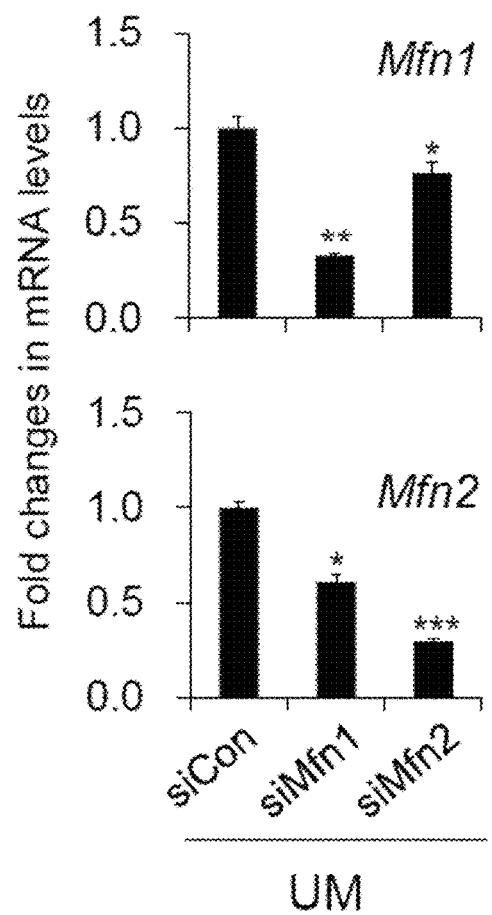
[Figure 7]

[Figure 8a]
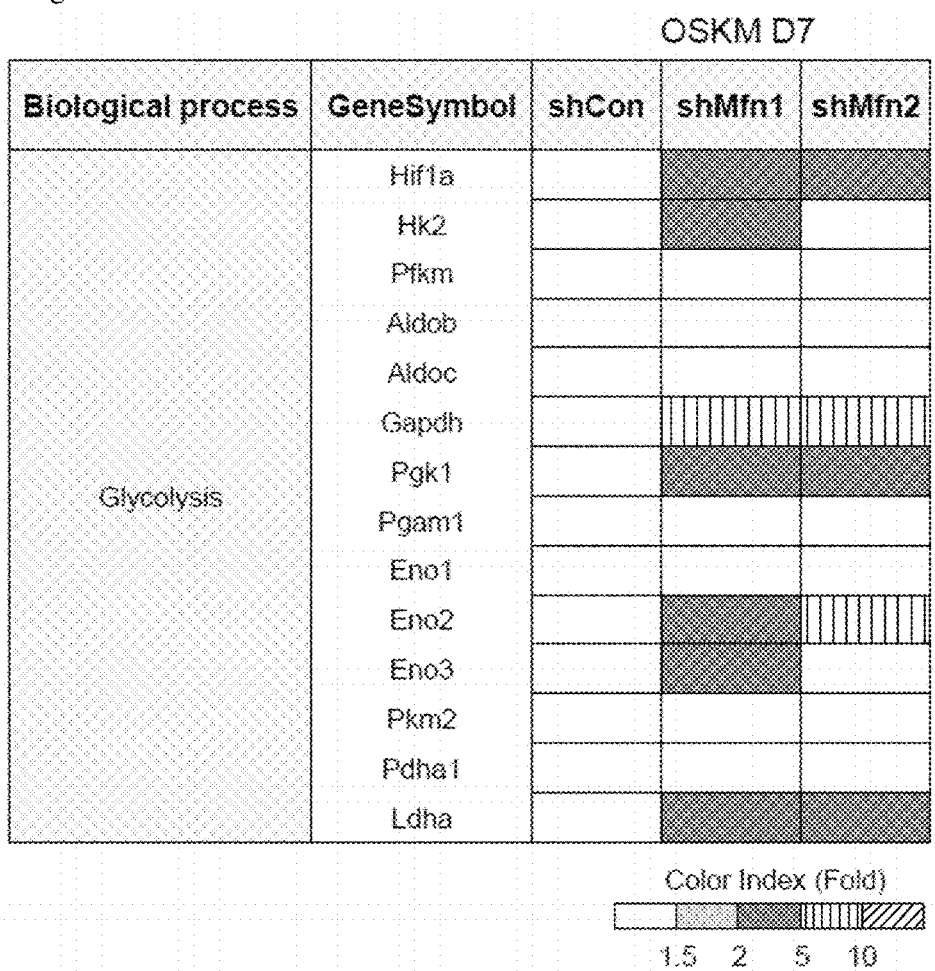

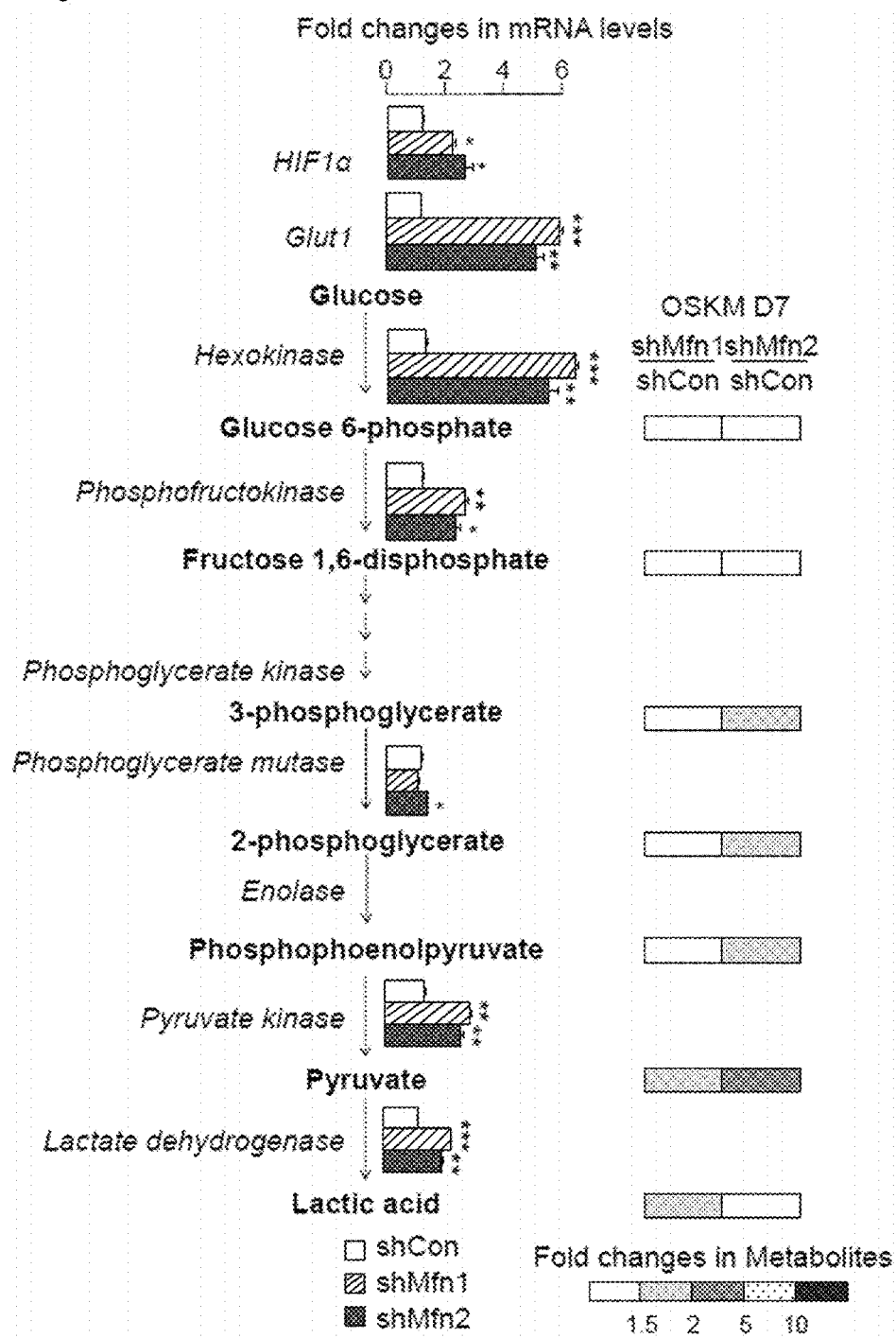
[Figure 8b]

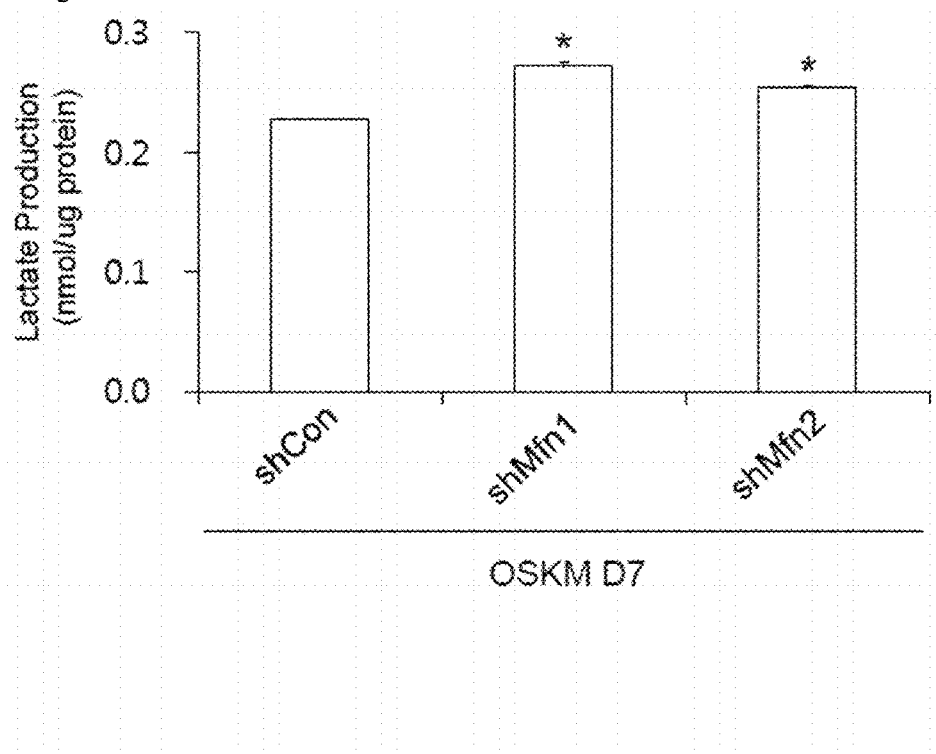

[Figure 9a]
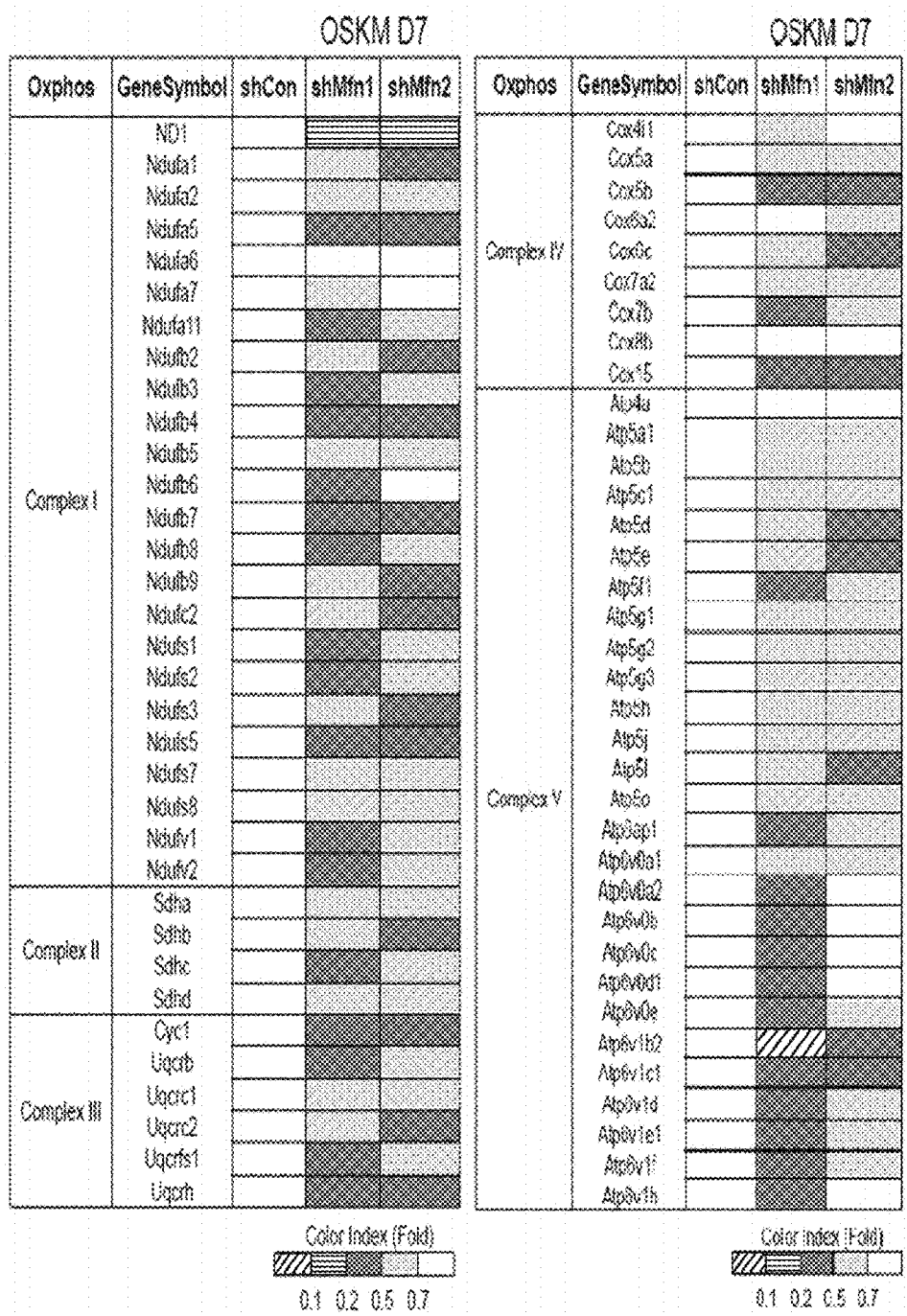

[Figure 9b]
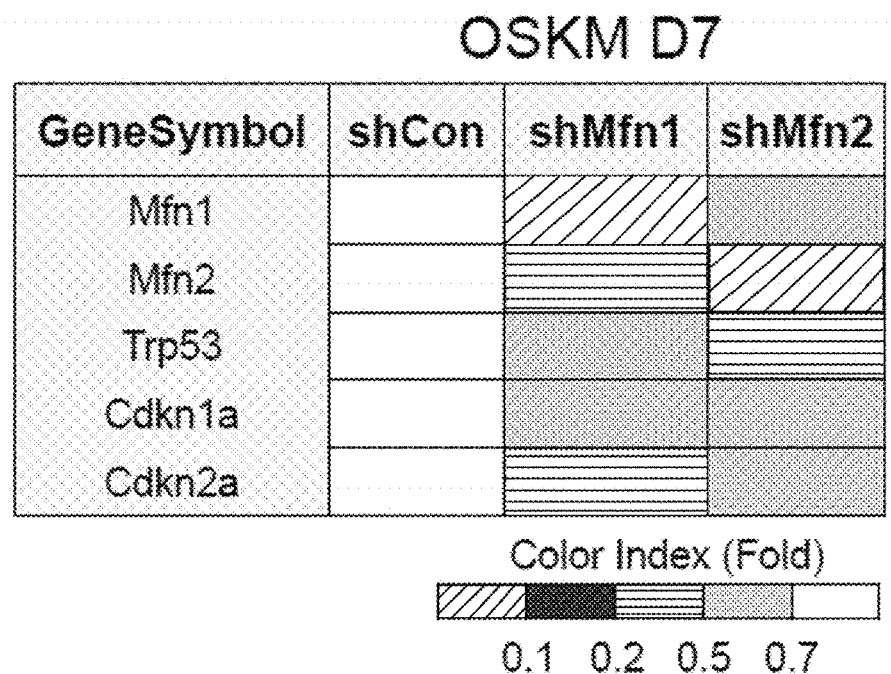

[Figure 9c]
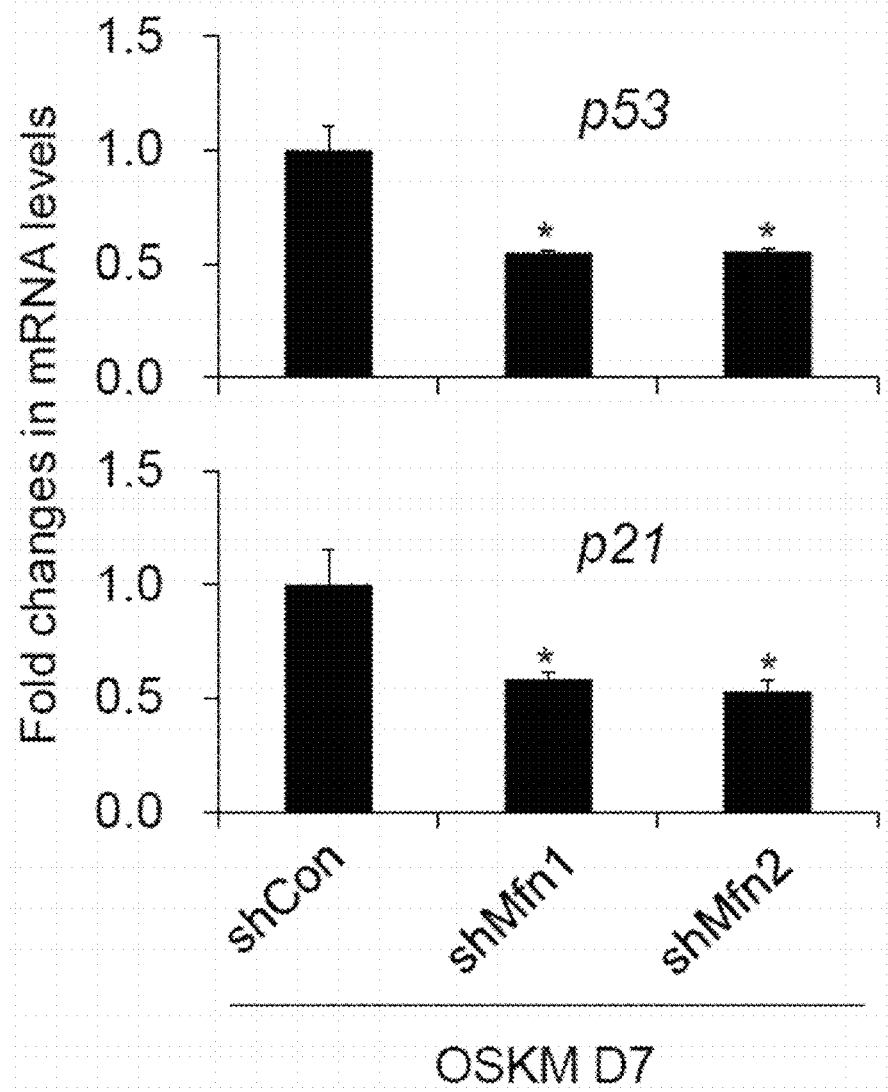
[Figure 10a]
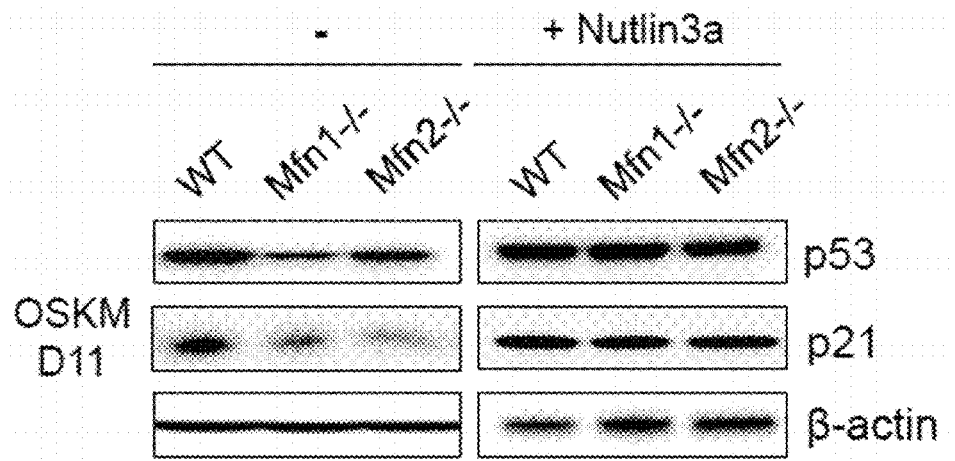

[Figure 10b]
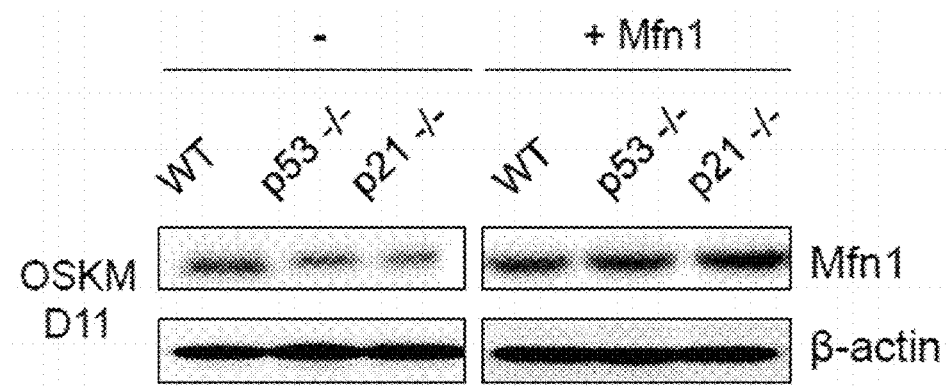
[Figure 10c]
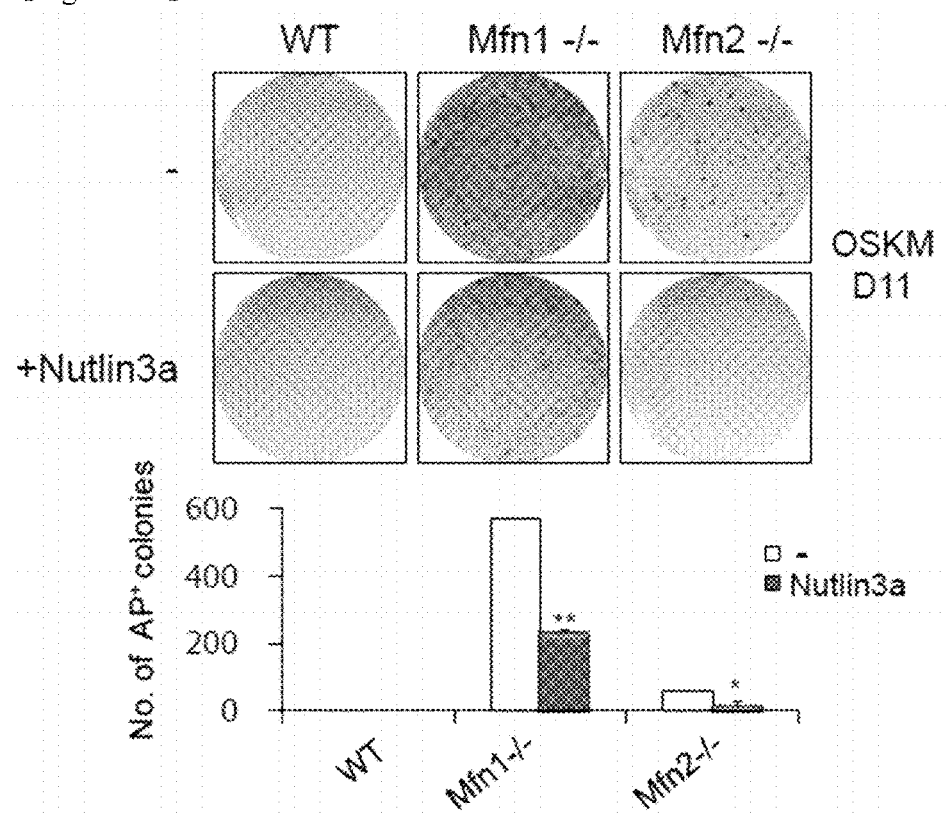

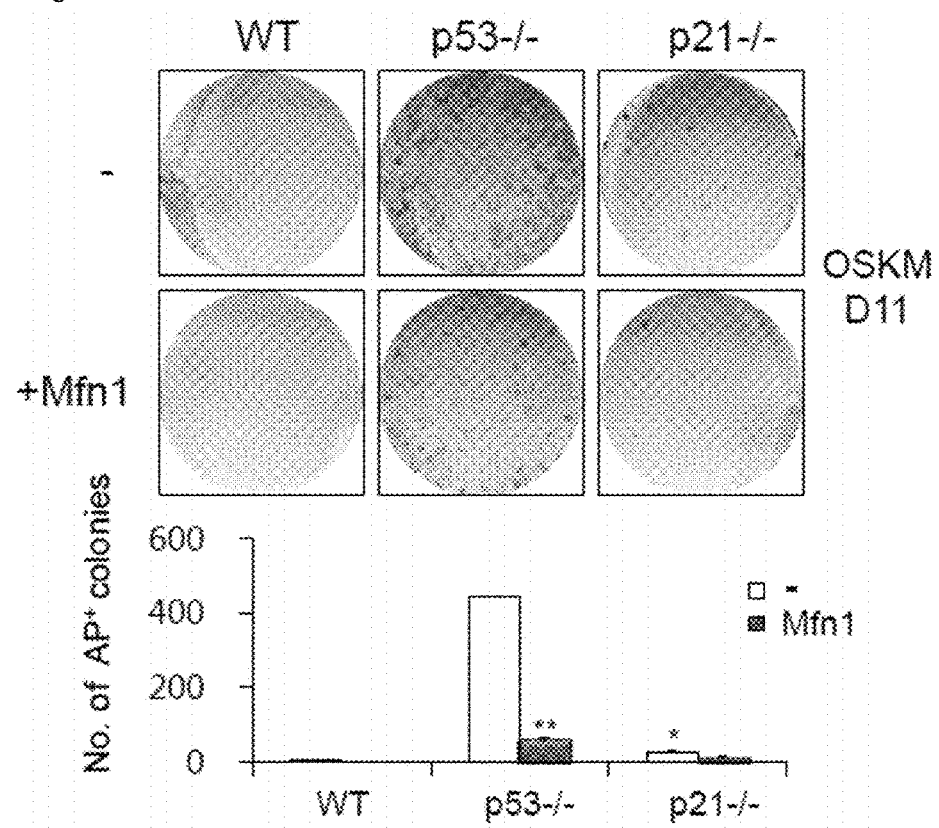
[Figure 10d]

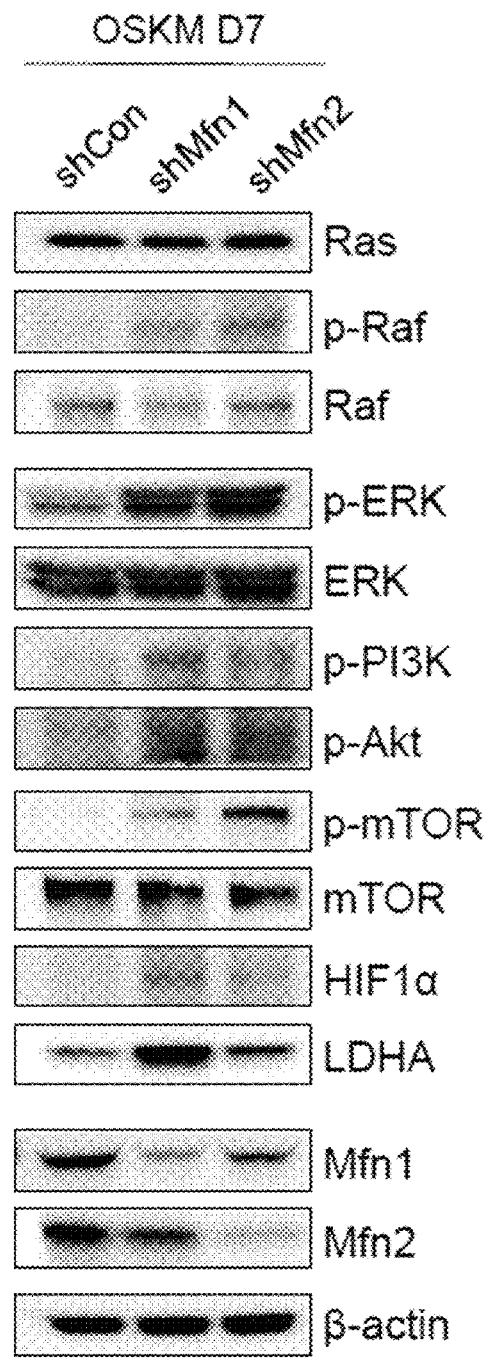

【Figure 10f】
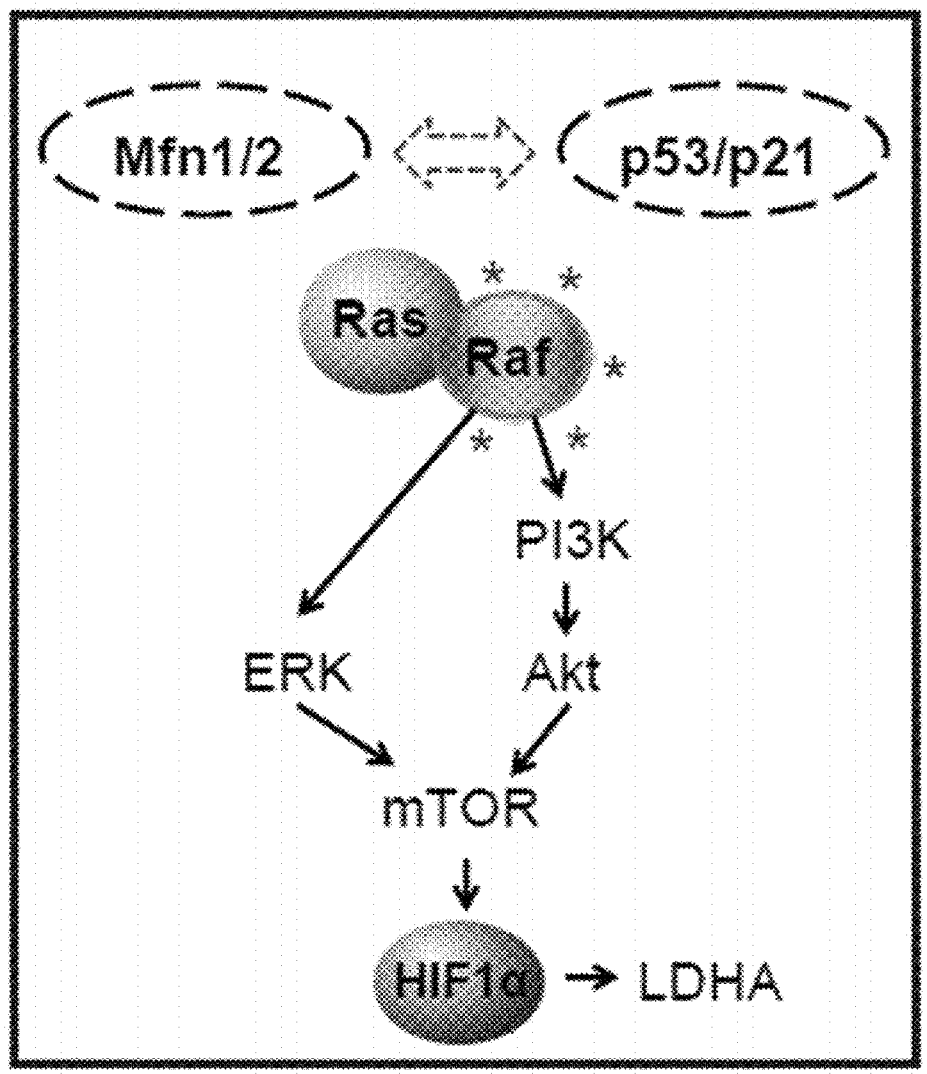
【Figure 11a】
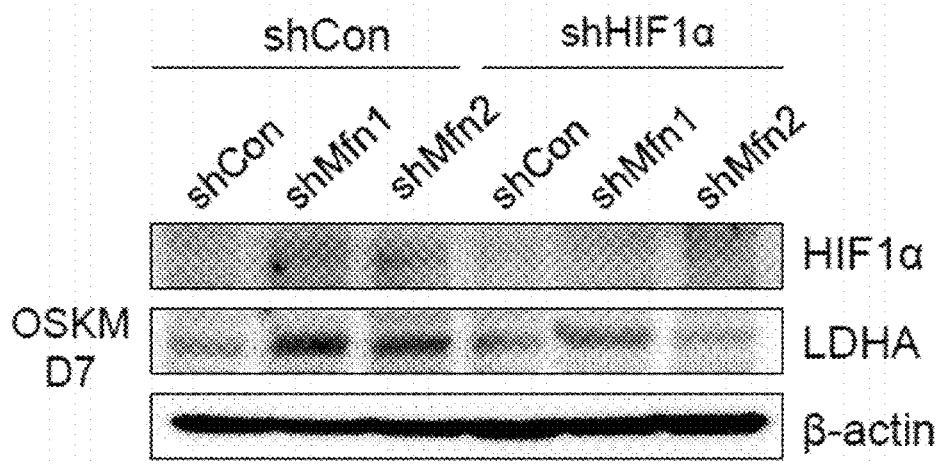

[Figure 11b]
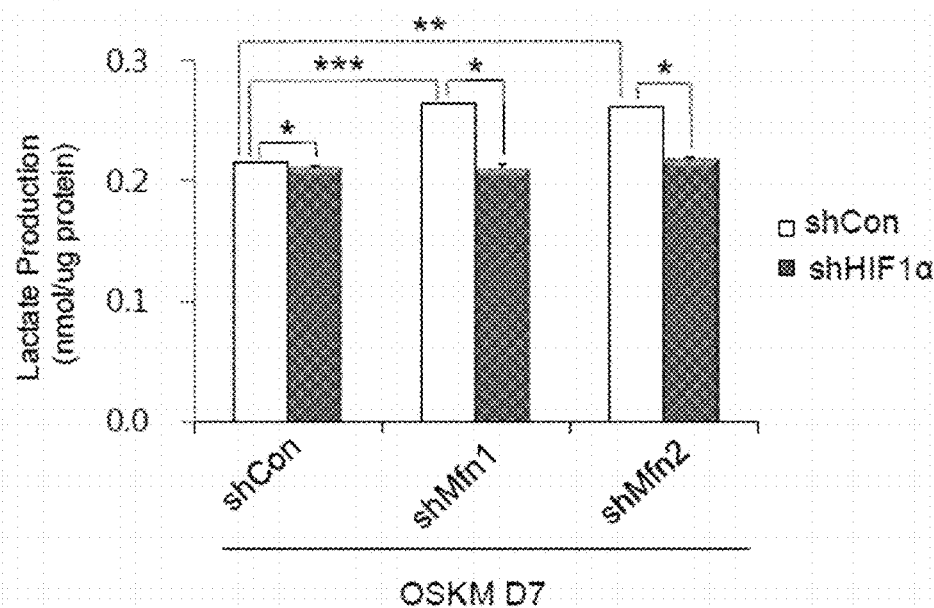
[Figure 11c]
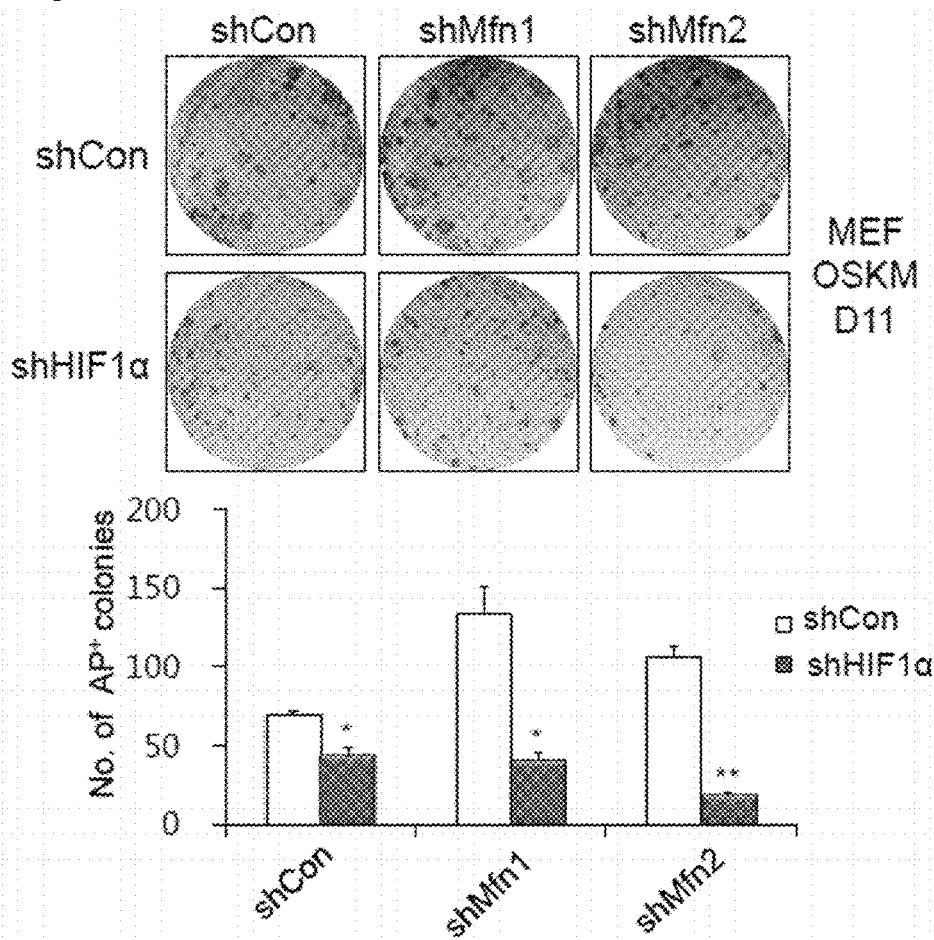

[Figure 12a]
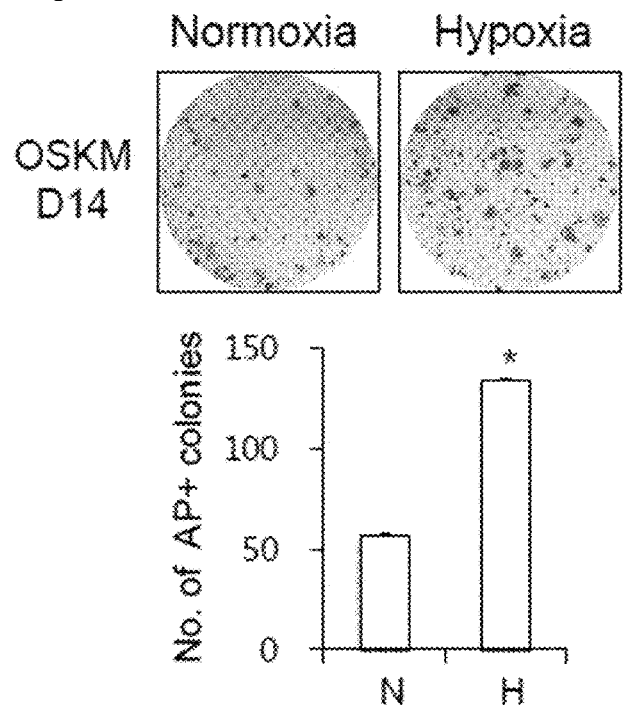
[Figure 12b]
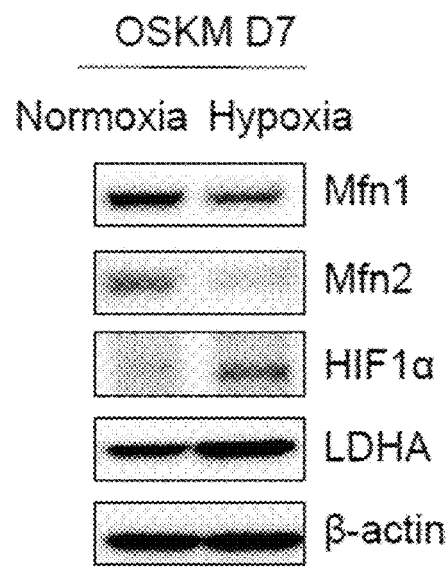

[Figure 12c]
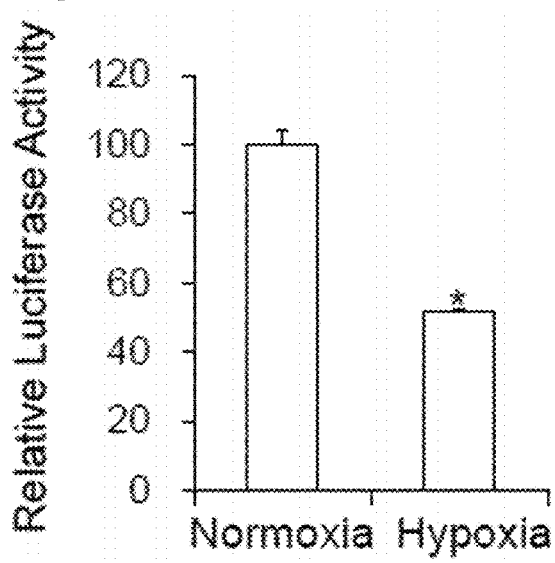
[Figure 12d]
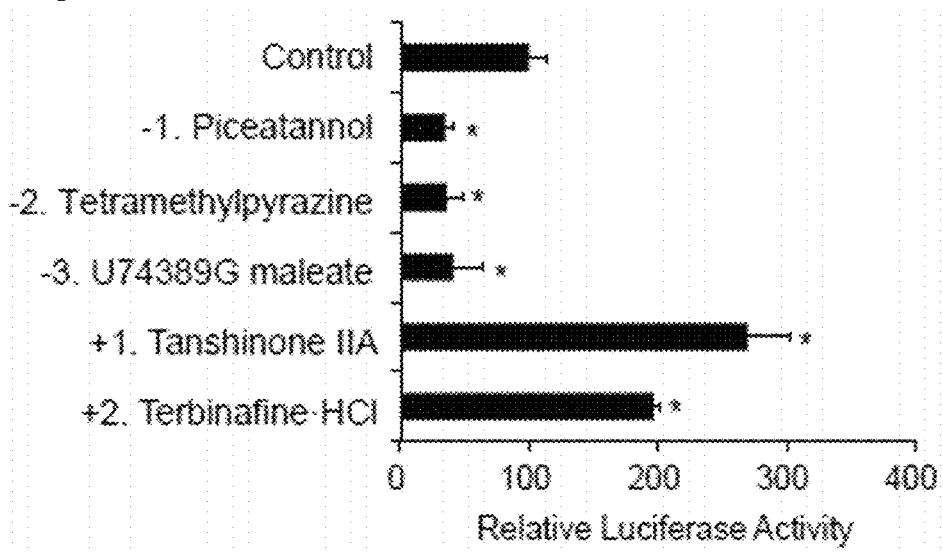
[Figure 12e]
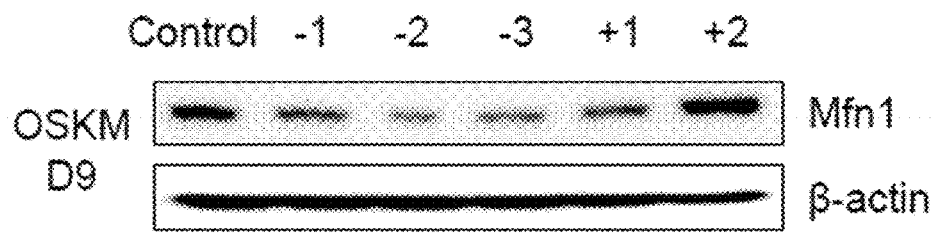

[Figure 12f]
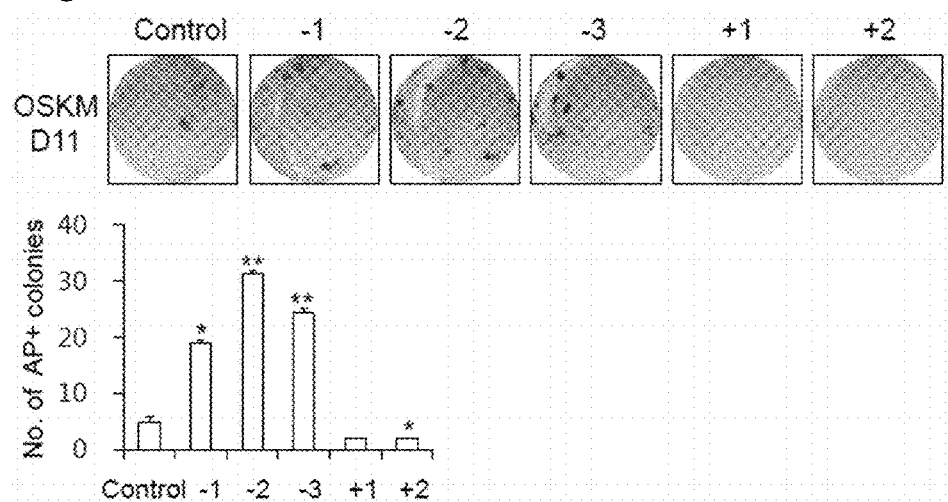
[Figure 12g]
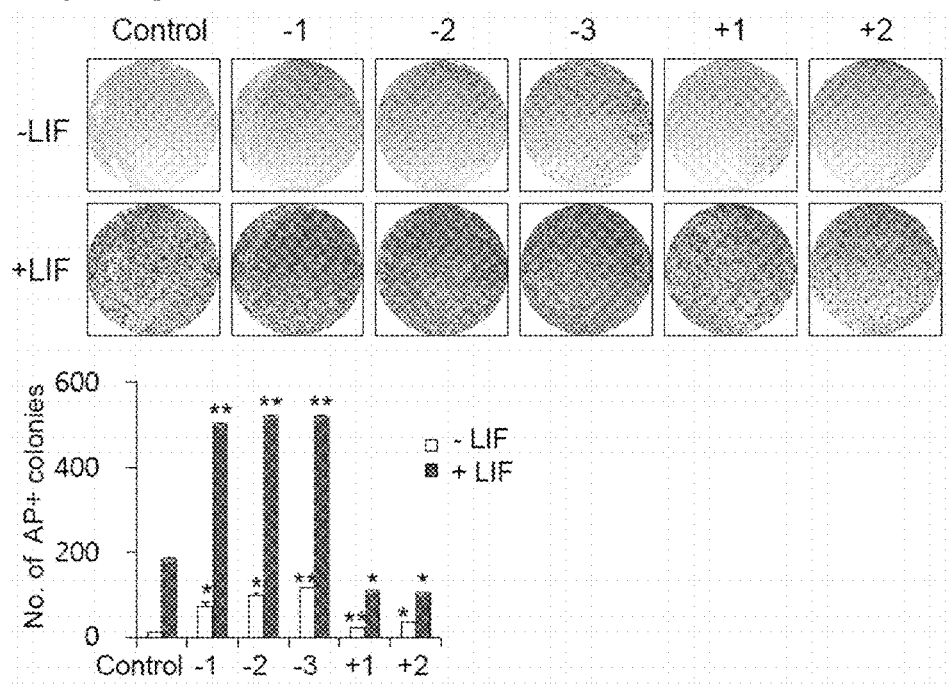

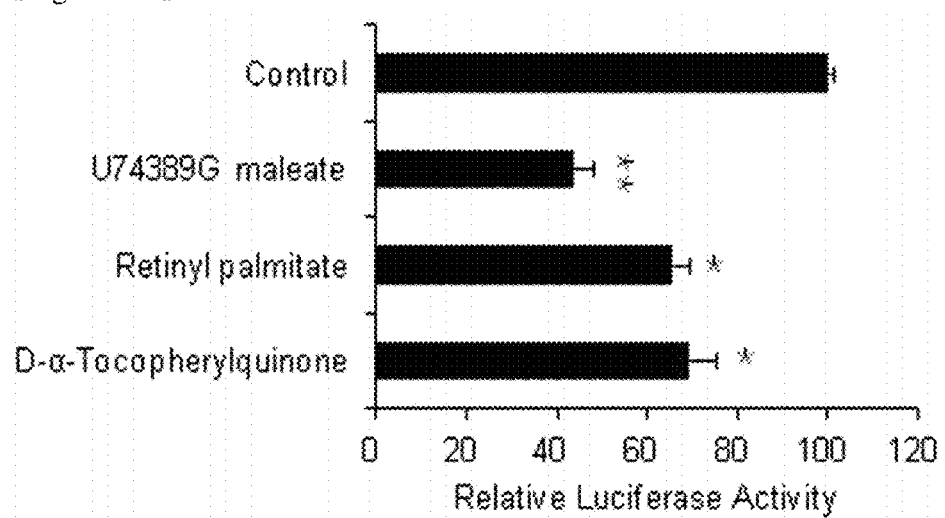
[Figure 12h]

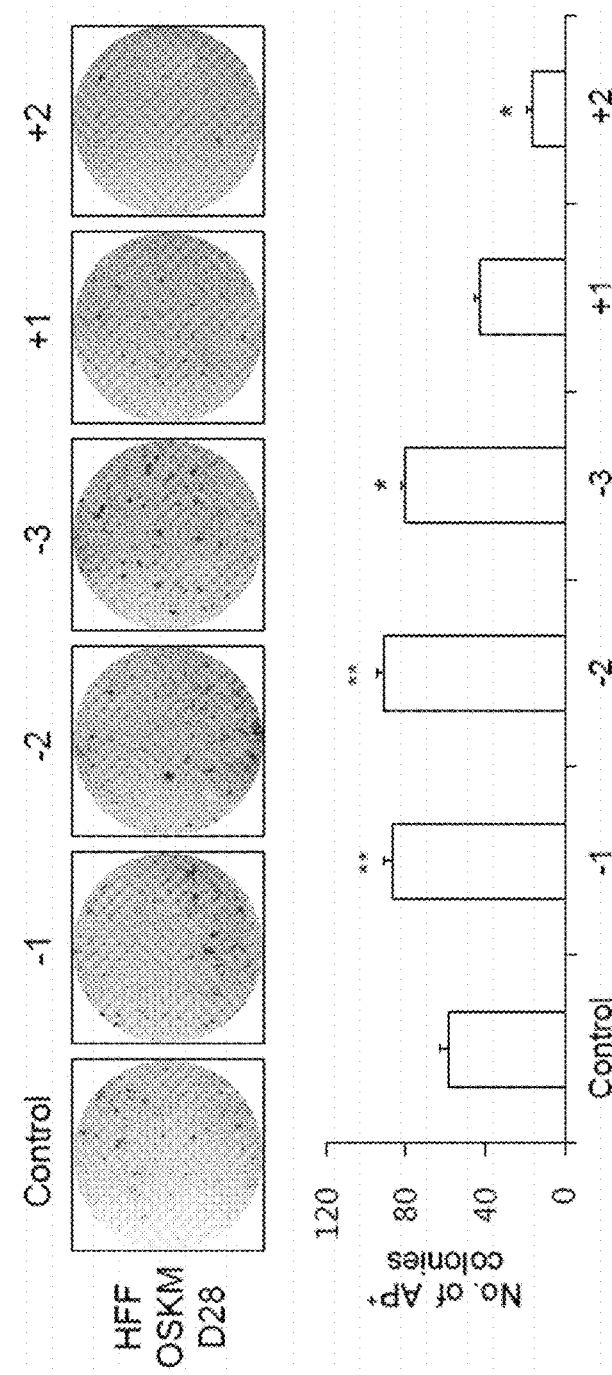
[Figure 13a]

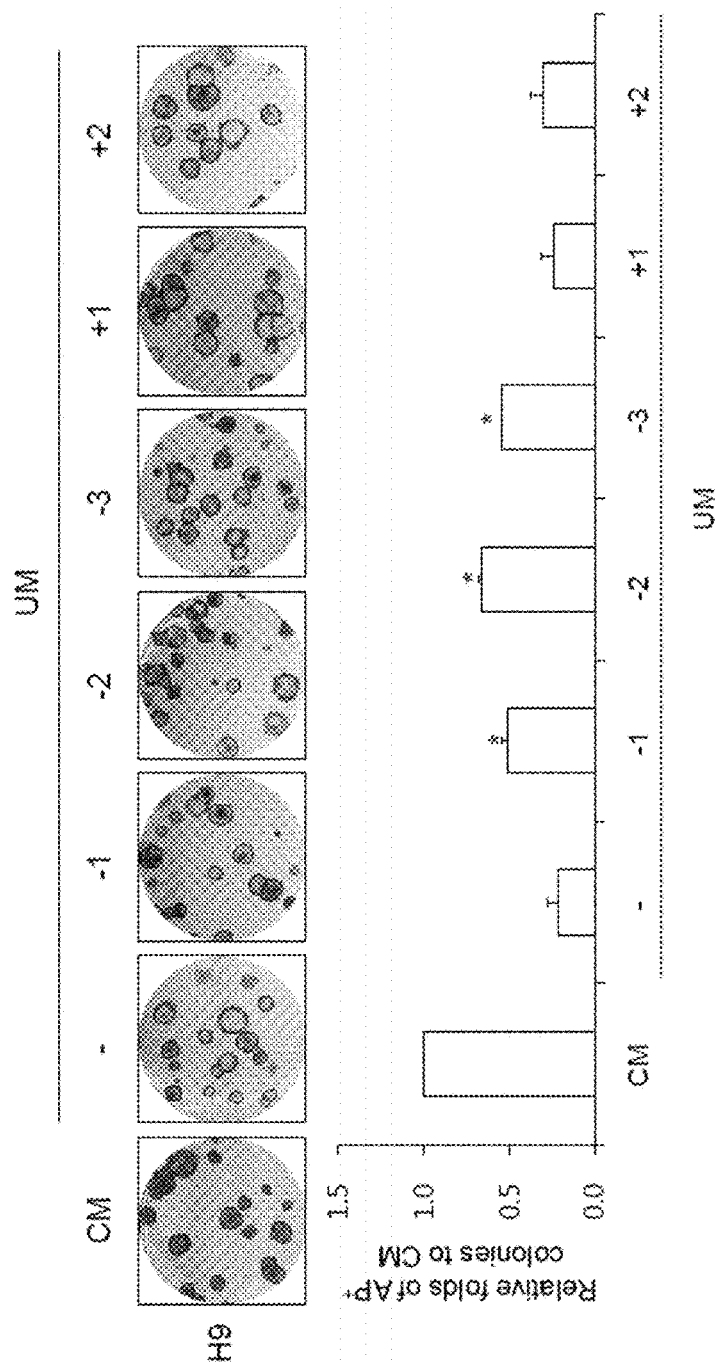
[Figure 13b]

[Figure 14]
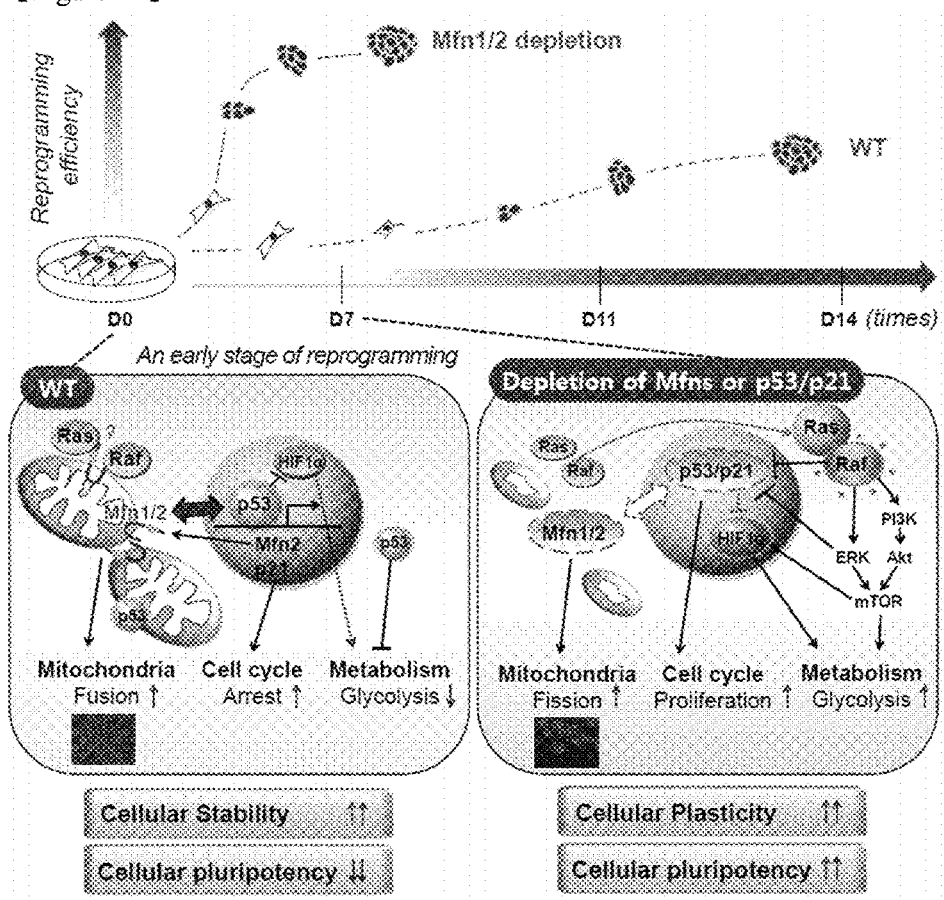

COMPOSITIONS COMPRISING A MITOFUSIN INHIBITOR FOR PROMOTING CELL REPROGRAMMING AND A USE THEREOF

RELATED APPLICATIONS

This application is a 35 U.S.C. § 371 filing of International Application No. PCT/KR2015/004067, filed Apr. 23, 2015, which claims priority to Korean Patent Application No. 10-2014-0162801, filed Nov. 20, 2014, each of which is incorporated herein by reference in its entirety.

TECHNICAL FIELD

The present invention relates to a composition comprising a repressor of mitofusin gene expression, an inhibitor of mitofusin protein activity, or a mixture thereof as an active ingredient for promoting dedifferentiation/reprogramming a differentiated cell into a pluripotent stem cell; a method for producing pluripotent stem cell reprogrammed from differentiated cell using the composition; a pluripotent stem cell produced by the method; a method for reprogramming pluripotent stem cell comprising repressing the expression of mitofusin gene or inhibiting the activity of mitofusin protein; and a pluripotent stem cell produced by the reprogramming method.

BACKGROUND ART

Cell fate transition occurs under various developmental, physiological, and pathological conditions, including normal embryonic development, aging, and tissue regeneration as well as tumor initiation and progression. Defining the cellular and molecular mechanisms of cell fate transition and regulating these mechanisms may be an essential strategy for treating abnormal pathological conditions resulting from improper cell fate control. The recent development of induced pluripotent stem cell (iPSC) technology used to reprogram somatic cells into pluripotent stem cells using defined pluripotency factors allows us to more closely mimic and recapitualte the conditions of cell fate transition (see Takahashi K, et al., Cell, 2006, 126(4), 663-676).

Generally, complex molecular changes at genetic, epigenetic, and metabolic levels have occurred concurrently or sequentially during the stage of somatic cell reprogramming. Cell reprogramming faces the challenge of balancing stability and plasticity and must overcome critical barriers, such as cell cycle checkpoints, the mesenchymal-epithelial transition (MET), and metabolic reprogramming, to progress cell fate conversion from a stochastic early phase toward pluripotency (see Buganim Y, et al., Cell, 2012, 150(6), 1209-1222).

The p53 pathway limits cell fate transition by inducing classical signaling leading to cell cycle arrest, senescence, or apoptosis to protect genome stability against reprogramming-induced stress, and compromised p53 signaling accelerates the reprogramming process. Moreover, p53 governs the homeostasis of the cellular state, which constrains MET by repressing the Klf4-mediated expression of epithelial genes early in the reprogramming process, and which opposes glycolytic metabolic reprogramming.

Balancing mitochondrial dynamics is crucial for maintaining cellular homeostasis, and abnormal mitochondrial dynamics results in numerous diseases. Highly proliferative cells, such as iPSCs and tumor cells, prefer to undergo glycolysis and decrease the dependency on mitochondrial ATP production, which requires supporting the biosynthesis of macromolecules and alleviating mitochondrial oxidative stress in rapidly growing cells.

DISCLOSURE

Technical Problem

The present inventors have conducted extensive and intensive researches in order to improve the methodology for increasing the reprogramming efficiency in the process of reprogramming to pluripotent stem cells. As a result, the inventors have discovered that p53-deficient and p21-deficient cells with high reprogramming efficiency express mitofusin 1 and 2 at a low level, repressing or genetically ablating the mitofusin drastically increases the efficiency of reprogramming a differentiated cell into a pluripotent stem cell and are beneficial for maintaining a pluripotent state of pluripotent stem cells. Further, the inventors have discovered that compounds that repress the activity of mitofusin promoter increase the efficiency of reprogramming and are effective in maintaining the pluripotency. The present invention has been completed on the basis of such discovery.

Technical Solution

An object of the present invention is to provide a composition comprising a repressor of mitofusin gene expression, an inhibitor of mitofusin protein activity, or a mixture thereof as an active ingredient for promoting dedifferentiation/reprogramming a differentiated cell into a pluripotent stem cell.

Another object of the present invention is to provide a medium composition comprising a repressor of mitofusin gene expression, an inhibitor of mitofusin protein activity, or a mixture thereof as an active ingredient for maintaining and culturing pluripotent stem cells in an undifferentiated state.

Yet another object of the invention is to provide a method for a producing pluripotent stem cell reprogrammed from a differentiated cell, comprising (a) delivering at least one reprogramming factor to a differentiated cell, and (b) culturing the differentiated cell in a medium containing the composition for promoting the reprogramming.

A further object of the present invention is to provide a pluripotent stem cell prepared by the above-described method.

A further object of the present invention is to provide a method for reprogramming an isolated differentiated cell into a pluripotent stem cell comprising repressing the expression of mitofusin gene or inhibiting an activity of mitofusin protein of the isolated differentiated cell.

A further object of the present invention is to provide a pluripotent stem cell produced by the reprogramming method.

A further object of the present invention is to provide a use of a repressor of mitofusin gene expression, an inhibitor of mitofusin protein activity, or a mixture thereof for producing a composition for promoting the reprogramming into pluripotent stem cells.

Advantageous Effects

The composition according to the present invention increases the efficiency of reprogramming as well as shortens the time required for reprogramming to produce pluripotent stem cells. Therefore, the present composition can be beneficially used to develop a production technology of high efficiency pluripotent stem cell and a secured large-scale culture system. Further, the present composition can be beneficially used to maintain pluripotent stem cells and to screen for the compounds capable of promoting the reprogramming into pluripotent stem cells.

DESCRIPTION OF DRAWINGS

FIGS. 1a-1f show that mitochondrial function is downregulated during the early-stage reprogramming of p53-KO (p53−/−) and p21-KO(p21−/−) somatic cells. The data is presented as the mean±SE (n=3). *p<0.05; **p<0.01 (Student's t-test).

FIG. 1a shows representative images of AP+ colonies after WT MEFs, p53−/−MEFs, and p21−/− MEFs were reprogrammed via retroviral transduction of the OSKM reprogramming factors. The number of AP+ colonies (top) and the number of AP+ colonies (bottom) were determined on day 11 (D11) of reprogramming.

FIG. 1b shows the stages of sample preparation for transcriptome and metabolome analyses.

FIG. 1c shows a representative cell morphology on D7 of reprogramming (Scale bar=50 μm).

FIG. 1d shows that the expression of genes encoding major enzymes (left) and the relative quantities of each metabolite (right) related to glycolysis were determined through a real-time polymerase chain reaction (PCR) analysis and capillary electrophoresis time-of-flight mass spectrometry (CE-TOFMS), respectively. The fold changes of metabolites in p53−/− and p21−/− reprogramming cultures compared with the WT control at D7 are represented by a color-coded index bar.

FIG. 1e shows the results of transcriptome analysis of mitochondrial function in OSKM-transduced WT, p53−/−, and p21−/− MEFs on D7 of reprogramming.

FIG. 1f shows the results of a real-time PCR of the mitochondria-encoded oxidative phosphorylation (OXPHOS) subunits ND1 and Atp6ap1 and the mitochondrial fusion genes Mitofusin1 (Mfn1) and Mitofusin2 (Mfn2) in WT, p53−/− and p21−/− D7 reprogramming cultures.

FIGS. 2a-c show the results of transcriptome analysis of WT MEFs, p53−/−, and p21−/− MEFs in early-stage reprogramming. The ratios are indicated by a color-coded index bar.

FIG. 2a shows a comparison of marker expression for discriminating reprogramming phases.

FIG. 2b shows a comparison of expression level-upregulated and downregulated gene sets in WT MEFs, p53−/−, and p21−/− MEFs on D7 of reprogramming.

FIG. 2c shows a gene expression analysis of glycolysis in WT MEFs, p53−/− MEFs and p21−/− MEFs at D7 of reprogramming.

FIGS. 3a-3b show that glycolytic conversion is accelerated in p53−/− and p21−/− MEFs in the late stage of reprogramming, which is essential for somatic cell reprogramming. The data are presented as the mean±SE (n=3). *p<0.05; **p<0.01 (Student's t-test)

FIG. 3a shows that lactate production was determined in the cell lysates of each group at the indicated time point of reprogramming.

FIG. 3b shows the effect of the glycolysis inhibitor 2-DG (2-deoxy-D-glucose) on the reprogramming process. Representative images of AP+ colonies (top). The total number of AP+ colonies was counted on D11 (bottom).

FIGS. 4a-4c show that the expression of genes encoding OXPHOS components is downregulated in the early-stage reprogramming of p53−/− and p21−/− MEFs.

FIG. 4a shows gene expression profiling of OXPHOS complex components.

FIG. 4b shows real-time PCR analysis results of the nuclear-encoded OXPHOS subunits Sdhb, Uqcrc1, p53 and p21.

FIG. 4c shows that determination of the ADP/ATP energy turnover rate were performed in WT, p53−/−, and p21−/− reprogramming cultures at D7 and that the data are presented as the mean±SE (n=3). *p<0.05; ***p<0.001 (Student's t-test).

FIGS. 5a-5g show that p53- and p21-KO cells and pluripotent reprogramming intermediates express low levels of mitochondrial fusion proteins.

FIG. 5a shows that OSKM-transduced WT, p53−/−, and p21−/− MEFs on D7 of reprogramming were stained with Tom20 (mitochondria, green) and DAPI (nuclei, blue) (top). High-magnification images (bottom).

FIG. 5b shows a mitochondrial morphology of WT, p53−/−, and p21−/− MEFs stained with Mitotracker (red) and enlarged images (inset in top right corner).

FIG. 5c is a graph showing the cell numbers of WT, p53−/−, and p21−/− MEFs.

FIG. 5d shows the results of Western blot analysis of Cyclin B1 and mitochondrial fission (Drp)-fusion (Mfn) components. β-actin was used as an internal control.

FIG. 5e shows that reprogramming intermediates were sorted based on Thy1 and SSEA1 expression using magnetic-activated cell sorting (MACS) on D11 (scale bar=50 μm). Representative images of each subgroup (top), the mitochondrial morphology stained with Mitotracker (red) (middle), and enlarged images (inset in middle right corner) on D14. The percentages of cells with fragmented/intermediate/fused mitochondria were determined in each subgroup (bottom).

FIG. 5f shows the results of Western blot analysis of mitochondrial fission (Drp)-fusion (Mfn) components in the mitochondrial fraction and of the pluripotency marker Nanog in the whole-cell lysates of MEFs and each subpopulation. HSP60 and β-actin were used as internal controls.

FIG. 5g is schematic presentation of the p53- and p21-KO cells.

FIGS. 6a-6g show that Mfn1 and Mfn2 ablation promotes the acquisition and maintenance of pluripotency. The data are presented as the mean±SE (n=3). *p<0.05; **p<0.01 (Student's t-test).

FIG. 6a shows that MEFs were transduced with control (shCon), Mfn1 (shMfn1) and Mfn2 (shMfn2) lentiviral shRNAs together with retroviral OSKM reprogramming factors and subjected to AP staining. Representative images of AP+ colonies (top) and the numbers of AP+ colonies (bottom) on D11 of reprogramming (bottom) were depicted.

FIG. 6b shows that human foreskin fibroblasts (HFFs) were transduced with control (shCon), Mfn1 (shMfn1) and Mfn2 (shMfn2) lentiviral shRNAs together with retroviral OSKM reprogramming factors and subjected to AP staining. Representative images of AP+ colonies (top) and the numbers of AP+ colonies (bottom) on D28 of reprogramming were depicted.

FIG. 6c shows that H9 hESCs were transfected with control (siCon), Mfn1 (siMfn1) and Mfn2 (siMfn2) siRNAs, cultured with unconditioned medium (UM) and subjected to AP staining. Representative images of AP+ colonies (top) and the relative fold difference in AP+ colonies under feeder-free conditions on D5 (bottom). Conditioned medium (CM)-cultured hESCs were used as an undifferentiated control.

FIG. 6d shows that Western blot analysis of Mfn1 and Mfn 2 and the pluripotency markers Oct3/4 and Nanog in siRNA-transfected hESCs on D5. β-actin was used as an internal control.

FIG. 6e shows that WT, Mfn1−/−, and Mfn2−/− MEFs were reprogrammed via retroviral transduction of OSKM in the absence (top) and presence (middle) of 50 μM Mdivi1, an inhibitor of mitochondrial division. Representative images of AP+ colonies (top and middle) and the numbers of AP+ colonies on D11 of reprogramming (bottom) were depicted.

FIG. 6f shows that the mitochondrial morphology of each reprogramming culture was observed using stably expressed Mito-EYFP (green) on D7. Enlarged images (inset in right corner). Scale bar=50 μm.

FIG. 6g is a graph showing the time required for the reprogramming, when MEFs were transduced with control (shCon), Mfn1 (shMfn1) and Mfn2 (shMfn2) lentiviral shRNAs together with retroviral OSKM reprogramming factors and subjected to reprogramming.

FIG. 7. Knockdown of Mfn 1 and Mfn2 expression via siRNA transfection in hESCs. Real-time PCR analysis of Mfn1 and Mfn2 in Mfn 1 and 2 siRNA-transfected hESCs cultured using UM on D5. The data are presented as the mean±SE (n=3). *p<0.05; p<0.01; *p<0.001 (Student's t-test).

FIGS. 8a-8c show that Mfn 1 and Mfn2 knockdown facilitates glycolytic conversion in early-stage reprogramming.

FIG. 8a shows transcriptome analysis result of gene sets related to glycolysis in MEFs transduced with OSKM and shRNAs on D7 of reprogramming. The ratios are indicated by a color-coded index bar.

FIG. 8b shows that the expression of genes encoding major enzymes (left) and the relative quantity of each metabolite (right) related to glycolysis were determined via real-time PCR analysis and CE-TOFMS, respectively. The fold changes of metabolites in Mfn 1 and Mfn2 shRNA-transduced reprogramming cultures compared with the control at D7 are represented by a color-coded index bar.

FIG. 8c shows that lactate production was determined in the cell lysates of each group. The data are presented as the mean±SE (n=3). *p<0.05; **p<0.01 (Student's t-test).

FIGS. 9a-9c show gene expression profiling of OXPHOS complex components and cell cycle regulators following Mfn 1 and Mfn2 knockdown during early reprogramming.

FIG. 9a shows the results of transcriptome analysis of OXPHOS complex components in MEFs transduced with OSKM and the indicated shRNAs on D7 of reprogramming.

FIG. 9b shows transcriptome analysis results of Mfn 1 and Mfn2, p53 (Trp53), p21 (Cdkn1a), and p16 (Cdkn2a) in MEFs transduced with OSKM and the indicated shRNAs on D7 of reprogramming.

FIG. 9c shows transcriptome analysis results of real-time PCR analysis of p53 and p21 in MEFs transduced with OSKM and the indicated shRNAs on D7 of reprogramming. The data are presented as the mean±SE (n=3). *p<0.05 (Student's t-test).

FIGS. 10a-10f show that reciprocal inhibition of p53/p21 and Mfn1/2 activates the Ras-Raf-HIF1α pathway. β-actin was used as an internal control. The data are presented as the mean±SE (n=3). *p<0.05; **p<0.01 (Student's t-test).

FIG. 10a shows Western blot analysis results of p53 and p21 on D11 of reprogramming, after WT, Mfn1−/−, and Mfn2−/− MEFs were reprogrammed via retroviral transduction of OSKM in the absence and presence of 25 μM Nutlin3a, an MDM2 inhibitor that stabilizes p53.

FIG. 10b shows the results of Western blot analysis of Mfn1 on D11 of reprogramming, after WT, p53−/−, and p21−/− MEFs were reprogrammed via retroviral transduction of OSKM with or without retroviral Mfn1 overexpression.

FIG. 10c shows that images of AP+ colonies (top and middle) and the total numbers of AP+ colonies (bottom) were obtained in each indicated group.

FIG. 10d shows that images of AP+ colonies (top and middle) and the total numbers of AP+ colonies (bottom) were obtained in each indicated group.

FIG. 10e shows Western blot analysis results of Ras-Raf signaling in MEFs transduced with OSKM and Mfn1 and Mfn2 shRNAs on D7 of reprogramming.

FIG. 10f is model showing the activation of Ras-Raf-HIF1α signaling in Mfn1/2 depleted cells.

FIGS. 11a-11c show that increased glycolysis and reprogramming by Mfn1 and Mfn2 knockdown is HIF1α-dependent. The data are presented as the mean±SE (n=3). *p<0.05; p<0.01; *p<0.001 (Student's t-test).

FIG. 11a shows that MEFs were transduced with OSKM and the indicated shRNAs. Western blot analysis was performed on D7 of reprogramming. β-actin was used as an internal control.

FIG. 11b shows that lactate production was determined in the cell lysates of each group.

FIG. 11c shows that images of AP+ colonies (top and middle) and the total numbers of AP+ colonies (bottom) were obtained in each indicated group.

FIGS. 12a-12h show that hypoxia decreases Mfn1 and Mfn2 expression, and chemicals that inhibit Mfn1 expression promote the acquisition and maintenance of stem cell fate. β-actin was used as an internal control. The data are presented as the mean±SE (n=3). *p<0.05; p<0.01; *p<0.001 (Student's t-test).

FIG. 12a shows that MEFs were reprogrammed via the retroviral transduction of OSKM under normoxia (N) and hypoxia (H, 5% O2). Images of AP+ colonies (top) and the number of AP+ colonies (bottom) were counted on D11.

FIG. 12b shows Western blot analysis results of Mfn1 and Mfn2, HIF1α and LDHA on D7 of reprogramming in cultures under normoxia and hypoxia.

FIG. 12c shows Mfn1 promoter activity, determined in Mfn1−/− MEFs stably expressing an Mfn1 promoter reporter construct after 48 hours of normoxic or hypoxic culture.

FIG. 12d shows relative luciferase activity, determined in Mfn1−/− MEFs carrying the Mfn1 promoter reporter, at 48 hours after treatment with 84 redox library compounds. The top 3 downregulated (−1, −2, and −3) and the top 2 upregulated (+1 and +2) hits controlling Mfn1 promoter activity are presented.

FIG. 12e shows that MEFs were reprogrammed via retroviral transduction of OSKM together with treatment with 1 μM of selected compounds, and Mfn1 protein expression was determined on D9 of reprogramming by Western blot analysis.

FIG. 12f shows that images of AP+ colonies were obtained (left) and the number of AP+ colonies was counted (right) on D11 of reprogramming under treatment with 1 μM of selected compounds.

FIG. 12g shows that J1 mESCs were cultured with (+; self-renewing condition, bottom left) or without LIF (−; non self-renewing condition, top left). Images of AP+ colonies were obtained (left) and the number of AP+ colonies was counted (right) on D5 under treatment with 1 μM of selected compounds.

FIG. 12h; 293T cells (human embryonic renal cells) including human Mfn1 promoter reporter were treated with 10 μM of 84 focused redox library compounds. After 48 hours, the relative luciferase activity was measured and the results are shown in the graph.

FIGS. 13a-13b show that Mfn1 promoter activity-repressing compounds are beneficial for acquisition and maintenance of stem cell fate. The data are presented as the mean±SE (n=3). *p<0.05 (Student's t-test).

FIG. 13a shows that HFFs were transduced with retroviral OSKM reprogramming factors and 10 μM of Mfn1 promoter activity-regulating compounds were treated during reprogramming. Images of AP+ colonies (top) and the numbers of AP+ colonies (bottom) were determined on D28 of reprogramming.

FIG. 13b shows that H9 hESCs were cultured with UM to provide differentiation conditions, and treatment with 10 μM of Mfn1 promoter activity-regulating compounds was performed in the presence of UM. Images of AP+ colonies (top) and the relative fold difference in AP+ colonies under feeder-free conditions on D5 (bottom). CM-cultured hESCs were used as an undifferentiated control.

FIG. 14 is a model for the control of cellular stability and plasticity via the reciprocal interaction of the p53/p21 and Mfn1/2 pathways. Depletion of Mfn1/2 promoted somatic cell reprogramming (top), which increases plasticity, allowing reprogramming barriers, such as mitochondrial fusion, cell cycle arrest, and/or failure of metabolic reprogramming, to be overcome (bottom).

BEST MODE

In one aspect, the present invention provides a composition comprising a mitofusin inhibitor as an active ingredient for promoting reprogramming differentiated cells into pluripotent stem cells. Specifically, the present invention provides a composition comprising a repressor of mitofusin gene expression, an inhibitor of mitofusin protein activity, or a mixture thereof as an active ingredient for promoting reprogramming differentiated cells into pluripotent stem cells.

In the present invention, the term "mitofusin" refers to a class of GTP-binding proteins embedded in the outer membrane of the mitochondria, which is a structural protein leading to a bond between mitochondria. Specifically, the mitofusin may be derived from a mouse or human, but is not limited thereto. Also, the mitofusin may specifically be mitofusin 1 (Mfn1) or mitofusin 2 (Mfn2). More specifically, the mitofusin may be Mfn1 having an amino acid sequence of SEQ ID NO: 1 (mouse-derived) or SEQ ID NO: 3 (human-derived) or Mfn2 having an amino acid sequence of SEQ ID NO: 2 (mouse-derived) or SEQ ID: 4 (human-derived). Even more specifically, the mitofusin may be Mfn1 encoded with a base sequence which can be amplified with a primer of SEQ ID NO: 21 or 22, or Mfn2 encoded with a base sequence which can be amplified with a primer of SEQ ID NO: 23 or 24, but is not limited thereto. The present inventors were the first to identify that, if mitofusin is repressed or genetically ablated from a differentiated cell, the efficiency of reprogramming to pluripotent stem cell is significantly increased and the pluripotency is maintained.

Based on such sequences of Mfn1 and Mfn2, a gene expression repressor of Mfn1 and 2 and an inhibitor of protein activity can be designed, and the sequence can be modified to some extent in this design. It will be apparent to those skilled in the art that the sequences capable of maintaining the homology of 80% or more, specifically 90% or more, more specifically 95% or more, and even more specifically 98% or more due to such artificial modification can be used.

In one specific embodiment of the present invention, the analysis was performed through alkaline phosphate (AP) staining to confirm that Mfn1/2 downregulation contributes to somatic cell reprogramming. The results demonstrate that Mfn1 and 2 knockdown using shRNA exhibited a significant increase in the number of reprogrammed cells as compared with the case of using control shRNA in both mouse (FIG. 6a) and human cell system (FIG. 6b). The results also demonstrate that Mfn1 and 2 knockdown using shRNA in mouse shortened the time required for the reprogramming as compared with using shRNA control (FIG. 6g).

In addition, in culture conditions using an unconditioned medium (UM) which is a condition for differentiation, human embryonic stem cells (hESC) led to differentiation, but hESCs with Mfn1 and Mfn2 knockdown using siRNA were maintained in the undifferentiated state (FIG. 6c). Under UM culture conditions, the expression of pluripotency-associated markers such as Oct3/4 and Nanog was maintained well in hESCs upon knockdown of Mfn1 and Mfn2 (FIGS. 6d and 7).

Furthermore, complete knockout via the genetic ablation of Mfn1 and Mfn2 yielded a significantly higher reprogramming efficiency (FIG. 6e) and a fragmented mitochondrial morphology (FIG. 6f) compared with WT mouse embryonic fibroblasts (MEFs). In particular, Mfn1−/−(Mfn1-KO) exhibited a significant increase of about 500 times or more in the numbers of AP+ colonies and Mfn2−/−(Mfn1-KO) exhibits a significant increase of about 200 times or more in the numbers of AP+ colonies as compared with WT (FIG. 6e). These results confirm that reprogramming efficiency of somatic cells via the ablation of Mfn1 and Mfn2 could be significantly increased. However, it has been found that these effects were blocked by treatment with Mdivi1, a pharmacological inhibitor of mitochondrial fission (FIGS. 6e and 6f).

These results demonstrate that, when mitochondrial structural protein Mfn is repressed or genetically ablated, the efficiency of reprogramming a differentiated cell into a pluripotent stem cell is significantly increased and the pluripotency is maintained.

In the present invention, the term "repressor of mitofusin gene expression" refers collectively to a substance capable of downregulating the mitofusin expression. More specifically, this repressor may comprise all the substances that downregulate the mitofusin expression at a transcription level or at a protein level. As the substances that repress the mitofusin expression, compounds capable of inhibiting the mitofusin expression or activity, targeting to mitofusin, nucleic acid, polypeptide, virus or vector including the nucleic acid can be used without restriction in their types. Specifically, the repressor of mitofusin gene expression may be at least one selected from the group consisting of an antisense oligonucleotide, siRNA, shRNA, and microRNA of mitofusin gene, but is not limited thereto. In the case of repressing the mitofusin gene expression, the efficiency of reprogramming a differentiated cell into a pluripotent stem cell is significantly increased and the pluripotency is maintained. Accordingly, the repressor of mitofusin gene expression can be used for the purpose of increasing the efficiency of reprogramming to pluripotent stem cells from differentiated cells.

In one specific embodiment of the present invention, the analysis was performed through an alkaline phosphate (AP) staining to confirm that Mfn1/2 downregulation contributes to somatic cell reprogramming. The results confirm that Mfn1 and 2 knockdown using shRNA exhibited a significant increase in the reprogramming efficiency as compared with the case of using control shRNA (FIGS. 6a and 6b) and that hESCs with Mfn1 and 2 knockdown using shRNA was maintained under UM in the undifferentiated state (FIG. 6c). Further, under UM culture conditions, the expression of pluripotency-associated markers such as Oct3/4 and Nanog was maintained well in hESCs upon knockdown of Mfn1 and 2 (FIGS. 6d and 7).

Further specifically, the repressor of mitofusin gene expression can be those which repress mitofusin promoter activity, and examples thereof include at least one selected from the group consisting of piceatannol, tetramethylpyrazine, 21-[4-(2,6-di-1-pyrolidinyl-4-pyrimidinyl)-1-piperazinyl]pregna-1,4,9[11]-triene-3,20-dione maleate, retinyl palmitate and D-α-tocopherylquinone, but the substances which can repress the mitofusin gene expression and reprogram the differentiated cells can be included without limitation.

In the case of repressing the mitofusin promoter activity, the mitofusin gene expression is repressed and so, the efficiency of programming to pluripotent stem cells from differentiated cells is significantly increased and the pluripotency is maintained. Therefore, the repressor of mitofusin promoter activity can be used for the purpose of increasing the efficiency of programming to pluripotent stem cells from differentiated cells.

In one specific embodiment of the present invention, the present inventors have screened chemicals with the aim of altering the promoter activity of mouse or human Mfn1, using 84 focused redox library compounds. As a result, we have identified a new use of the top 3 downregulated compounds (piceatannol, tetramethylpyrazine and 21-[4-(2, 6-di-1-pyrrolidinyl-4-pyrimidinyl)-1-piperazinyl]pregna-1, 4,9[11]-triene-3,20-dione maleate, U74389G maleate), and the top 2 upregulated compounds (Tanshinone IIA, erbinafine.HCl) controlling mouse Mfn1 promoter activity (FIG. 12d). Also, we have identified that compounds that repress mouse Mfn1 promoter activity enhanced the reprogramming efficiency of both mouse and human somatic cells (FIGS. 12f and 13a) and that these compounds were beneficial for the maintenance of both mouse (FIG. 12g) and human ESCs (FIG. 13b) in an undifferentiated state.

In addition, we have identified a new use of the three compounds that best repress human Mfn1 promoter activity (U74389G maleate, retinyl palmitate and D-α-tocopheryl quinone)(FIG. 12h) and that U74389G maleate repressed Mfn1 promoter activity in both mice and human cells.

These results demonstrate that inhibitors of Mfn1 or 2 remarkably facilitate reprogramming a differentiated cell into a pluripotent stem cell and maintain the pluripotency and thus, lead a significant improvement in comparison with a conventional reprogramming condition (FIG. 14).

Further, if the composition for promoting reprogramming of the present invention can promote reprogramming to pluripoent stem cells from differentiated cells, the composition may comprise the repressors of mitofusin expression at various concentrations, but the repressors may comprise in the concentration of specifically 1 nM to 100 μM, and more specifically, 10 nM to 10 μM.

In one specific embodiment of the present invention, mouse and human Mfn1 promoter reporter (Genecopoeia) cells were prepared using Mfn1–/–MEFs and 293T cells, respectively, and a Screen-Well™ REDOX library containing the 84 compounds was treated at a concentration of 10 μM by for 48 hours. As a result, we have confirmed that piceatanol, tetramethyl pyrazine and U74389G maleate down-regulated mouse Mfn1 promoter activity (FIG. 12d) and that U74389G maleate, retinyl palmitate and D-α-tocopheryl quinone down-regulated human Mfn1 promoter activity (FIG. 12h).

These results demonstrate that in the case of treating a repressor of mitofusin promoter activity in the said concentration range, the reprogramming efficiency is markedly increased, which leads to a remarkable improvement as compared with a conventional reprogramming condition.

In the present invention, the term "inhibitor of mitofusin protein activity" refers collectively to a substance which down-regulates the mitofusin protein activity and may specifically be an antibody or aptamer that binds specifically to the protein expressed from mitofusin gene, but is not limited thereto. The antibodies of the present invention include a polyclonal antibody, a monoclonal antibody or a fragment thereof as long as it has an antigen-binding property. Furthermore, the antibodies of the present invention also include special antibodies such as humanized antibodies and human antibodies, and the antibodies already known in the art other than novel antibodies may be included. The above-described antibody includes a complete form having a full length of two heavy chains and two light chains as well as a functional fragment of an antibody molecule, as long as it has the binding properties which specifically recognize the protein expressed by the mitofusin gene. The functional fragment of the antibody molecule refers to a fragment which holds at least antigen-binding function, and examples thereof include Fab, F(ab'), F(ab')2 and Fv and the like, but are not limited thereto.

In the present invention, the term "differentiation" refers to the process by which cells are divided and grown and the structure or function thereof is specialized during which the entire object is growing. In other words, the differentiation refers to a process in which biological cells, tissues or the like are changed into an appropriate form and function to perform respective given role. For example, the differentiation may include the process to which pluripotent stem cells such as embryonic stem cells are changed into ectoderm, mesoderm and endoderm cells, and also hematopoietic stem cells are changed into red blood cells, white blood cells, platelets and the like, that is, the process to which progenitor cells also express a certain differentiated character.

In the present invention, the "differentiated cell" refers to a cell in which the process of differentiation is proceeded to have a certain form and function. The differentiated cell of the present invention is not particularly limited, but comprises a germ cell, a somatic cell or a progenitor cell. One example thereof may be a human-derived cell, but the cells derived from various objects are included within the scope of the present invention.

Also, the differentiated cell of the present invention can comprise all the cells differentiated in vivo or in vitro, and it can be a differentiated cell of animal except for human or a differentiated cell separated in vivo.

The "somatic cell" refers to all cells in which differentiation has been completed constituting animal and plant except for the germ cell. The "progenitor cell" refers to a mother cell which does not express a differentiated character, but has a differentiation fate, if it has been found that a cell corresponding to its progeny expresses a certain differentiation character. For example, as for the nerve cells (neurons), nerve fibroblasts (neuronal stem cells) correspond to the precursor cell. As for the myotube, myoblasts correspond to the precursor cell.

In the present invention the term "pluripotent stem cell" refers to a stem cell in which has a pluripotency capable of differentiating into cells of all tissues of an object and a self-reproduction capability. Examples thereof include an embryonic stem cell and an induced pluripotent stem cell, but are not limited thereto.

The pluripotent stem cell of the present invention may comprise all of the pluripotent cells derived from humans, monkeys, pigs, horses, cattle, sheep, dogs, cats, mice, rabbits and the like, and the human-derived pluripotent stem cell is preferred.

The "induced pluripotent stem cell (iPSC)" refers to cells derived to have a pluripotency via an artificial reprogramming process from differentiated cells. The artificial reprogramming process is performed by introducing virus-mediated reprogramming factor using a retrovirus and lentivirus or non-viral-mediated reprogramming factor using a non-viral vector, protein and a cellular extract, or it may include the reprogramming process by stem cell extracts, compounds and the like. The induced pluripotent stem cells have almost the same properties as those of embryonic stem cells. Specifically, the cells show a similar shape, which show similar gene and protein expression patterns, they have pluripotency in vitro and in vivo, and they form a teratoma. When these cells are inserted into blastocysts, a chimeric mouse may be formed. In addition, a germline transmission of a gene is possible. The induced pluripotent stem cell of the present invention may comprise all of the induced pluripotent stem cells derived from humans, monkeys, pigs, horses, cattle, sheep, dogs, cats, mice, rabbits and the like, and the induced pluripotent stems derived from human are preferred.

In the present invention, the term "embryonic stem cell (ESC)" refers to cells extracted from the inner cell mass of a bastocyst, an early-stage preimplantation embryo and cultured in vitro, and having self-reproduction capability and pluripotency which can differentiate into cells of all tissues of the object. This may include embryoid bodies derived from embryonic stem cells. The embryonic stem cells of the present invention may include all embryonic stem cells derived from humans, monkeys, pigs, horses, cattle, sheep, dogs, cats, mice, rabbits and like, and the human embryonic stem cells derived from human is preferred.

In the present invention, the term "dedifferentiation" refers to a process in which a differentiated cell can revert to a state having a new type of differentiation potential. The dedifferentiation may be used interchangeably with the reprogramming of cells in the present invention. The reprogramming mechanisms of these cells mean that a nuclear epigenetic mark (DNA state associated with genetic changes in function without a change in the nucleotide sequence) is deleted and then a different set of epigenetic marks is established. During the differentiation and growth of multicelluar organisms, different cells and tissues is to obtain a different gene expression programs.

As used herein, the term "reprogramming promotion" means that the reprogramming during the reprogramming process occurs rapidly or the reprogramming efficiency is increased. This may mean that the efficiency of reprogramming may be increased in view of the speed or rate.

In one specific embodiment of the present invention, it was confirmed that Mfn1 and Mfn2 knockdown using shRNA significantly enhanced the reprogramming efficiency as compared with control shRNA (FIGS. 6a and 6b). Furthermore, complete knockout via the genetic ablation of Mfn1 and 2 yielded a significantly higher reprogramming efficiency (FIG. 6e) and a fragmented mitochondrial morphology (FIG. 6f) compared with WT mouse embryonic fibroblasts. In particular, Mfn1−/−(Mfn1-KO) exhibited a significant increase of about 500 times or more in the numbers of AP+ colonies and Mfn2−/−(Mfn1-KO) exhibited a significant increase of about 200 times or more in the numbers of AP+ colonies, as compared with that for the wild type (WT)(FIG. 6e). This shows that reprogramming efficiency of somatic cells via the ablation of Mfn1 and Mfn2 could be significantly increased.

These results demonstrate that, by using a composition comprising a repressor of mitofusin gene expression, an inhibitor of mitofusin protein activity, or a mixture thereof as an active ingredient, the reprogramming can be effectively rapidly performed, and the pluripotent (induced pluripotent) stem cells produced using the said composition can normally acquire the pluripotency.

Specifically, the composition for promoting reprogramming promotion according to the present invention may be in the form of a culture medium or culture medium additives. Accordingly, the composition of the present invention may further comprise a substance generally comprised in cell culture medium unless it is an obstacle in reprogramming to pluripotent stem cells from differentiated cells.

In addition, the composition for facilitating the reprogramming of differentiated cells into pluripotent stem cells in accordance with the present invention may comprise at least one reprogramming factor.

As used herein, the term "reprogramming factor" refers to a substance which induces so that finally differentiated cells are reprogrammed into pluripotent stem cells having a new type of differentiation potential. In the present invention, the term "reprogramming factor" may be used interchangeably with the term "reprogramming-inducible factor". The reprogramming factor may comprise any of the substances to induce the reprogramming of finally differentiated cells, without limitation, and it may be selected depending on the kinds of cells to be differentiated. Specifically, the reprogramming-inducible factor may further comprise, but is not limited to, proteins selected from the group consisting of Oct4, Sox2, Klf4, c-Myc, Nanog, Lin-28 and Rex1 or a nucleic acid molecule encoding these proteins.

In the present invention, the term "nucleic acid molecule encoding a protein" may be a form that is operatively linked to a promoter and the like so as to express the protein itself when delivered in the cells. Also, this broadly includes a nucleic acid molecule which can be inserted into an intracellular chromosome to express the protein. For example, at least one of the nucleic acid molecules encoding a protein selected from the group consisting of Oct4, Sox2, Klf4, c-Myc, Nanog, Lin-28, and Rex1 as the reprogramming-inducible factor, operatively linked to an expression vector, can be delivered into the cells, and it may be delivered into the cells in a form to be inserted into a chromosome of host cells.

In an exemplary embodiment of the present invention, the somatic cells were transfected with retrovirus 1 MOI (multiplicity of infection) encoding Oct4, Sox2, Klf4 and c-Myc, the reprogramming-inducible factor, thereby inducing reprogramming of mouse or human fibroblasts (Experiment 3).

The composition may comprise a repressor of mitofusin gene expression, an inhibitor of mitofusin protein activity, or a mixture thereof as an active ingredient for promoting reprogramming a differentiated cell into a pluripotent stem cell.

In another aspect, the invention provides a medium composition comprising a repressor of mitofusin gene expression, an inhibitor of mitofusin protein activity, or a mixture thereof as an active ingredient for maintaining and culturing pluripotent stem cells in an undifferentiated state. In the present invention, the repressor of mitofusin gene expression or the inhibitor of mitofusin protein activity may include a function to maintain pluripotent stem cells in an undifferentiated state and thus can be used in the above-described composition. In addition, the medium composition for maintaining and culturing pluripotent stem cells according to the present invention can further comprise a substance generally comprised in cell culture medium unless it is an obstacle to maintain and culture the cells in an undifferentiated state.

The above-described "repressor of mitofusin gene expression", "inhibitor of mitofusin protein activity", or "pluripotent stem cell" are as previously described.

In one specific embodiment of the present invention, in culture conditions using unconditioned medium (UM), human embryonic stem cells (hESC) led to differentiation, but hESCs with Mfn1 and 2 knockdown using siRNA were maintained in the undifferentiated state (FIG. 6c). Under UM culture conditions, the expression of pluripotency-associated markers such as Oct3/4 and Nanog was maintained well in hESCs upon knockdown of Mfn1 and 2 (FIGS. 6d and 7). These results demonstrate that in the case of repressing or genetically ablating the mitofusin, pluripotent stem cells were maintained in differentiated state.

Yet another aspect of the invention provides a method for producing a pluripotent stem cell reprogrammed from a differentiated cell, comprising (a) delivering at least one reprogramming factor to a differentiated cell, and (b) culturing the differentiated cell in a medium containing the composition for promoting the reprogramming. In the method for producing a pluripotent stem cell reprogrammed by inhibiting mitofusin in differentiated cells according to the present invention, the reprogrammed cell numbers are greatly increased and the time required for the reprogramming are greatly shortened, thus leading to a significant increase in the reprogramming efficiency, compared with a conventional method for producing the reprogrammed pluripoent stem cells.

The "differentiated cell", "reprogramming factor" and "pluripotent stem cell" are as previously described.

The method of delivering at least one reprogramming factor to a differentiated cell in step (a) may use, without limitation, a method of providing a nucleic acid molecule or protein, typically in the cell used in the art. Exemplary examples thereof may comprise a method of administering the reprogramming factor to a culture solution of differentiated cells, a method of injecting the reprogramming factor in the differentiated cells or a method of infecting the differentiated cells with a virus which is obtained from packaging cells transfected with a virus vector in which a gene of the reprogramming factor is inserted.

The virus vectors may include vectors derived from retrovirus, for example HIV (human immunodeficiency virus), MLV (murine leukemia virus), ASLV (avian sarcoma/leukosis), SNV (spleen necrosis virus), RSV (rous sarcoma virus), mMTV (mouse mammary tumor virus), etc., lentivirus, adenovirus, adeno-associated virus, herpes simplex virus, and the like, but are not limited thereto. Specifically, retrovirus vector may be used. More specifically, retrovirus vector PMXs may be used.

The method for inducing the reprogramming factor directly to the differentiated cells may select and use any method known in the art. It may appropriately select and use, but is not limited to, any of the methods including microinjection, electroporation, particle bombardment, direct muscle injection, insulator, and transposon.

Also, step (a) and step (b) may be performed simultaneously, sequentially or in reverse order, and the method may further comprise the step of separating the embryonic stem cell-like colonies from the culture from the step (b).

More specifically, in present invention, the pluripotent stem cell may have an increased production of lactic acid which is a by-product of glycolysis, or an activated Ras-Raf-HIF1α signaling, or a reduced oxygen consumption, compared with that of the differentiated cells, wherein the reprogramming efficiency may be improved by reducing the time required for reprogramming and increasing the number of reprogrammed cells.

In an exemplary embodiment of the present invention, the expression of genes encoding major enzymes involved in glycolysis and the relative quantity of metabolites in each step of glycolysis were dramatically increased in Mfn1 and 2 knockdown cells compared with the control (FIGS. 8a and 8b), and intracellular lactate production was indeed increased by Mfn1 and 2 knockdown (FIG. 8c).

During the early stage of reprogramming, reciprocal inhibition of the Mfn1/2 and p53/p21 pathways activates Ras-Raf signaling, leading to subsequent HIF1α stabilization (FIG. 10f), indicating that it is possible to mimic hypoxic conditions, which are favorable for efficient reprogramming. Further, under hypoxic conditions, a significant increase of iPSC generation was observed (FIG. 12a), and a related increase in the HIF1α and LDHA proteins was observed (FIG. 12b). Under the same conditions, the promoter activity of Mfn1 was significantly down-regulated (FIG. 12c), and the protein expression of Mfn1 and 2 was prominently down-regulated (FIG. 12b).

A further aspect of the present invention provides a pluripotent stem cell prepared by the method of producing a pluripotent stem cell reprogrammed from differentiated cell. Specifically, the pluripotent stem cell may be induced pluripotent stem cell.

The "pluripotent stem cell" and "induced pluripotent stem cell" are as previously described.

In the specific embodiment of the present invention, through the method for producing pluripotent stem cells having a very high reprogramming efficiency according to the present invention, the pluripotent stem cells reprogrammed from mouse and human fibroblasts was obtained (FIGS. 6a, 6b and 6e).

A further embodiment of the present invention provides a method for reprogramming an isolated differentiated cell into a pluripotent stem cell comprising repressing the expression of mitofusin gene or inhibiting an activity of mitofusin protein of the isolated differentiated cell. More specifically, repressing the expression of mitofusin gene or inhibiting an activity of mitofusin protein may be performed by treating the isolated differentiated cell with the composition for promoting the reprogramming.

The "differentiated cell", "repressing the expression of mitofusin gene", "inhibiting the activity of protein", "pluripotent stem cell", and "reprogramming" are as previously described.

Yet in another aspect, the invention provides pluripotent stem cell prepared by the reprogramming method. Specifically, the pluripotent stem cell may be induced pluripotent stem cell.

The "pluripotent stem cell" and "induced pluripotent stem cell" are as previously described.

Yet in another aspect, the invention provides a use of a repressor of mitofusin gene expression, an inhibitor of mitofusin protein activity, or a mixture thereof for producing a composition for promoting the reprogramming of differentiated cell into pluripotent stem cell. Specifically, the pluripotent stem cell may be induced pluripotent stem cell.

The "pluripotent stem cell", "induced pluripotent stem cell", "differentiated cell", "repressor of mitofusin gene expression", "inhibitor of mitofusin protein activity", and "reprogramming" are as previously described.

In the present invention, the term "repressor" may be used interchangeably with the term "inhibitor", and the term "repress" may be used interchangeably with the term "inhibit".

MODE FOR INVENTION

Hereinafter, the present invention will be described in detail to aid the understanding thereof with reference to the examples and the like. However, examples according to the present invention can be modified in many different forms and it should not be construed that the scope of the present invention is limited to the examples below. Examples of the invention are provided to illustrate more fully the present invention to those having ordinary skill in the art.

Experimental Example 1

Reagents

Mdivi1, 2-deoxy-D-glucose (2-DG), and lentiviral vectors that express each shRNA for gene knockdown were purchased from Sigma. siRNAs for mitofusin 1 or 2 (Mfn1/2) knockdown were purchased from Dharmacon. Nutlin3a was purchased from Cayman Chemical Co. A Screen-Well™ REDOX library was purchased from Enzo Life Sciences. The shRNA sequences for Mfn1/2 (shMfn1, shMfn2) and siRNA sequences for Mfn1/2 (siMfn1, siMfn2), used in the present invention, are presented in Table 1 below.

TABLE 1

| | | | | |
|---|---|---|---|---|
| mouse | shMfn1 | Target Sequence: | GCGTTTAAGCAGCAGTTTGTA | SEQ ID NO: 5 |
| | | Hairpin Sequence: | 5'-CCCG-GCGTTTAAGCAGC AGTTTGTA-CTCGAG-TACAA ACTGCTGCTTAAACCC-TTTT TG-3' | SEQ ID NO: 6 |
| | shMfn2 | Target Sequence: | TGGATGGACTATGCTAGTGAA | SEQ ID NO: 7 |
| | | Hairpin Sequence: | 5'-CCGG-TGGATGGACTATG CTAGTGAA-CTCGAG-TTCAC TAGCATAGTCCATCCA-TTTT TG-3' | SEQ ID NO: 8 |
| human | shMfn1 | Target Sequence: | ATCCGGAACTTGATCGAATAG | SEQ ID NO: 9 |
| | | Hairpin Sequence: | 5'-CCGG-ATCCGGAACTTGA TCGAATAG-CTCGAG-CTATT CGATCAAGTTCCGGAT-TTTT TTGAAT-3' | SEQ ID NO: 10 |
| | shMfn2 | Target Sequence: | GCTCAGTGCTTCATCCCATTT | SEQ ID NO: 11 |
| | | Hairpin Sequence: | 5'-CCGG-GCTCAGTGCTTCA TCCCATTT-CTCGAG-AAATG GGATGAAGCACTGAGC-TTTT TG-3' | SEQ ID NO: 12 |
| | siMfn1 | SMARTpool | CGAUGAAGUAAACGCCUUA | SEQ ID NO: 13 |
| | | | CAUGAUAGGAGGAAACGAA | SEQ ID NO: 14 |
| | | | CAGAAUAUAUGGAAGACGU | SEQ ID NO: 15 |
| | | | GGAAGUUCUUAGUGCUAGA | SEQ ID NO: 16 |
| | siMfn2 | SMARTpool | GACUAUAAGCUGCGAAUUA | SEQ ID NO: 17 |
| | | | CAUGAGGCCUUUCUCCUUA | SEQ ID NO: 18 |
| | | | GCAACUCUAUCGUCACAGU | SEQ ID NO: 19 |
| | | | GGUGGACGAUUACCAGAUC | SEQ ID NO: 20 |

Experimental Example 2

Mice and Cell Culture

All animal experimental protocols were approved by the bioethics committee of KRIBB. MEFs were isolated from embryonic day 12.5 embryos obtained from WT, p53-KO (p53−/−) and p21-KO (p21−/−) mice (The Jackson Laboratory) and maintained in DMEM (Invitrogen) supplemented with 10% fetal bovine serum (FBS, Invitrogen), 1% non-essential amino acids (NEAA, Invitrogen), 0.1 mM β-mercaptoethanol (Sigma), and 1% penicillin/streptomycin (Invitrogen). The mouse embryonic stem cell (ESC) line J1 (ATCC) and induced pluripotent stem cell (iPSC) lines were routinely maintained on γ-irradiated MEFs or Matrigel™ (BD Biosciences)-coated plates in DMEM (Invitrogen) supplemented with 15% FBS, 1% NEAA, 1% L-glutamine (Invitrogen), 20 mM HEPES (Invitrogen), 0.1 mM β-mercaptoethanol, 1% penicillin/streptomycin, and 1,000 U/ml LIF (Millipore). The culture medium was changed every other day. Human H9 ESC lines (WiCell Research Institute) were routinely maintained on γ-irradiated MEFs in hESC culture medium (unconditioned medium; UM) or Matrigel™-coated plates in MEF-CM (conditioned medium). The culture medium was changed daily, and cells were passaged every 5-7 days following collagenase IV (1 mg/ml; Invitrogen) or dispase (1 mg/ml; Invitrogen) treatment. Human foreskin fibroblasts (hFFs; ATCC) were maintained in DMEM containing 10% FBS, 1% NEAA, 1 mM L-glutamine, and 0.1 mM β-mercaptoethanol.

Experimental Example 3

Virus Production and iPSC Generation

GP2-293 packaging cells were co-transfected with pMX vectors containing the human cDNAs for Oct4 (POU5F1), Sox2, Klf4, and c-Myc (OSKM, Addgene) and the VSV-G envelope vector using Lipofecamine 2000 transfection reagent (Invitrogen). Virus-containing supernatants were collected at 48 and 72 hours after transfection and concentrated via ultracentrifugation (Beckman Coulter) at 25,000 rpm for 90 minutes. To generate iPSCs, MEFs were seeded at $1 \times 10^5$ cells per well in 6-well plates the day before transduction and subsequently transduced with concentrated virus at a multiplicity of infection (MOI) of 1 in the presence of Polybrene (8 μg/ml). Four days after transduction, the MEFs were trypsinized and reseeded at a density of $3 \times 10^4$ cells per well in Matrigel™-coated 12-well plates. On the next day, the medium was replaced with mouse ESC medium, and the medium was changed every other day thereafter.

Experimental Example 4

Alkaline Phosphatase (AP) Staining

AP staining was performed with an alkaline phosphatase (AP) kit according to the manufacturer's protocol (Sigma). Cells were fixed with a citrate-acetone-formaldehyde solution for 30 sec and then stained with AP staining solution (Naphthol/Fast Red Violet) for 15 min in the dark. Images of AP+cells were obtained with a HP Scanjet G4010 (Hewlett-Packard).

Experimental Example 5

RNA Extraction, Real-Time Polymerase Chain Reaction (PCR), and Microarray Analysis Total RNA was isolated from cells with the RNeasy Mini Kit (Qiagen) and reverse-transcribed with the SuperScript First-Strand Synthesis System Kit (Invitrogen) according to the manufacturers' protocols. Quantitative real-time PCR was performed with Fast SYBR® Green Master Mix (Life Technologies) on a 7500 Fast Real-Time PCR System (Applied Biosystems). The primer sequences used in the present invention are presented in Table 2 below. Transcriptome analysis was conducted with Agilent Mouse Genome 44 k Arrays.

TABLE 2

| Gene | Forward Primer | Reverse Primer |
|---|---|---|
| Mfn1 | TGAAAGCTGGCTGTCTTGTG (SEQ ID NO: 21) | AGAGCCGCTCATTCACCTTA (SEQ ID NO: 22) |
| Mfn2 | CCTCACAGAGGGCTCAGAAG (SEQ ID NO: 23) | GTCCAGCTCCGTGGTAACAT (SEQ ID NO: 24) |
| p53 | AGAGACCGCCGTACAGAAGA (SEQ ID NO: 25) | CTGTAGCATGGGCATCCTTT (SEQ ID NO: 26) |
| p21 | CGGTGGAACTTTGACTTCGT (SEQ ID NO: 27) | CAGGGCAGAGGAAGTACTGG (SEQ ID NO: 28) |
| Glycolysis | | |
| Glut1 | GATCCTGGGCCGCTTCAT (SEQ ID NO: 29) | ACATGGGCACGAAGCCTG (SEQ ID NO: 30) |
| Hif1α | TCAAGTCAGCAACGTGGAAG (SEQ ID NO: 31) | TATCGAGGCTGTGTCGACTG (SEQ ID NO: 32) |
| hk2 | GGGACGACGGTACACTCAAT (SEQ ID NO: 33) | GCCAGTGGTAAGGAGCTCTG (SEQ ID NO: 34) |
| Pfk | ATGGCAAAGCTATCGGTGTC (SEQ ID NO: 35) | ACACAGTCCCATTTGGCTTC (SEQ ID NO: 36) |
| Pam1 | GCCTGATCACCCCTTCTACA (SEQ ID NO: 37) | TCAAGACCCTTTTCCCCTCT (SEQ ID NO: 38) |
| Eno1 | AGTACGGGAAGGACGCCACCA (SEQ ID NO: 39) | GCGGCCACATCCATGCCGAT (SEQ ID NO: 40) |
| Pkm | CTGCAGGTGAAGGAGAAAGG (SEQ ID NO: 41) | AGATGCAAACACCATGTCCA (SEQ ID NO: 42) |
| Ldha | TGGCAGCCTCTTCCTTAAAA (SEQ ID NO: 43) | CAGCTTGCAGTGTGGACTGT (SEQ ID NO: 44) |
| β-actin | AGCCATGTACGTAGCCATCC (SEQ ID NO: 45) | CTCTCAGCTGTGGTGGTGAA (SEQ ID NO: 46) |
| Oxidative phosphorylation | | |
| ND132 | CCCATTCGCGTTATCTT (SEQ ID NO: 47) | AAGTTGATCGTAACGGAAGC (SEQ ID NO: 48) |
| Atp6ap1 | GCCATGGAACGACTTGAAAT (SEQ ID NO: 49) | CGGAGAGAAGAAACCAGCAC (SEQ ID NO: 50) |
| Sdhb | ACTGGTGGAACGGAGACAAG (SEQ ID NO: 54) | TTAAGCCAATGCTCGCTTCT (SEQ ID NO: 52) |
| Uqcrc1 | CCTACAGCACTCGAGAGCAC (SEQ ID NO: 53) | AGGTGTGCCCTGGAATGCTG (SEQ ID NO: 54) |

Experimental Example 6

Metabolome Analysis

Cells were washed with a 5% mannitol solution (Wako) and scraped in MeOH (Wako) including internal standards. The aqueous layer was separated via centrifugation at 3,200 rpm for 10 minutes. Metabolite extracts were prepared using 5 kDa-cutoff ultrafilter tips (Millipore) at 9,100×g for 2.5 hours, then evaporated in a centrifugal evaporator (SCAN-VAC), and capillary electrophoresis time-of-flight mass spectrometry (CE-TOFMS) was conducted according to the recommended protocols (Human Metabolome Technologies).

Experimental Example 7

Lactate and ATP Assays

The intracellular lactate contents were quantified from 10 μg of protein using a Lactate Assay Kit (BioVision) according to the manufacturer's protocol. ATP was measured from 0.1 μg of protein using an ADP/ATP Ratio Assay Kit (Abcam). The luminescence intensity was quantified using a SpectraMax microplate reader (Molecular Devices).

Experimental Example 8

Mitochondrial Staining

Cells were fixed in 4% paraformaldehyde for 10 minutes at room temperature (RT) and then in MeOH for 15 minutes at −20° C., after which their permeability was increased with 0.3% Triton X-100 in PBS for 30 min and blocked with 4% BSA for 2 hours at RT. The samples were stained with the anti-Tom20 antibody diluted in a blocking buffer at 4° C. overnight. After washing, the cells were stained with Alexa 488-conjugated secondary antibodies (Invitrogen) for 45 minutes at RT. The nuclei were counterstained with 10 μg/ml DAPI. For live cell imaging, the cells were incubated with 200 nM MitoTracker® Red CMXRos (Invitrogen) for 30 minutes at 37° C. Florescent images were analyzed under an IX51 microscope (Olympus) or an Axiovert 200M microscope (Carl Zeiss). The antibodies used in these assays are listed in Table 3 below.

TABLE 3

| Antibody | Catalog No. | Company | Dilution |
|---|---|---|---|
| anti-Tom20 | sc-17764 | SantaCruz | 1:70 |
| anti-HSP60 | 4870 | Cell Signaling | 1:500 |
| anti-Cyclin B1 | sc-245 | Santacruz | 1:1000 |
| anti-p-Drp1 | 3455 | Cell signaling | 1:1000 |
| anti-Drp1 | 8570 | Cell signaling | 1:1000 |
| anti-Mfn1 | ABC41 | Millpore | 1:2000 |
| anti-Mfn2 | ab50843 | abcam | 1:1000 |
| anti- β-acin | A1978 | Sigma | 1:500000 |
| anti- mNanog | A300-397A | Bethyl Lab | 1:5000 |
| anti- Nanog | AF1997 | R&D | 1:200 |
| anti- Oct3/4 | sc-8628 | Santacruz | 1:500 |
| anti-Thy1.1 | 551401 | BD | 1:50 |
| anti-p53 | 2524 | Cell signaling | 1:1000 |
| anti-p21 | sc-397 | SantaCruz | 1:4000 |
| anti-Ras | 3965 | Cell signaling | 1:1000 |
| anti-p-Raf | 9427 | Cell signaling | 1:1000 |
| anti-Raf | 9422 | Cell signaling | 1:1000 |
| anti-p-ERK | 9101 | Cell signaling | 1:1000 |
| anti-ERK | 9102 | Cell signaling | 1:2000 |
| anti-p-PI3K | 4228 | Cell signaling | 1:1000 |
| anti-p-Akt | 9271 | Cell signaling | 1:1000 |
| anti-p-mTOR | 2971 | Cell signaling | 1:1000 |

Experimental Example 9

Cell Sorting and Mitochondrial Morphology Analysis

A single-cell suspension of reprogramming cultures on day 11 was labeled with anti-Thy1-PE antibodies (BD Biosciences) for 20 minutes at RT, then incubated with anti-PE microbeads (Miltenyi Biotec) for 15 minutes at 4° C. sorted using a MACS separation system (Miltenyi Biotec). Thy1-negative populations were then labeled with anti-SSEA1 microbeads (Miltenyi Biotec) for 20 minutes at RT and sorted using MACS. To ensure a high purity of the sorted populations, two separation columns were used consecutively. The sorted cells were reseeded at a density of $3 \times 10^4$ cells per well in Matrigel™-coated 12-well plates or used for mitochondrial fractionation. Three days after reseeding, mitochondria were visualized via MitoTracker staining under a fluorescent microscope, and cell numbers were counted according to the observed mitochondrial morphology as fragmented/intermediate/fused. Over 30 cells per sorted subpopulation were scored.

Experimental Example 10

Mitochondrial Fractionation and Western Blot Analysis

Mitochondria were fractionated from each MACS-sorted subpopulation using a mitochondria isolation kit (Thermo). For Western blot analysis, whole-cell lysates were obtained using RIPA buffer, and proteins were separated via SDS-PAGE and electrotransferred to PVDF membranes (Millipore). The antibodies used are listed in Table 2.

Experimental Example 11

Promoter Assay and Chemical Screening

Mfn1-KO MEFs were stably transfected with an Mfn1 promoter reporter construct (Genecopoeia) cells of mouse and human were produced using Mfn1−/− MEFs and 293T cells (human embryonic renal cells) and then treated with the Screen-Well™ REDOX library, containing 84 compounds, for 48 hours in a concentration of 10 nM to 10 μM. Mfn1 promoter activity was measured in the culture supernatants with the Secrete-Pair™ Dual Luminescence and *Gaussia* Luciferase Assay Kits (Genecopoeia) using a SpectraMax microplate reader.

Experimental Example 12

Statistics

The data are presented as the mean±SE (n=3). Student's t-test was applied to evaluate between-group comparisons. A value of p<0.05 was considered significant.

Example 1

Analysis of Mitochondrial Function During Early-Stage Reprogramming of p53−/− and p21−/− Somatic Cells The reprogramming efficiency to generate iPSCs, determined by alkaline phosphatase (AP) staining, was increased in p53−/− and p21−/− mouse embryonic fibroblasts (MEFs; FIG. 1a). Beginning in the early stage of reprogramming, around day 7 (D7; FIG. 1b), dramatic morphological changes together with a substantial increase in cell numbers were observed in p53−/− and p21−/− cells compared with the wild-type control (FIG. 1c). To elucidate the underlying mechanisms of the early stage of reprogramming, microarray-based transcriptome and mass spectrometry-based metabolome analyses were performed using WT, p53−/−, and p21−/− MEFs at D7 of reprogramming.

Transcriptome analysis showed that p53−/− and p21−/− cells reprogrammed for 7 days were positioned at an intermediate stage between initiation (early) and maturation (late), as determined by comparing the levels of marker expression allowing discrimination of the stages of reprogramming (FIG. 2a).

Also, the expression of gene sets related to cell growth, adhesion, RNA splicing, and the cell cycle was markedly increased, and conversely, differentiation-related genes were downregulated in reprogramming intermediates from p53−/− and p21−/− cells compared with those of WT cells (FIG. 2b). However, within the central carbon pathway, glycolysis showed no significant changes regarding reprogramming intermediates from p53−/− and p21−/− cells (FIGS. 1d and 2c). The expression of genes encoding major enzymes involved in glycolysis remained unchanged, and the relative quantity of metabolites in each step of glycolysis decreased in reprogramming intermediates from p53−/− and p21−/− cells compared with WT cells (FIG. 1d). However, the intracellular production of lactate, the end-product of glycolysis, was sequentially increased upon reprogramming and promoted by p53−/− and p21−/− (FIG. 3a), whereas cellular reprogramming was substantially decreased by a glycolysis inhibitor, 2-DG (Supplementary FIG. 3b).

On the contrary, gene expression related to mitochondrial function was markedly suppressed in reprogramming intermediates from p53−/− and p21−/− cells compared with WT, but the expression levels of tricarboxylic acid (TCA) cycle-related genes remained unchanged (FIG. 1e). Notably, mitochondria-encoded oxidative phosphorylation (OXPHOS) subunits, including ND1 (complex I) and Atp6ap1 (ATP6 family in complex V), were markedly downregulated, whereas nuclear-encoded genes were not (Sdhb in complex II, Uqcrc1, and the ATP5 family in complex V) (FIGS. 4a and 4b). Importantly, mitochondrial fusion genes, such as Mfn1/2 and Chchd3, showed significantly decreased levels in reprogramming intermediates from p53−/− and p21−/− cells, whereas the levels of fission genes, such as Dnm1, Dnm1l (Drp1), Fis1, and Mff, were increased or remained unchanged (FIGS. 1e and f).

Furthermore, a reduced ADP/ATP ratio (an energy turnover index) was found in reprogramming intermediates from p53−/− cells compared with the WT control (FIG. 4c). These results suggest that a metabolic shift from mitochondrial dependence to independence occurs more rapidly and efficiently during the reprogramming of p53−/− and p21−/− cells compared with WT cells.

Example 2

Expression Analysis of Mitochondrial Fusion Proteins in p53−/− and p21−/− Cells; and Pluripotent Reprogramming Intermediates On D7 after reprogramming, reprogramming intermediates from p53−/− and p21−/− cells displayed some fragmented and punctate mitochondria, which is characteristic of pluripotent stem cells, while reprogramming intermediates from WT cells did not (FIG. 5a). Prior to the reprogramming, fragmented mitochondria (FIG. 5b) and increased cell proliferation (FIG. 5c) were detected in p53−/− and p21−/− MEFs compared with WT cells. The expression of mitochondrial structural components between somatic WT MEFs, p53−/− and p21−/− MEFs, and pluripotent stem cells [PSCs (ESCs and iPSCs)] showed large differences at the protein level. Cyclin B1-dependent Drp1 phosphorylation and Drp1 protein expression was higher in p53−/− and p21−/− MEFs and PSCs than in WT MEFs. Conversely, Mfn 1 and 2 expression was significantly lower in PSCs and p53−/− and p21−/− MEFs compared with WT MEFs (FIG. 5d). To further examine the correlation between pluripotency induction and mitochondrial dynamics, reprogramming intermediates were sorted on D11 after reprogramming via magnetic-activated cell sorting (MACS) based on the expression of the somatic cell marker Thy1 and the early-stage pluripotency marker SSEA1 (FIG. 5e). The mitochondrial morphology of the Thy1+/SSEA1− (somatic), Thy1−/SSEA1− (early intermediate), and Thy1−/SSEA1+ (late intermediate) subpopulations was scored and quantified as fused(somatic)/intermediate/fragmented(pluripotent). Upon reprogramming, the fragmented phenotype was markedly increased in the Thy1−/SSEA1+ subpopulation, while the fused form gradually disappeared (FIG. 5e). Drp1 expression and phosphorylation levels were significantly increased in the mitochondrial fraction of the Thy1−/SSEA1+ subpopulation, while Mfn1 and 2 expression was decreased (FIG. 5f). Taking these findings together, it can be seen that the p53−/− and p21−/− cells are in a reprogramming-favorable state with a distinct mitochondrial background showing low expression of Mfns, which is similar to pluripotent reprogramming intermediates (FIG. 5g).

Example 3

Pluripotency Acquisition and Maintenance Via Mfn1 and Mfn2 Ablation

Whether Mfn1/2 downregulation contributes to somatic cell reprogramming was confirmed (FIG. 6). Mfn1 and Mfn2 knockdown using shRNA strongly enhanced the observed reprogramming efficiency in both mouse (FIG. 6a) and human cell systems (FIG. 6b), as assayed by AP staining, whereas control shRNA failed to show the same. In addition, in culture conditions using unconditioned medium (UM), hESC differentiation occurred, but Mfn1 and 2 knockdown with siRNA was maintained in the undifferentiated state (FIG. 6c). Under UM culture conditions, the expression of pluripotency-associated markers such as Oct3/4 and Nanog was maintained well in hESCs upon knockdown of Mfn1 and 2 (FIGS. 6d and 7).

Furthermore, complete knockout via the genetic ablation of Mfn1 and Mfn2 yielded a significantly higher reprogramming efficiency (FIG. 6e) and a fragmented mitochondrial morphology (FIG. 6f) compared with WT MEFs. In particular, Mfn1−/− exhibited about 500 times or more significant increase in the numbers of AP+ colonies and Mfn2−/− exhibited about 200 times or more increase in the numbers of AP+ colonies as compared with WT (FIG. 6e). These results confirm that reprogramming efficiency of somatic cells via the ablation of Mfn1 and 2 could be significantly increased. However, these effects were blocked by treatment with Mdivi1, a pharmacological inhibitor of mitochondrial fission (FIGS. 6e and 6f).

These results demonstrate that in the case of inhibiting or genetically ablating mitochondrial structural protein Mfn, the efficiency of reprogramming a differentiated cell into a pluripotent stem cell was greatly increased and the pluripotency was maintained.

Example 4

Mfn1 and 2 Knockdown Facilitates Glycolytic Conversion in Early-Stage Reprogramming To clarify the mechanism promoting cell fate transition to pluripotency induced by Mfn1/2 knockdown, transcriptome and metabolome analyses were performed in D7 reprogramming cultures of Mfn1 and 2 shRNA-transduced cells (FIG. 8). As a result, gene expression profiling of the OXPHOS complex following Mfn1 and Mfn2 knockdown revealed overall downregulation of genes specifying mitochondrial energy metabolism (FIG. 9a). However, the expression of genes encoding major enzymes involved in glycolysis and the relative quantity of metabolites in each step of glycolysis were dramatically increased in Mfn1 and 2 knockdown cells compared with the control (FIGS. 8a and 8b), and intracellular lactate production was indeed increased by Mfn1 and 2 knockdown (FIG. 8c). These findings reveal that the suppression of mitochondrial fusion through Mfn1/2 ablation promotes glycolytic bioenergetic transition to meet the energy demands of highly proliferating pluripotent cells, such as pluripotent iPSCs.

Example 5

Reciprocal Inhibition of p53/p21 and Mfn1/2 Activates the Ras-Raf-HIF1α Signaling Gene expression profiling showed that the expression of p53 (Trp53), p21 (Cdkn1a), and p16 (Cdkn2a) was significantly downregulated in Mfn1 and 2 knockdown cells compared with WT cells (FIGS. 9b and 9c). Also, the protein expression of p53 and p21 was downregulated in Mfn1−/− and Mfn2−/− cells compared with WT cells (FIG. 10a), and Mfn1 expression was suppressed during the reprogramming of p53−/− and p21−/− cells compared with WT cells (FIG. 10b).

The suppression of either of Mfn1/2 (FIGS. 6a, 6b, and 6e) or p53/p21 (FIGS. 1a to 1c) was sufficient for achieving efficient reprogramming of somatic cells into iPSCs, and conversely, either pharmacological reactivation of p53 or overexpression of Mfn1 effectively blocked the induced pluripotent stem cell reprogramming promoted by Mfn1 and 2 (FIG. 10c) or p53 and p21 ablation (FIG. 10d).

These findings suggest the presence of cross-talk between Mfn1/2 and p53/p21 signaling during the reprogramming process. It is already well established that Mfn2 is a direct p53-inducible target gene, and Mfn1 and Mfn2, which shares a high degree of homology with Mfn2, directly bind Ras and Raf, resulting in inhibition of cell proliferation via sequestration of Ras-Raf-ERK signaling. Under the experimental conditions of the present invention, we also observed a dramatic increase in the levels of phosphorylated Raf, ERK, PI3K, Akt, and mTOR proteins in the reprogramming intermediates of Mfn1 and 2 knockdown cells on D7 of reprogramming (FIG. 10e). Moreover, the expression of HIF1α, a downstream effector of mTOR and an important metabolic target of a glycolytic shift, appeared during the early reprogramming process and a downstream target of HIF11α, lactate dehydrogenase isoform A (LDHA)21, was also significantly increased at the protein level in the reprogramming intermediates of Mfn1 and Mfn2 knockdown cells at D7 of reprogramming (FIG. 10e). Further, an increase in the expression of HIF1α and its target Glut1 at the gene level was detected in the reprogramming intermediates of Mfn1 and 2 knockdown cells at D7 of reprogramming (FIG. 8b). On the contrary, HIF1α knockdown using shRNA strongly prevented increased expression of LDHA (FIG. 11a), production of lactate (FIG. 11b), and efficiency of reprogramming (FIG. 11c) in Mfn1 and Mfn2 knockdown cells. Taken together, these results demonstrate that during the early stage of reprogramming, reciprocal inhibition of the Mfn1/2 and p53/p21 pathways activates Ras-Raf signaling, leading to subsequent HIF1α stabilization (FIG. 10f), indicating that it is possible to mimic hypoxic conditions, which are favorable for efficient reprogramming.

Example 6

Hypoxia Decreases Mfn1 and 2 Expression

Under hypoxic conditions, a significant increase in PSC generation (FIG. 12a) and a related increase in the HIF1α and LDHA proteins (FIG. 12b) were observed. Under the same conditions, the promoter activity of Mfn1 was significantly downregulated (FIG. 12c), and the protein expression of Mfn1 and 2 was prominently decreased (FIG. 12b). These findings suggest that the effects of Mfn1/2 on reprogramming are related to the HIF1α-dependent induction of hypoxia-mimicking conditions, possibly via modulating the cross-talk between key components involved in the regulation of p53-dependent signaling and a metabolic switch to glycolysis. Thus, Mfn1/2 downregulation can be an efficient and easy way to switch the cell fate to pluripotency.

Example 7

Mfn1 Expression Inhibition Compound

Chemicals with the aim of altering the promoter activity of Mfn1 using 84 focused redox library compounds were screened.

First, a new use of the top 3 downregulated compounds (piceatannol, tetramethylpyrazine and 21-[4-(2,6-di-1-pyrrolidinyl-4-pyrimidinyl)-1-piperazinyl]pregna-1,4,9[11]-triene-3,20-dione maleate), and the top 2 upregulated compounds (Tanshinone IIA, erbinafine.HCl) controlling mouse Mfn1 promoter activity was identified (FIG. 12d).

When the selected compounds were treated during the reprogramming, Mfn1 protein expression was down-regulated or up-regulated (FIG. 12e). The compounds not influencing on Mfn1 promoter activity did not change the expression of Mfna protein.

Also, compounds that inhibit mouse Mfn1 promoter activity enhanced the reprogramming efficiency of both mouse and human somatic cells (FIGS. 12f and 13a), whereas these compounds that promote Mfn1 promoter activity suppressed the reprogramming (FIGS. 12f and 13a). Also, the inhibitor of Mfn1 promoter activity maintained mouse ESCs (FIG. 12g) and human ESCs (FIG. 13b) in an undifferentiated state.

In addition, a new use of the three compounds that best inhibit human Mfn1 promoter activity (U74389G maleate, retinyl palmitate and D-α-tocopheryl quinone)(FIG. 12h) and that U74389G maleate inhibited Mfn1 promoter activity in both mice and human cells were indentified.

These results demonstrate that inhibitors of Mfn1 or Mfn2 remarkably facilitate reprogramming a differentiated cell into a pluripotent stem cell and maintain the pluripotency and thus, lead a significant improvement in comparison with a conventional reprogramming condition (FIG. 14).

From the above description, a person skilled in the art will appreciate that the present invention may be practiced in other specific forms without changing the technical idea or essential characteristics thereof. In this regard, the embodiments described above should be understood to be illustrative rather than restrictive in every respect. The scope of the invention should be construed that all changes or variations derived from the meaning, scope and equivalent concepts of the appended claims rather than the detailed description fall within the scope of the present invention.

The invention claimed is:

1. A method for producing a pluripotent stem cell reprogrammed from a differentiated cell, comprising:
   (a) inducing reprogramming of the differentiated cell by delivering at least one reprogramming factor selected from the group consisting of Oct4, Sox2, Klf4, c-Myc, Nanog, Lin-28, and Rex1 to a differentiated cell; and
   (b) promoting reprogramming the differentiated cell of (a) by culturing the differentiated cell in a medium comprising a repressor of mitofusin gene expression as an active ingredient,
   wherein the repressor of mitofusin gene expression is at least one selected from the group consisting of an antisense oligonucleotide, siRNA, shRNA, and microRNA that targets a mitofusin gene.

2. The method of claim 1, wherein the mitofusin is derived from a human or a mouse.

3. The method of claim 1, wherein the mitofusin is mitofusin 1 or mitofusin 2.

4. The method of claim 3, wherein the mitofusin 1 consists of the amino acid sequence of SEQ ID NO: 1 or SEQ ID NO: 3, and the mitofusin 2 consists of the amino acid sequence of SEQ ID NO: 2 or SEQ ID NO: 4.

5. The method of claim 1, wherein the differentiated cell is a germ cell, a somatic cell, or a progenitor cell.

6. The method of claim 1, wherein the medium further comprises a culture medium additive.

7. The method of claim 1, wherein the pluripotent stem cell has an increased production of lactic acid, an activated Ras-Raf-HIF1 signaling, or a reduced oxygen consumption, compared with that of the differentiated cells, and wherein the reprogramming efficiency is improved by reducing the time required for reprogramming and increasing the number of reprogrammed cells.

8. A method for reprogramming an isolated differentiated cell into a pluripotent stem cell comprising:
   (a) inducing reprogramming of the differentiated cell by delivering at least one reprogramming factor selected from the group consisting of Oct4, Sox2, Klf4, c-Myc, Nanog, Lin-28, and Rex1 to a differentiated cell; and
   (b) promoting reprogramming the differentiated cell of (a) by repressing the expression of mitofusin gene of the isolated differentiated cell, wherein repressing the expression of mitofusin gene is performed by treating the isolated differentiated cell with a composition comprising a repressor of mitofusin gene expression as an active ingredient,
   wherein the repressor of mitofusin gene expression is at least one selected from the group consisting of an antisense oligonucleotide, siRNA, shRNA, and microRNA that targets a mitofusin gene.

* * * * *

SEQUENCE LISTING

<160> NUMBER OF SEQ ID NOS: 54

<210> SEQ ID NO 1

```
<211> LENGTH: 741
<212> TYPE: PRT
<213> ORGANISM: Mus sp.

<400> SEQUENCE: 1

Met Ala Glu Thr Val Ser Pro Leu Lys His Phe Val Leu Ala Lys Lys
1               5                   10                  15

Ala Ile Thr Ala Ile Phe Gly Gln Leu Leu Glu Phe Val Thr Glu Gly
            20                  25                  30

Ser His Phe Val Glu Ala Thr Tyr Arg Asn Pro Glu Leu Asp Arg Ile
        35                  40                  45

Ala Ser Glu Asp Asp Leu Val Glu Ile Gln Gly Tyr Arg Asn Lys Leu
    50                  55                  60

Ala Val Ile Gly Glu Val Leu Ser Arg Arg His Met Lys Val Ala Phe
65                  70                  75                  80

Phe Gly Arg Thr Ser Ser Gly Lys Ser Ser Val Ile Asn Ala Met Leu
                85                  90                  95

Trp Asp Lys Val Leu Pro Ser Gly Ile Gly His Thr Thr Asn Cys Phe
            100                 105                 110

Leu Ser Val Glu Gly Thr Asp Gly Asp Lys Ala Tyr Leu Met Thr Glu
        115                 120                 125

Gly Ser Asp Glu Lys Lys Ser Val Lys Thr Val Asn Gln Leu Ala His
    130                 135                 140

Ala Leu His Met Asp Lys Asp Leu Lys Ala Gly Cys Leu Val His Val
145                 150                 155                 160

Phe Trp Pro Lys Ala Lys Cys Ala Leu Leu Arg Asp Asp Leu Val Leu
                165                 170                 175

Val Asp Ser Pro Gly Thr Asp Val Thr Thr Glu Leu Asp Ile Trp Ile
            180                 185                 190

Asp Lys Phe Cys Leu Asp Ala Asp Val Phe Val Leu Val Ala Asn Ser
        195                 200                 205

Glu Ser Thr Leu Met Asn Thr Glu Lys His Phe Phe His Lys Val Asn
    210                 215                 220

Glu Arg Leu Ser Lys Pro Asn Ile Phe Ile Leu Asn Asn Arg Trp Asp
225                 230                 235                 240

Ala Ser Ala Ser Glu Pro Glu Tyr Met Glu Asp Val Arg Arg Gln His
                245                 250                 255

Met Glu Arg Cys Leu His Phe Leu Val Glu Leu Lys Val Val Ser
            260                 265                 270

Pro Ser Glu Ala Arg Asn Arg Ile Phe Phe Val Ser Ala Lys Glu Val
        275                 280                 285

Leu Asn Ser Arg Lys His Lys Ala Gln Gly Met Pro Glu Gly Gly Gly
    290                 295                 300

Ala Leu Ala Glu Gly Phe Gln Ala Arg Leu Gln Glu Phe Gln Asn Phe
305                 310                 315                 320

Glu Gln Thr Phe Glu Glu Cys Ile Ser Gln Ser Ala Val Lys Thr Lys
                325                 330                 335

Phe Glu Gln His Thr Ile Arg Ala Lys Gln Ile Leu Asp Thr Val Lys
            340                 345                 350

Asn Ile Leu Asp Ser Val Asn Val Ala Ala Glu Lys Arg Val Tyr
        355                 360                 365

Ser Met Glu Glu Arg Glu Asp Gln Ile Asp Arg Leu Asp Phe Ile Arg
    370                 375                 380

Asn Gln Met Asn Leu Leu Thr Leu Asp Val Lys Lys Lys Ile Lys Glu
```

```
                385                 390                 395                 400
        Val Thr Glu Glu Val Ala Asn Lys Val Ser Cys Ala Met Thr Asp Glu
                        405                 410                 415

Ile Cys Arg Leu Ser Val Leu Val Asp Glu Phe Cys Ser Glu Phe His
                    420                 425                 430

Pro Thr Pro Ser Val Leu Lys Val Tyr Lys Ser Glu Leu Asn Lys His
                    435                 440                 445

Ile Glu Asp Gly Met Gly Arg Asn Leu Ala Asp Arg Cys Thr Asn Glu
                450                 455                 460

Val Asn Ala Ser Ile Leu Gln Ser Gln Gln Glu Ile Glu Asn Leu
        465                 470                 475                 480

Lys Pro Leu Leu Pro Ala Gly Ile Gln Asn Lys Leu His Thr Leu Ile
                        485                 490                 495

Pro Cys Lys Lys Phe Asp Leu Ser Tyr Asp Leu Asn Cys His Lys Leu
                    500                 505                 510

Cys Ser Asp Phe Gln Glu Asp Ile Val Phe Arg Phe Ser Leu Gly Trp
                    515                 520                 525

Ser Ser Leu Val His Arg Phe Leu Gly Ser Thr Asn Ala Gln Arg Val
                530                 535                 540

Leu Leu Gly Leu Ser Glu Pro Ile Phe Gln Val Pro Arg Ser Leu Ala
        545                 550                 555                 560

Ser Thr Pro Thr Ala Pro Ser Asn Pro Ala Ala Pro Asp Asn Ala Ala
                        565                 570                 575

Gln Glu Glu Leu Met Ile Thr Leu Ile Thr Gly Leu Ala Ser Leu Thr
                    580                 585                 590

Ser Arg Thr Ser Met Gly Ile Ile Val Val Gly Gly Val Ile Trp Lys
                595                 600                 605

Thr Val Gly Trp Lys Leu Ile Ser Val Thr Leu Ser Met Tyr Gly Ala
                    610                 615                 620

Leu Tyr Leu Tyr Glu Arg Leu Thr Trp Thr Thr Arg Ala Lys Glu Arg
        625                 630                 635                 640

Ala Phe Lys Gln Gln Phe Val Asn Tyr Ala Thr Glu Lys Leu Gln Met
                        645                 650                 655

Ile Val Ser Phe Thr Ser Ala Asn Cys Ser His Gln Val Gln Gln Glu
                    660                 665                 670

Met Ala Thr Thr Phe Ala Arg Leu Cys Gln Gln Val Asp Val Thr Gln
                    675                 680                 685

Lys His Leu Glu Glu Glu Ile Ala Arg Leu Ser Lys Glu Ile Asp Gln
                690                 695                 700

Leu Glu Lys Ile Gln Asn Asn Ser Lys Leu Leu Arg Asn Lys Ala Ile
        705                 710                 715                 720

Gln Leu Glu Ser Glu Leu Glu Asn Phe Ser Lys Gln Phe Leu His Pro
                        725                 730                 735

Ser Ser Gly Glu Ser
                    740

<210> SEQ ID NO 2
<211> LENGTH: 757
<212> TYPE: PRT
<213> ORGANISM: Mus sp.

<400> SEQUENCE: 2

Met Ser Leu Leu Phe Ser Arg Cys Asn Ser Ile Val Thr Val Lys Lys
1               5                   10                  15
```

```
Asp Lys Arg His Met Ala Glu Val Asn Ala Ser Pro Leu Lys His Phe
             20                  25                  30

Val Thr Ala Lys Lys Ile Asn Gly Ile Phe Glu Gln Leu Gly Ala
         35                  40                  45

Tyr Ile Gln Glu Ser Ala Ser Phe Leu Glu Asp Thr His Arg Asn Thr
     50                  55                  60

Glu Leu Asp Pro Val Thr Thr Glu Glu Gln Val Leu Asp Val Lys Gly
 65                  70                  75                  80

Tyr Leu Ser Lys Val Arg Gly Ile Ser Glu Val Leu Ala Arg Arg His
                 85                  90                  95

Met Lys Val Ala Phe Phe Gly Arg Thr Ser Asn Gly Lys Ser Thr Val
            100                 105                 110

Ile Asn Ala Met Leu Trp Asp Lys Val Leu Leu Ser Gly Ile Gly His
            115                 120                 125

Thr Thr Asn Cys Phe Leu Arg Val Gly Gly Thr Asp Gly His Glu Ala
    130                 135                 140

Phe Leu Leu Thr Glu Gly Ser Glu Glu Lys Lys Ser Val Lys Thr Val
145                 150                 155                 160

Asn Gln Leu Ala His Ala Leu His Gln Asp Glu Gln Leu His Ala Gly
                165                 170                 175

Ser Met Val Ser Val Met Trp Pro Asn Ser Lys Cys Pro Leu Leu Lys
            180                 185                 190

Asp Asp Leu Val Leu Met Asp Ser Pro Gly Ile Asp Val Thr Thr Glu
            195                 200                 205

Leu Asp Ser Trp Ile Asp Lys Phe Cys Leu Asp Ala Asp Val Phe Val
    210                 215                 220

Leu Val Ala Asn Ser Glu Ser Thr Leu Met Gln Thr Glu Lys Gln Phe
225                 230                 235                 240

Phe His Lys Val Ser Glu Arg Leu Ser Arg Pro Asn Ile Phe Ile Leu
                245                 250                 255

Asn Asn Arg Trp Asp Ala Ser Ala Ser Glu Pro Glu Tyr Met Glu Glu
            260                 265                 270

Val Arg Arg Gln His Met Glu Arg Cys Thr Ser Phe Leu Val Asp Glu
            275                 280                 285

Leu Gly Val Val Asp Arg Ala Gln Ala Gly Asp Arg Ile Phe Phe Val
    290                 295                 300

Ser Ala Lys Glu Val Leu Ser Ala Arg Val Gln Lys Ala Gln Gly Met
305                 310                 315                 320

Pro Glu Gly Gly Gly Ala Leu Ala Glu Gly Phe Gln Val Arg Met Phe
                325                 330                 335

Glu Phe Gln Asn Phe Glu Arg Gln Phe Glu Glu Cys Ile Ser Gln Ser
            340                 345                 350

Ala Val Lys Thr Lys Phe Glu Gln His Thr Val Arg Ala Lys Gln Ile
            355                 360                 365

Ala Glu Ala Val Arg Leu Ile Met Asp Ser Leu His Ile Ala Ala Gln
    370                 375                 380

Glu Gln Arg Val Tyr Cys Leu Glu Met Arg Glu Glu Arg Gln Asp Arg
385                 390                 395                 400

Leu Arg Phe Ile Asp Lys Gln Leu Glu Leu Leu Ala Gln Asp Tyr Lys
                405                 410                 415

Leu Arg Ile Lys Gln Ile Thr Glu Glu Val Glu Arg Gln Val Ser Thr
            420                 425                 430

Ala Met Ala Glu Glu Ile Arg Arg Leu Ser Val Leu Val Asp Glu Tyr
```

| | | | | 435 | | | | | 440 | | | | | 445 | | | |
|---|---|---|---|---|---|---|---|---|---|---|---|---|---|---|---|---|---|

Gln Met Asp Phe His Pro Ser Pro Val Val Leu Lys Val Tyr Lys Asn
450 455 460

Glu Leu His Arg His Ile Glu Glu Gly Leu Gly Arg Asn Leu Ser Asp
465 470 475 480

Arg Cys Ser Thr Ala Ile Ala Ser Ser Leu Gln Thr Met Gln Gln Asp
485 490 495

Met Ile Asp Gly Leu Lys Pro Leu Leu Pro Val Ser Met Arg Asn Gln
500 505 510

Ile Asp Met Leu Val Pro Arg Gln Cys Phe Ser Leu Ser Tyr Asp Leu
515 520 525

Asn Cys Asp Lys Leu Cys Ala Asp Phe Gln Glu Asp Ile Glu Phe His
530 535 540

Phe Ser Leu Gly Trp Thr Met Leu Val Asn Arg Phe Leu Gly Pro Lys
545 550 555 560

Asn Ser Arg Arg Ala Leu Leu Gly Tyr Ser Asp Gln Val Gln Arg Pro
565 570 575

Leu Pro Leu Thr Pro Ala Asn Pro Ser Met Pro Pro Leu Pro Gln Ser
580 585 590

Ser Leu Thr Gln Glu Glu Leu Met Val Ser Met Val Thr Gly Leu Ala
595 600 605

Ser Leu Thr Ser Arg Thr Ser Met Gly Ile Leu Val Val Gly Gly Val
610 615 620

Val Trp Lys Ala Val Gly Trp Arg Leu Ile Ala Leu Ser Phe Gly Leu
625 630 635 640

Tyr Gly Leu Leu Tyr Val Tyr Glu Arg Leu Thr Trp Thr Thr Lys Ala
645 650 655

Lys Glu Arg Ala Phe Lys Arg Gln Phe Val Glu Tyr Ala Ser Glu Lys
660 665 670

Leu Gln Leu Ile Ile Ser Tyr Thr Gly Ser Asn Cys Ser His Gln Val
675 680 685

Gln Gln Glu Leu Ser Gly Thr Phe Ala His Leu Cys Gln Gln Val Asp
690 695 700

Ile Thr Arg Asp Asn Leu Glu Gln Ile Ala Ala Met Asn Lys Lys
705 710 715 720

Val Glu Ala Leu Asp Ser Leu Gln Ser Arg Ala Lys Leu Leu Arg Asn
725 730 735

Lys Ala Gly Trp Leu Asp Ser Glu Leu Asn Met Phe Thr His Gln Tyr
740 745 750

Leu Gln Pro Ser Arg
755

<210> SEQ ID NO 3
<211> LENGTH: 741
<212> TYPE: PRT
<213> ORGANISM: Homo sapiens

<400> SEQUENCE: 3

Met Ala Glu Pro Val Ser Pro Leu Lys His Phe Val Leu Ala Lys Lys
1 5 10 15

Gly Ile Thr Ala Ile Phe Asp Gln Leu Leu Glu Phe Val Thr Glu Gly
20 25 30

Ser His Phe Val Glu Ala Thr Tyr Lys Asn Pro Glu Leu Asp Arg Ile
35 40 45

```
Ala Thr Glu Asp Asp Leu Val Glu Met Gln Gly Tyr Lys Asp Lys Leu
    50                  55                  60

Ser Ile Ile Gly Glu Val Leu Ser Arg His Met Lys Val Ala Phe
65                  70                  75                  80

Phe Gly Arg Thr Ser Ser Gly Lys Ser Val Ile Asn Ala Met Leu
                85                  90                  95

Trp Asp Lys Val Leu Pro Ser Gly Ile Gly His Ile Thr Asn Cys Phe
            100                 105                 110

Leu Ser Val Glu Gly Thr Asp Gly Asp Lys Ala Tyr Leu Met Thr Glu
            115                 120                 125

Gly Ser Asp Glu Lys Lys Ser Val Lys Thr Val Asn Gln Leu Ala His
130                 135                 140

Ala Leu His Met Asp Lys Asp Leu Lys Ala Gly Cys Leu Val Arg Val
145                 150                 155                 160

Phe Trp Pro Lys Ala Lys Cys Ala Leu Leu Arg Asp Asp Leu Val Leu
                165                 170                 175

Val Asp Ser Pro Gly Thr Asp Val Thr Thr Glu Leu Asp Ser Trp Ile
            180                 185                 190

Asp Lys Phe Cys Leu Asp Ala Asp Val Phe Val Leu Val Ala Asn Ser
        195                 200                 205

Glu Ser Thr Leu Met Asn Thr Glu Lys His Phe Phe His Lys Val Asn
    210                 215                 220

Glu Trp Leu Ser Lys Pro Asn Ile Phe Ile Leu Asn Asn Arg Trp Asp
225                 230                 235                 240

Ala Ser Ala Ser Glu Pro Glu Tyr Met Glu Asp Val Arg Arg Gln His
                245                 250                 255

Met Glu Arg Cys Leu His Phe Leu Val Glu Glu Leu Lys Val Ala Asn
            260                 265                 270

Ala Leu Glu Ala Gln Asn Arg Ile Phe Phe Val Ser Ala Lys Glu Val
        275                 280                 285

Leu Ser Ala Arg Lys Gln Lys Ala Gln Gly Met Pro Glu Ser Gly Val
    290                 295                 300

Ala Leu Ala Glu Gly Phe His Ala Arg Leu Gln Glu Phe Gln Asn Phe
305                 310                 315                 320

Glu Gln Ile Phe Glu Glu Cys Ile Ser Gln Ser Ala Val Lys Thr Lys
                325                 330                 335

Phe Glu Gln His Thr Ile Arg Ala Lys Gln Ile Leu Ala Thr Val Lys
            340                 345                 350

Asn Ile Met Asp Ser Val Asn Leu Ala Ala Glu Asp Lys Arg His Tyr
        355                 360                 365

Ser Val Glu Glu Arg Glu Asp Gln Ile Asp Arg Leu Asp Phe Ile Arg
    370                 375                 380

Asn Gln Met Asn Leu Leu Thr Leu Asp Val Lys Lys Ile Lys Glu
385                 390                 395                 400

Val Thr Glu Glu Val Ala Asn Lys Val Ser Cys Ala Met Thr Asp Glu
                405                 410                 415

Ile Cys Arg Leu Ser Val Leu Val Asp Glu Phe Cys Ser Glu Phe His
            420                 425                 430

Pro Asn Pro Asp Val Leu Lys Ile Tyr Lys Ser Glu Leu Asn Lys His
        435                 440                 445

Ile Glu Asp Gly Met Gly Arg Asn Leu Ala Asp Arg Cys Thr Asp Glu
    450                 455                 460

Val Asn Ala Leu Val Leu Gln Thr Gln Gln Glu Ile Ile Glu Asn Leu
```

```
                465                 470                 475                 480
Lys Pro Leu Leu Pro Ala Gly Ile Gln Asp Lys Leu His Thr Leu Ile
                    485                 490                 495
Pro Cys Lys Lys Phe Asp Leu Ser Tyr Asn Leu Asn Tyr His Lys Leu
                500                 505                 510
Cys Ser Asp Phe Gln Glu Asp Ile Val Phe Arg Phe Ser Leu Gly Trp
                515                 520                 525
Ser Ser Leu Val His Arg Phe Leu Gly Pro Arg Asn Ala Gln Arg Val
530                 535                 540
Leu Leu Gly Leu Ser Glu Pro Ile Phe Gln Leu Pro Arg Ser Leu Ala
545                 550                 555                 560
Ser Thr Pro Thr Ala Pro Thr Thr Pro Ala Thr Pro Asp Asn Ala Ser
                    565                 570                 575
Gln Glu Glu Leu Met Ile Thr Leu Val Thr Gly Leu Ala Ser Val Thr
                580                 585                 590
Ser Arg Thr Ser Met Gly Ile Ile Ile Val Gly Gly Val Ile Trp Lys
                595                 600                 605
Thr Ile Gly Trp Lys Leu Leu Ser Val Ser Leu Thr Met Tyr Gly Ala
            610                 615                 620
Leu Tyr Leu Tyr Glu Arg Leu Ser Trp Thr Thr His Ala Lys Glu Arg
625                 630                 635                 640
Ala Phe Lys Gln Gln Phe Val Asn Tyr Ala Thr Glu Lys Leu Arg Met
                    645                 650                 655
Ile Val Ser Ser Thr Ser Ala Asn Cys Ser His Gln Val Lys Gln Gln
                660                 665                 670
Ile Ala Thr Thr Phe Ala Arg Leu Cys Gln Gln Val Asp Ile Thr Gln
            675                 680                 685
Lys Gln Leu Glu Glu Ile Ala Arg Leu Pro Lys Glu Ile Asp Gln
        690                 695                 700
Leu Glu Lys Ile Gln Asn Asn Ser Lys Leu Leu Arg Asn Lys Ala Val
705                 710                 715                 720
Gln Leu Glu Asn Glu Leu Glu Asn Phe Thr Lys Gln Phe Leu Pro Ser
                    725                 730                 735
Ser Asn Glu Glu Ser
            740

<210> SEQ ID NO 4
<211> LENGTH: 757
<212> TYPE: PRT
<213> ORGANISM: Homo sapiens

<400> SEQUENCE: 4

Met Ser Leu Leu Phe Ser Arg Cys Asn Ser Ile Val Thr Val Lys Lys
1               5                   10                  15
Asn Lys Arg His Met Ala Glu Val Asn Ala Ser Pro Leu Lys His Phe
                20                  25                  30
Val Thr Ala Lys Lys Lys Ile Asn Gly Ile Phe Glu Gln Leu Gly Ala
            35                  40                  45
Tyr Ile Gln Glu Ser Ala Thr Phe Leu Glu Asp Thr Tyr Arg Asn Ala
        50                  55                  60
Glu Leu Asp Pro Val Thr Thr Glu Glu Gln Val Leu Asp Val Lys Gly
65                  70                  75                  80
Tyr Leu Ser Lys Val Arg Gly Ile Ser Glu Val Leu Ala Arg Arg His
                85                  90                  95
```

-continued

```
Met Lys Val Ala Phe Phe Gly Arg Thr Ser Asn Gly Lys Ser Thr Val
                100                 105                 110
Ile Asn Ala Met Leu Trp Asp Lys Val Leu Pro Ser Gly Ile Gly His
            115                 120                 125
Thr Thr Asn Cys Phe Leu Arg Val Glu Gly Thr Asp Gly His Glu Ala
        130                 135                 140
Phe Leu Leu Thr Glu Gly Ser Glu Glu Lys Arg Ser Ala Lys Thr Val
145                 150                 155                 160
Asn Gln Leu Ala His Ala Leu His Gln Asp Lys Gln Leu His Ala Gly
                165                 170                 175
Ser Leu Val Ser Val Met Trp Pro Asn Ser Lys Cys Pro Leu Leu Lys
            180                 185                 190
Asp Asp Leu Val Leu Met Asp Ser Pro Gly Ile Asp Val Thr Thr Glu
        195                 200                 205
Leu Asp Ser Trp Ile Asp Lys Phe Cys Leu Asp Ala Asp Val Phe Val
210                 215                 220
Leu Val Ala Asn Ser Glu Ser Thr Leu Met Gln Thr Glu Lys His Phe
225                 230                 235                 240
Phe His Lys Val Ser Glu Arg Leu Ser Arg Pro Asn Ile Phe Ile Leu
                245                 250                 255
Asn Asn Arg Trp Asp Ala Ser Ala Ser Glu Pro Glu Tyr Met Glu Glu
            260                 265                 270
Val Arg Arg Gln His Met Glu Arg Cys Thr Ser Phe Leu Val Asp Glu
        275                 280                 285
Leu Gly Val Val Asp Arg Ser Gln Ala Gly Asp Arg Ile Phe Phe Val
    290                 295                 300
Ser Ala Lys Glu Val Leu Asn Ala Arg Ile Gln Lys Ala Gln Gly Met
305                 310                 315                 320
Pro Glu Gly Gly Gly Ala Leu Ala Glu Gly Phe Gln Val Arg Met Phe
                325                 330                 335
Glu Phe Gln Asn Phe Glu Arg Arg Phe Glu Glu Cys Ile Ser Gln Ser
            340                 345                 350
Ala Val Lys Thr Lys Phe Glu Gln His Thr Val Arg Ala Lys Gln Ile
        355                 360                 365
Ala Glu Ala Val Arg Leu Ile Met Asp Ser Leu His Met Ala Ala Arg
    370                 375                 380
Glu Gln Gln Val Tyr Cys Glu Glu Met Arg Glu Glu Arg Gln Asp Arg
385                 390                 395                 400
Leu Lys Phe Ile Asp Lys Gln Leu Glu Leu Leu Ala Gln Asp Tyr Lys
                405                 410                 415
Leu Arg Ile Lys Gln Ile Thr Glu Glu Val Glu Arg Gln Val Ser Thr
            420                 425                 430
Ala Met Ala Glu Glu Ile Arg Arg Leu Ser Val Leu Val Asp Asp Tyr
        435                 440                 445
Gln Met Asp Phe His Pro Ser Pro Val Val Leu Lys Val Tyr Lys Asn
    450                 455                 460
Glu Leu His Arg His Ile Glu Glu Gly Leu Gly Arg Asn Met Ser Asp
465                 470                 475                 480
Arg Cys Ser Thr Ala Ile Thr Asn Ser Leu Gln Thr Met Gln Gln Asp
                485                 490                 495
Met Ile Asp Gly Leu Lys Pro Leu Leu Pro Val Ser Val Arg Ser Gln
            500                 505                 510
Ile Asp Met Leu Val Pro Arg Gln Cys Phe Ser Leu Asn Tyr Asp Leu
```

-continued

|  | 515 |  |  |  | 520 |  |  |  | 525 |  |  |
|---|---|---|---|---|---|---|---|---|---|---|---|

Asn Cys Asp Lys Leu Cys Ala Asp Phe Gln Glu Asp Ile Glu Phe His
530                 535                 540

Phe Ser Leu Gly Trp Thr Met Leu Val Asn Arg Phe Leu Gly Pro Lys
545                 550                 555                 560

Asn Ser Arg Arg Ala Leu Met Gly Tyr Asn Asp Gln Val Gln Arg Pro
            565                 570                 575

Ile Pro Leu Thr Pro Ala Asn Pro Ser Met Pro Pro Leu Pro Gln Gly
            580                 585                 590

Ser Leu Thr Gln Glu Glu Phe Met Val Ser Met Val Thr Gly Leu Ala
            595                 600                 605

Ser Leu Thr Ser Arg Thr Ser Met Gly Ile Leu Val Val Gly Gly Val
            610                 615                 620

Val Trp Lys Ala Val Gly Trp Arg Leu Ile Ala Leu Ser Phe Gly Leu
625                 630                 635                 640

Tyr Gly Leu Leu Tyr Val Tyr Glu Arg Leu Thr Trp Thr Thr Lys Ala
                645                 650                 655

Lys Glu Arg Ala Phe Lys Arg Gln Phe Val Glu His Ala Ser Glu Lys
            660                 665                 670

Leu Gln Leu Val Ile Ser Tyr Thr Gly Ser Asn Cys Ser His Gln Val
            675                 680                 685

Gln Gln Glu Leu Ser Gly Thr Phe Ala His Leu Cys Gln Gln Val Asp
            690                 695                 700

Val Thr Arg Glu Asn Leu Glu Gln Glu Ile Ala Ala Met Asn Lys Lys
705                 710                 715                 720

Ile Glu Val Leu Asp Ser Leu Gln Ser Lys Ala Lys Leu Leu Arg Asn
                725                 730                 735

Lys Ala Gly Trp Leu Asp Ser Glu Leu Asn Met Phe Thr His Gln Tyr
            740                 745                 750

Leu Gln Pro Ser Arg
        755

<210> SEQ ID NO 5
<211> LENGTH: 21
<212> TYPE: DNA
<213> ORGANISM: Mus sp.
<220> FEATURE:
<223> OTHER INFORMATION: Mfn1 shRNA target sequence

<400> SEQUENCE: 5
gcgtttaagc agcagtttgt a                                           21

<210> SEQ ID NO 6
<211> LENGTH: 58
<212> TYPE: DNA
<213> ORGANISM: Artificial Sequence
<220> FEATURE:
<223> OTHER INFORMATION: Description of Artificial Sequence: Synthetic
      mouse Mfn1 shRNA sequence

<400> SEQUENCE: 6
ccgggcgttt aagcagcagt ttgtactcga gtacaaactg ctgcttaaac gctttttg      58

<210> SEQ ID NO 7
<211> LENGTH: 21
<212> TYPE: DNA
<213> ORGANISM: Mus sp.
<220> FEATURE:
<223> OTHER INFORMATION: Mfn2 shRNA target sequence

<400> SEQUENCE: 7
tggatggact atgctagtga a                                              21

<210> SEQ ID NO 8
<211> LENGTH: 58
<212> TYPE: DNA
<213> ORGANISM: Artificial Sequence
<220> FEATURE:
<223> OTHER INFORMATION: Description of Artificial Sequence: Synthetic
      mouse Mfn2 shRNA sequence

<400> SEQUENCE: 8
ccggtggatg gactatgcta gtgaactcga gttcactagc atagtccatc cattttttg     58

<210> SEQ ID NO 9
<211> LENGTH: 21
<212> TYPE: DNA
<213> ORGANISM: Homo sapiens
<220> FEATURE:
<223> OTHER INFORMATION: Mfn1 shRNA target sequence

<400> SEQUENCE: 9
atccggaact tgatcgaata g                                              21

<210> SEQ ID NO 10
<211> LENGTH: 62
<212> TYPE: DNA
<213> ORGANISM: Artificial Sequence
<220> FEATURE:
<223> OTHER INFORMATION: Description of Artificial Sequence: Synthetic
      human Mfn1 shRNA sequence

<400> SEQUENCE: 10
ccggatccgg aacttgatcg aatagctcga gctattcgat caagttccgg attttttga    60 at                                                                   62

<210> SEQ ID NO 11
<211> LENGTH: 21
<212> TYPE: DNA
<213> ORGANISM: Homo sapiens
<220> FEATURE:
<223> OTHER INFORMATION: Mfn21 shRNA target sequence

<400> SEQUENCE: 11
gctcagtgct tcatcccatt t                                              21

<210> SEQ ID NO 12
<211> LENGTH: 58
<212> TYPE: DNA
<213> ORGANISM: Artificial Sequence
<220> FEATURE:
<223> OTHER INFORMATION: Description of Artificial Sequence: Synthetic
      human Mfn2 shRNA sequence

<400> SEQUENCE: 12
ccgggctcag tgcttcatcc catttctcga gaaatgggat gaagcactga gcttttttg    58

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      Mfn1 siRNA sequence

```
<400> SEQUENCE: 13
cgaugaagua aacgccuua                                                19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      human Mfn1 siRNA sequence

<400> SEQUENCE: 14
caugauagga ggaaacgaa                                                19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      human Mfn1 siRNA sequence

<400> SEQUENCE: 15
cagaauauau ggaagacgu                                                19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      human Mfn1 siRNA sequence

<400> SEQUENCE: 16
ggaaguucuu agugcuaga                                                19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      human Mfn1 siRNA sequence

<400> SEQUENCE: 17
gacuauaagc ugcgaauua                                                19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      human Mfn1 siRNA sequence

<400> SEQUENCE: 18
caugaggccu uucuccuua                                                19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      human Mfn1 siRNA sequence

<400> SEQUENCE: 19
```
gcaacucuau cgucacagu                                               19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      human Mfn1 siRNA sequence

<400> SEQUENCE: 20
gguggacgau uaccagaug                                               19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      Mfn1 forward primer

<400> SEQUENCE: 21
tgaaagctgg ctgtcttgtg                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Mfn1 reverse primer

<400> SEQUENCE: 22
agagccgctc attcacctta                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      Mfn2 forward primer

<400> SEQUENCE: 23
cctcacagag ggctcagaag                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      Mfn2 reverse primer

<400> SEQUENCE: 24
gtccagctcc gtggtaacat                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      p53 forward primer

<400> SEQUENCE: 25

```
agagaccgcc gtacagaaga                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      p53 reverse primer

<400> SEQUENCE: 26
ctgtagcatg ggcatccttt                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      p21 forward primer

<400> SEQUENCE: 27
cggtggaact ttgacttcgt                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      p21 reverse primer

<400> SEQUENCE: 28
cagggcagag gaagtactgg                                              20

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      Glut1 forward primer

<400> SEQUENCE: 29
gatcctgggc cgcttcat                                                18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      Glut1 reverse primer

<400> SEQUENCE: 30
acatgggcac gaagcctg                                                18

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      Hif1alpha forward primer

<400> SEQUENCE: 31
tcaagtcagc aacgtggaag                                              20
```

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      Hif1alpha reverse primer

<400> SEQUENCE: 32
tatcgaggct gtgtcgactg                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      Hk2 forward primer

<400> SEQUENCE: 33
gggacgacgg tacactcaat                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      Hk2 reverse primer

<400> SEQUENCE: 34
gccagtggta aggagctctg                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      Pfk forward primer

<400> SEQUENCE: 35
atggcaaagc tatcggtgtc                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      Pfk reverse primer

<400> SEQUENCE: 36
acacagtccc atttggcttc                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      Pam1 forward primer

<400> SEQUENCE: 37
gcctgatcac cccttctaca                                              20

-continued

```
<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      Pam1 reverse primer

<400> SEQUENCE: 38
tcaagaccct tttcccctct                                               20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      Eno1 forward primer

<400> SEQUENCE: 39
agtacgggaa ggacgccacc a                                             21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      Eno1 reverse primer

<400> SEQUENCE: 40
gcggccacat ccatgccgat                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      Pkm forward primer

<400> SEQUENCE: 41
ctgcaggtga aggagaaagg                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      Pkm reverse primer

<400> SEQUENCE: 42
agatgcaaac accatgtcca                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      Ldha forward primer

<400> SEQUENCE: 43
tggcagcctc ttccttaaaa                                               20
```

-continued

```
<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      Ldha reverse primer

<400> SEQUENCE: 44
cagcttgcag tgtggactgt                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      beta-actin forward primer

<400> SEQUENCE: 45
agccatgtac gtagccatcc                                               20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      beta-actin reverse primer

<400> SEQUENCE: 46
ctctcagctg tggtggtgaa                                               20

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: Synthetic
      ND132 forward primer

<400> SEQUENCE: 47
cccattcgcg ttatctt                                                  17

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      ND132 reverse primer

<400> SEQUENCE: 48
aagttgatcg taacggaagc                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      Atp6ap1 forward primer

<400> SEQUENCE: 49
gccatggaac gacttgaaat                                               20

<210> SEQ ID NO 50
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      Atp6ap1 reverse primer

<400> SEQUENCE: 50
cggagagaag aaaccagcac                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      Sdhb forward primer

<400> SEQUENCE: 51
actggtggaa cggagacaag                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Sdhb reverse primer

<400> SEQUENCE: 52
ttaagccaat gctcgcttct                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      Uqcrc1 forward primer

<400> SEQUENCE: 53
cctacagcac tcgagagcac                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      Uqcrc1 reverse primer

<400> SEQUENCE: 54
aggtgtgccc tggaatgctg                                               20
```